United States Patent
Puttonen et al.

(10) Patent No.: US 12,378,525 B2
(45) Date of Patent: Aug. 5, 2025

(54) REGULATORY MACROPHAGES AND USES THEREOF

(71) Applicant: KUOPIO CENTER FOR GENE AND CELL THERAPY OY, Kuopio (FI)

(72) Inventors: Katja Annina Puttonen, Kuopio (FI); Tuija Kirsi Anneli Kekarainen, Kuopio (FI)

(73) Assignee: KUOPIO CENTER FOR GENE AND CELL THERAPY OY, Kuopio (FI)

( * ) Notice: Subject to any disclaimer, the term of this patent is extended or adjusted under 35 U.S.C. 154(b) by 251 days.

(21) Appl. No.: 17/768,061

(22) PCT Filed: Oct. 12, 2020

(86) PCT No.: PCT/EP2020/078660
§ 371 (c)(1),
(2) Date: Apr. 11, 2022

(87) PCT Pub. No.: WO2021/069754
PCT Pub. Date: Apr. 15, 2021

(65) Prior Publication Data
US 2024/0043804 A1 Feb. 8, 2024

Related U.S. Application Data

(60) Provisional application No. 62/913,766, filed on Oct. 11, 2019.

(51) Int. Cl.
| | | |
|---|---|---|
| *C12N 5/0786* | (2010.01) | |
| *A61K 40/17* | (2025.01) | |
| *A61K 40/22* | (2025.01) | |
| *A61K 40/24* | (2025.01) | |
| *A61K 40/41* | (2025.01) | |
| *A61P 37/06* | (2006.01) | |

(52) U.S. Cl.
CPC ............ *C12N 5/0645* (2013.01); *A61K 40/17* (2025.01); *A61K 40/22* (2025.01); *A61K 40/24* (2025.01); *A61K 40/416* (2025.01); *A61K 40/418* (2025.01); *A61P 37/06* (2018.01); *C12N 2501/22* (2013.01); *C12N 2501/24* (2013.01); *C12N 2501/599* (2013.01)

(58) Field of Classification Search
None
See application file for complete search history.

(56) References Cited

U.S. PATENT DOCUMENTS

2006/0188485 A1 * 8/2006 Kremer .................. A61P 17/00
435/372
2020/0299647 A1 * 9/2020 Hutchinson ............ A61P 25/00

FOREIGN PATENT DOCUMENTS

WO 2017153607 9/2017

OTHER PUBLICATIONS

International Search Report and Written Opinion in corresponding PCT/EP2020/078660, dated Dec. 17, 2020.
Hutchinson, et al., "MITAP-compliant characterization of human regulatory macrophages", Transplant Inter, 2017, 30(8), pp. 765-775.
Di Benedetto, et al., "Macrophages with regulatory functions, a possible new therapeutic perspective in autoimmune diseases", Autoimmunity Reviews, 2019, 18(10), 9 pages.

* cited by examiner

*Primary Examiner* — Daniel C Gamett
(74) *Attorney, Agent, or Firm* — Hovey Williams LLP; Crissa A. Cook

(57) ABSTRACT

The present invention relates to novel immunoregulatory macrophage cells which are useful in the treatment of different immunological and non-immunological diseases and conditions. The cells are characterized by a specific marker and activity pattern which distinguishes them from other cells. The novel immunoregulatory macrophage cells have a high phagocytosing capacity and are capable to suppress the proliferation of T cells. The invention also provides a novel process for preparing immunoregulatory macrophage cells in suspension culture from blood monocytes. The process is amenable to a high degree of automation. In a still further aspect, the invention relates to a pharmaceutical composition comprising the immunoregulatory macrophage cells of the invention.

21 Claims, 17 Drawing Sheets
Specification includes a Sequence Listing.

c.

| Marker | Mreg-bc n samples | Mreg-scn samples | P value | Statistic | Method |
|---|---|---|---|---|---|
| CD11c | 7 | 7 | 0.0052991 | -3.483039 | Welch Two Sample t-test |
| CD14 | 7 | 7 | 0.0039667 | -4.960584 | Welch Two Sample t-test |
| CD16 | 7 | 7 | 0.0046214 | -4.783891 | Welch Two Sample t-test |
| CD163 | 7 | 7 | 0.0217167 | -3.289512 | Welch Two Sample t-test |
| CD38 | 7 | 7 | 0.0030698 | -5.323894 | Welch Two Sample t-test |
| CD40 | 7 | 7 | 0.0328168 | -2.799653 | Welch Two Sample t-test |
| CD51 | 7 | 7 | 0.0000289 | -9.830293 | Welch Two Sample t-test |
| CD71 | 7 | 7 | 0.0002610 | 7.083390 | Welch Two Sample t-test |
| CD86 | 7 | 7 | 0.0011905 | 5.327470 | Welch Two Sample t-test |
| Syn3 | 7 | 7 | 0.0003259 | -7.898487 | Welch Two Sample t-test |

Fig. 1C

SEQUENCE LISTING

```
<160> NUMBER OF SEQ ID NOS: 8

<210> SEQ ID NO 1
<211> LENGTH: 1693
<212> TYPE: DNA
<213> ORGANISM: Homo sapiens

<400> SEQUENCE: 1
gtaggtgaga ggcggctgaa gagttgctgt attctgggaa tgggcagggt cactcgtccg    60
aacagagtcc tatcctacgc ggcggaagag tgtgcccttt gacttgcatc gtctacctac   120
ctctgccatc ctctaccagc cgcaactgcg agggctggag ccaacttcag gactgattga   180
tcatgacttc tataaaggag caggcagcaa ttagcaggct cttaagtttt ttacaggagt   240
gggacaacgc tggcaaagtc gcaaggagtc acatcctcga caagttcatt gaaaccaacc   300
aaggcaagac tgcccctgaa ctggagcagg agttttccca gggagccagt ttgttcctgg   360
tacgcttgac cacctcgctt agaatcacct atatgactga ctcatgttta gaaaagcttc   420
tcaggtccat tggcatcttc ttatcagctg taagcagtaa tcggtacctt atagaatttc   480
ttgaggttgg aggtgtccta accctcttgg aaatacttgg gctagagaag atcaaggagg   540
aggccaagaa ggaatctgtc aaactacttc aggttattgc gaactctggc aggacataca   600
aggaactcat ttgtgaaagc tatggtgtac gatccatagc agaattttg gcaaagtcta   660 agtcagaaga gacccaggag gaagtgcagg ttctgttgga ttctttggtc cacggcaatc   720
ccaagtacca aaatcaagtg tataaaggtc taatagcttt gctgccctgc gagtccccaa   780
aagcccagca gctgtccctg cagactctca ggactgccca gccaatcatt gggaccacac   840
accccagcat cgtggactgc gtgctgaagg tgctgggcac gatgcacctg gaagtccagt   900
atgaagccat cgagttgatc aaagacctgg tcggttacga tgtgcgccag gcgctgctca   960
agggcctcgt ggcgctgctg ataccgtcgg tcaaggagat ctccaaactg caggccaaga  1020
tcctcagtga ccctcggtt ctccagctca ccccagcct gccgatgttt ttgcagcagg  1080
ccgcggccgc caaggccatc ggggtcctgg cgcgcaacga catgagcatc gccgaggagc  1140
tgctgtacct gcgcgtggtg cgtggcctaa tggccgccat gggcaacacg gaccacagca  1200
acagccagcg gctggccagc ctcacgctgg agtgcttcgt gcagatgttc ccttggtgg   1260 cggagcacgt gcgcaagtgc atggggagg aactctacca gctcttcctg agcaacgctg  1320
aggacttgta catgaaaata gacagcattc aggcggacat cttggcggcc aacacagtca  1380
atgttaccaa agccctgtgc ctccatggca gctcctacag catgaacact ctctatggct  1440
cgcgcgattc ggctcagatg gcctacctca cacacttcga ggaggatgta gaatcaaagg  1500
agtaacagcc cctgtggcaa accaggaagg ccaaggctgc ggggcaggga agcctggcaa  1560
```

| | |
|---|---|
| gaggaaggcg cctggggtca agctcagagc cactccactt ggctccaggg gggagacggg | 1620 |
| gattaggcat cccagagggg cagaggaaga gccgctggct gcgaagagtc aataaacagc | 1680 |
| cttgatacct gtc | 1693 |

<210> SEQ ID NO 2
<211> LENGTH: 1715
<212> TYPE: DNA
<213> ORGANISM: Homo sapiens

<400> SEQUENCE: 2

| | |
|---|---|
| aagagagaag agagactgaa acagggagaa gaggcaggag aggaggaggt ggggagagca | 60 |
| cgaagctgga ggccgacact gagggagggc gggaggaggt gaagaaggag agaggggaga | 120 |
| agaggcagga gctggaaagg agagagggag gaggaggagg agatgcggga tgagagacctg | 180 |
| gagttaggtg gcttgggaga gcttaatgaa aagagaacgg agaggaggtg tgggttagga | 240 |
| accaagaggt agccctgggg gcagcagaag gctgagagga gtaggaagat caggagctag | 300 |
| agggagactg gagggttccg ggaaaagagc agaggaaaga ggaaagacac agagagacgg | 360 |
| gagagagaag aagagtgggt ttgaagggcg gatctcagtc cctggctgct ttggcatttg | 420 |
| gggaactggg actccctgtg gggaggagag gaaagctgga agtcctggag ggacagggtc | 480 |
| ccagaaggag gggacagagg agctgagaga gggggcagg gcgttgggca ggggtccctc | 540 |
| ggaggcctcc tggggatggg ggctgcagct cgtctgagcg cccctcgagc gctggtactc | 600 |
| tgggctgcac tgggggcagc agctcacatc ggaccagcac ctgaccccga ggactggtgg | 660 |
| agctacaagg ataatctcca gggaaacttc gtgccagggc ctcctttctg gggcctggtg | 720 |
| aatgcagcgt ggagtctgtg tgctgtgggg aagcggcaga gccccgtgga tgtggagctg | 780 |
| aagagggttc tttatgaccc cttctgcccc ccattaaggc tcagcactgg aggagagaag | 840 |
| ctccggggaa ccttgtacaa caccggccga catgtctcct tcctgcctgc accccgacct | 900 |
| gtggtcaatg tgtctggagg tcccctcctt tacagccacc gactcagtga actgcggctg | 960 |
| ctgtttggag ctcgcgacgg agccggctcg gaacatcaga tcaaccacca gggcttctct | 1020 |
| gctgaggtgc agctcattca cttcaaccag gaactctacg ggaatttcag cgctgcctcc | 1080 |
| cgcggcccca atggcctggc cattctcagc ctctttgtca acgttgccag tacctctaac | 1140 |
| ccattcctca gtcgcctcct taaccgcgac accatcactc gcatctccta caagaatgat | 1200 |
| gcctactttc ttcaagacct gagcctggag ctcctgttcc ctgaatcctt cggcttcatc | 1260 |
| acctatcagg gctctctcag caccccgccc tgctccgaga ctgtcacctg gatcctcatt | 1320 |
| gaccgggccc tcaatatcac ctcccttcag atgcactccc tgagactcct gagccagaat | 1380 |
| cctccatctc agatcttcca gagcctcagc ggtaacagcc ggcccctgca gcccttggcc | 1440 |
| cacagggcac tgaggggcaa cagggacccc cggcaccccg agaggcgctg ccgaggcccc | 1500 |
| aactaccgcc tgcatgtgga tgtgtccccc catggtcgct gagactcccc ttcgaggatt | 1560 |
| gcacccgccc gtcctaagcc tccccacaag gcgaggggag ttacccctaa aacaaagcta | 1620 |
| ttaaagggac agaatacttc ctgttttctc agtggtctga ttctaggcgc ggtggggaaa | 1680 |
| catttgggta ttaaagaaca gacttcttcc ggaaa | 1715 |

<210> SEQ ID NO 3
<211> LENGTH: 1907
<212> TYPE: DNA
<213> ORGANISM: Homo sapiens

<400> SEQUENCE: 3

```
actccgctcg agtagaagtg tgagagagcc cagcaggact cagaggggag agttggagga      60
aaaaaaaagg cagaaaaggg aaagaaagag gaagagagag agagagtgag aggagccgct     120
gagcccaccc cgatggccgc ggacgaagtt gccggagggg cgcgcaaagc cacgaaaagc     180
aaacttttg agtttctggt ccatggggtg cgccccggga tgccgtctgg agcccggatg      240
ccccaccagg gggcgcccat ggcccccg ggctccccgt acatgggcag ccccgccgtg       300
cgacccggcc tggccccgc gggcatggag cccgccgca agcgagcagc gccccgccc        360
gggcagagcc aggcacagag ccagggccag ccggtgccca ccgccccgc gcggagccgc      420
agtgccaaga ggaggaagat ggctgacaaa atcctccctc aaaggattcg ggagctggtc     480
cccgagtccc aggcttacat ggacctcttg gcatttgaga ggaaactgga tcaaaccatc     540
atgcggaagc gggtggacat ccaggaggct ctgaagaggc ccatgaagca aaagcggaag     600
ctgcgactct atatctccaa cacttttaac cctgcgaagc ctgatgctga ggattccgac     660
ggcagcattg cctcctggga gctacgggtg aggggaagc tcctggatga tcccagcaaa      720
cagaagcgga agttctcttc tttcttcaag agtttggtca tcgagctgga caaagatctt     780
tatggccctg acaaccacct cgttgagtgg catcggacac ccacgaccca ggagacggac     840
ggcttccagg tgaaacggcc tggggacctg agtgtgcgct gcacgctgct cctcatgctg     900
gactaccagc ctccccagtt caaactggat ccccgcctag cccggctgct ggggctgcac     960
acacagagcc gctcagccat tgtccaggcc ctgtggcagt atgtgaagac caacaggctg    1020
caggactccc atgacaagga atacatcaat ggggacaagt atttccagca gatttttgat    1080
tgtccccgc tgaagttttc tgagattccc cagcgcctca cagccctgct attgcccct     1140
gacccaattg tcatcaacca tgtcatcagc gtggacctt cagaccagaa gagacggcg    1200
tgctatgaca ttgacgtgga ggtggaggag ccattaaagg ggcagatgag cagcttcctc    1260
ctatccacgg ccaaccagca ggagatcagt gctctggaca gtaagatcca tgagacgatt    1320
gagtccataa accagctcaa gatccagagg gacttcatgc taagcttctc cagagacccc    1380
aaaggctatg tccaagacct gctccgctcc cagagccggg acctcaaggt gatgacagat    1440
gtagccggca accctgaaga ggagcgccgg gctgagttct accaccagcc ctggtcccag    1500
gaggccgtca gtcgctactt ctactgcaag atccagcagc gcaggcagga gctggagcag    1560
tcgctggttg tgcgcaacac ctaggagccc aaaaataagc agcacgacgg aacttcagc    1620
cgtgtcccgg gccccagcat tttgcccgg gctccagcat cactcctctg ccaccttggg    1680
gtgtggggct ggattaaaag tcattcatct gacagcagcc gtgtggtcat ggaaactgg    1740
ggagggagg gggagagaag gggaagggaa gaaggtgggg aggcagtggg tccctcggga    1800
cgactcccca ttcccttccc ttggattctt ctccttactc aattttccct agacctaaaa    1860
acagtttggc agaagacatg tttaataaca ttttcatatt taaaaaa                  1907
```

<210> SEQ ID NO 4
<211> LENGTH: 3464
<212> TYPE: DNA
<213> ORGANISM: Homo sapiens

<400> SEQUENCE: 4

```
gttcctgtcc tcaccacacg gactgagact gatttgatta aagcaccaga gtgtaatggc      60
cctcagagca gggctggtcc tggggttcca caccctgatg accctcctga gcccgcagga     120
ggcaggggcc accaaggctg accacatggg ctcctacgga cccgccttct accagtctta     180
```

```
cggcgcctcg ggccagttca cccatgaatt tgatgaggaa cagctgttct ctgtggacct    240
gaagaaaagc gaggccgtgt ggcgtctgcc tgagtttggt gactttgccc gctttgaccc    300
gcagggcggg ctggccggca tcgccgcaat caaagcccat ctggacatcc tggtggagcg    360
ctccaaccgc agcagagcca tcaacgtgcc tccacgggtg accgtgctcc ccaagtctcg    420
ggtggagctg ggccagccca acatcctcat ctgcatcgtg acaacatctc ccccctgt     480 gatcaatatc acctggctgc gcaacggcca aactgtcact gagggagtgg cccagaccag    540
cttctattcc cagcctgacc atttgttccg caagttccac tacctgccct tcgtgccctc    600
agccgaggac gtctatgact gccaggtgga gcactgggc ctggatgcgc actcctcag    660 gcattgggag ctccaggtgc ctattccacc accagatgcc atggagaccc tggtctgtgc    720
cctgggcctg gccatcggcc tggtgggctt cctcgtgggc accgtcctca tcatcatggg    780
cacatatgtg tccagtgtcc ccaggtaatg atccttctga gagaaatgac ttgtgggaga    840
caccctgcag atcctcatgg gtttgtgaca gcccctgcgt gctcagtgcc ctttaagtgc    900
atcccgctgt gctgactttg agtgggatca acatctgtcc tacgggtccc ctctttttg    960 gccccagtat tcatggcagg gtttgttgga cacctactag cttcccttcc cattcaacac   1020
acacacacat tcttgctcta cccaaagctc tggctggcag cactaaatgc tttggtggtg   1080
tttgcactgt gtccttcca ggccttggcc agttcttcca ggggtgaggc atgtggtgct   1140
ggggattggc agccatcctg gggcccacac aggtgtgtct tgctccattt ggcccattgt   1200
gtgttacttt gtgaatgagc catttcacat ggacttcatg aaatttgcct cctgagttca   1260
ggtttaccct gaaagggatg cagattatcc tgttcctcac gaccccctca gctaacaaca   1320
gttctgaagg gtgctgggac aggacaggct catggggact ccactcctgc ctgggtttac   1380
tctgtatgaa gaggccactg gtatcctgcc atgatgttat ctccttttc tacttttccc   1440 tagagtccca tgcatgataa agagaggccc aaggcttgga taaggtggcc acttccctca   1500
gtggagtcag tcatgttagg taggaggtgg tagagtcggt ctgcgaggta tctcgtaaga   1560
ggggaggtcc acctagacac actctaaata tgtggcctag aagattttgg tctacttttc   1620
tgtgaacaga atttaaaaca tacaaagaga taaatcacca taccacatag tttatgtcag   1680
gaccaaaatg agcaatacag attacggttt tcaaaccaga atgcacataa gaactgcttg   1740
ggatcctttt aaaagtacag gcattggcct ggtgcagtgg ctcattcctg taatcccagc   1800
actttgggag gccaagggga caggactgct tgaggccaag aggtggaaac catcttgggc   1860
tacatagaga gaccccatct ctacaaagaa agatttaaaa attaaccagg catggtggct   1920
cgcacctgta ttcccagcca ctggggaggc tgaggccgga ggagtgcttg agcccaggag   1980
ttcaaggctg cagtgagcca agattgcgcc actgcactcc agcctaggtg acagagtgag   2040
accctgtctc taaataaata aataaataaa atataaaaat aacagtcatc acccagacct   2100
actgaattag aatctcggga gtgcaggggg cagcaacagg gaggctgtct tttctgagat   2160
ggggtctcac tctgtcacca ggctggagtg ccatggcatg atctcagctc actgcaacct   2220
ccacctcctg agttcaagcc attctcctgc ctcagcctcc tgagtagctg ggactacagg   2280
tgtgcgccac tacactcagc taattttgt attttaagta gagacgggt ttcatcatgt   2340 tggccaggat ggcctccatc tcttgacctc gtgatccacc caccttccct cccaaagtac   2400
tggaattaca ggcattagcc actgtgccca gccgaggctg tcatttttaa ccggctctgg   2460
atgactctga tgcagccatc ctggaccttg gctgtggtct ggtaactgga acccagtgac   2520
```

-continued

| | |
|---|---|
| gtaatcaggt gccatcgggg gtcatgggaa aggggatcc ccaaggtctg aggtggacta | 2580 |
| ggaaggcttt ctgaagaacc tgggtctgtt agggcatcag ccaatcaagg tacaagtaaa | 2640 |
| tagaggcaaa atgagggttt gaactgtgag cagttggtcc tggaaaagaa agaaaccaag | 2700 |
| agattatggg gactcaatgg gcttcttaag agagaataag ttgaaatcaa tgaccagaag | 2760 |
| accctgatgg aagtggagga gaatcatctc aggcaaactt tttgtgtgcc agtaacagaa | 2820 |
| accctctttg tgtgatcaca tgcaaagtat aggatatttg caatatagcc atggggagga | 2880 |
| gtgcagggcc caagggtaga ttttagccag gcctcccagg aacagaactc ggatccgaaa | 2940 |
| agcccagaga agctagagct gcccctccaa cactctcgga tccacatggt ctgtgttctc | 3000 |
| tagaccccc tgcatgttag cggtgttctc tctctgtgga ctgactgtcc ttctcagtga | 3060 |
| acatgtccac ccgacagctc ctgagtttat atcatctcaa ccctcacaac ccacagaggc | 3120 |
| tgtgtctcct agtcacagct ttaaattact ggaaaaataa atgactggcc aaacttggag | 3180 |
| caggtgtcca tcccagccct gtgtagttag agcaggaatc aagatctcaa cacaaatgtg | 3240 |
| gctgccaagc actcagcccc ggggcgaggg gtcaagttct tctcagagaa agaggaataa | 3300 |
| gttggttctc agaagacatc acaagatacg tgtgtaccca caatctctg atctctgctg | 3360 |
| atcttttgct tagacgttaa cttgatgcat cattggaaag gtgtttctct catctctgtc | 3420 |
| ctaaggcttg ataaagtcat taaaattgtg ttcttttgac taaa | 3464 |

<210> SEQ ID NO 5
<211> LENGTH: 2056
<212> TYPE: DNA
<213> ORGANISM: Homo sapiens

<400> SEQUENCE: 5

| | |
|---|---|
| gtggagctgc cagagtaaag caaagagaaa ggaagcaggc ccgttggaag tggttgtgac | 60 |
| aaccccagca atgtggagaa gcctggggct tgccctggct ctctgtctcc tcccatcggg | 120 |
| aggaacagag agccaggacc aaagctcctt atgtaagcaa cccccagcct ggagcataag | 180 |
| agatcaagat ccaatgctaa actccaatgg ttcagtgact gtggttgctc ttcttcaagc | 240 |
| cagctgatac ctgtgcatac tgcaggcatc taaattagaa gacctgcgag taaaactgaa | 300 |
| gaaagaagga tattctaata tttcttatat tgttgttaat catcaaggaa tctcttctcg | 360 |
| attaaaatac acacatctta agaataaggt ttcagagcat attcctgttt atcaacaaga | 420 |
| agaaaaccaa acagatgtct ggactctttt aaatggaagc aaagatgact tcctcatata | 480 |
| tgatagatgt ggccgtcttg tatatcatct tggtttgcct ttttccttcc taactttccc | 540 |
| atatgtagaa gaagccatta agattgctta ctgtgaaaag aaatgtggaa actgctctct | 600 |
| cacgactctc aaagatgaag acttttgtaa acgtgtatct ttggctactg tggataaaac | 660 |
| agttgaaact ccatcgcctc attaccatca tgagcatcat cacaatcatg acatcagca | 720 |
| ccttggcagc agtgagcttt cagagaatca gcaaccagga gcaccaaatg ctcctactca | 780 |
| tcctgctcct ccaggcctc atcaccacca taagcacaag ggtcagcata ggcagggtca | 840 |
| cccagagaac cgagatatgc cagcaagtga agatttacaa gatttacaaa agaagctctg | 900 |
| tcgaaagaga tgtataaatc aattactctg taaattgccc acagattcag agttggctcc | 960 |
| taggagctga tgctgccatt gtcgacatct gatatttgaa aaaacagggt ctgcaatcac | 1020 |
| ctgacagtgt aaagaaaacc tcccatcttt atgtagctga cagggacttc gggcagagga | 1080 |
| gaacataact gaatcttgtc agtgacgttt gcctccagct gcctgacaaa taagtcagca | 1140 |
| gcttataccc acagaagcca gtgccagttg acgctgaaag aatcaggcaa aaaagtgaga | 1200 |

```
atgaccttca aactaaatat ttaaaatagg acatactccc caatttagtc tagacacaat    1260
ttcatttcca gcattttat aaactaccaa attagtgaac caaaaataga aattagattt     1320
gtgcaaacat ggagaaatct actgaattgg cttccagatt ttaaatttta tgtcatagaa    1380
atattgactc aaaccatatt ttttatgatg gagcaactga aaggtgattg cagcttttgg    1440
ttaatatgtc ttttttttc ttttccagt gttctatttg ctttaatgag aatagaaacg      1500
taaactatga cctaggggtt tctgttggat aattagcagt ttagaatgga ggaagaacaa    1560
caaagacatg ctttccattt ttttctttac ttatctctca aaacaatatt actttgtctt    1620
ttcaatcttc tacttttaac taataaaata agtggatttt gtattttaag atccagaaat    1680
acttaacacg tgaatatttt gctaaaaaag catatataac tattttaaat atccatttat    1740
cttttgtata tctaagactc atcctgattt ttactatcac acatgaataa agcctttgta    1800
tctttctttc tctaatgttg tatcatactc ttctaaaact tgagtggctg tcttaaaaga    1860
tataagggga aagataatat tgtctgtctc tatattgctt agtaagtatt tccatagtca    1920
atgatggttt aataggtaaa ccaaacccta taaacctgac ctcctttatg gttaatacta    1980
ttaagcaaga atgcagtaca gaattggata cagtacggat ttgtccaaat aaattcaata    2040
aaaaccttaa agctga                                                    2056

<210> SEQ ID NO 6
<211> LENGTH: 914
<212> TYPE: DNA
<213> ORGANISM: Homo sapiens

<400> SEQUENCE: 6
gcagaaactg gccttccatc tctctcagac accaagctgc agatccaggc ttttctggga    60
aagtgaggcc accatggctc tggagaagtc tcttgtccgg ctccttctgc ttgtcctgat    120
actgctggtg ctgggctggg tccagccttc cctgggcaag gaatcccggg ccaagaaatt    180
ccagcggcag catatggact cagacagttc ccccagcagc agctccacct actgtaacca    240
aatgatgagg cgccggaata tgacacaggg gcggtgcaaa ccagtgaaca cctttgtgca    300
cgagcccctg gtagatgtcc agaatgtctg tttccaggaa aaggtcaccct gcaagaacgg    360 gcagggcaac tgctacaaga caactccag catgcacatc acagactgcc gcctgacaaa    420
cggctccagg taccccaact gtgcataccg gaccagcccg aaggagagac acatcattgt    480
ggcctgtgaa gggagcccat atgtgccagt ccactttgat gcttctgtgg aggactctac    540
ctaaggtcag agcagcgaga taccccacct ccctcaacct catcctctcc acagctgcct    600
cttccctctt ccttccctgc tgtgaaagaa gtaactacag ttagggctcc tattcaacac    660
acacatgctt ccctttcctg agtcccatcc ctgcgtgatt ttggggtgga agagtgggtt    720
gtgaggtggg ccccatgtta acccctccac tctttctttc aataaaacgc agttgcaaac    780
acctgatttc tgaagcggtt ctgtctaggt actgttctg gcattgcctt ccagcaaggg    840
gtaagaactg taaatctgat tcactttgga gaacggtgaa tggagtaatt aaatgccttc    900
ccttctgact tgga                                                      914

<210> SEQ ID NO 7
<211> LENGTH: 1158
<212> TYPE: DNA
<213> ORGANISM: Homo sapiens

<400> SEQUENCE: 7
```

```
agacaccgtg tcctcttgcc tgggagaggg gaagcagatc tgaggacatc tctgtgccag    60
gccagaaacc gcccacctgc agttccttct ccgggatgga cgtggggccc agctccctgc   120
cccaccttgg gctgaagctg ctgctgctcc tgctgctgct gccccctcagg ggccaagcca   180 acacaggctg ctacgggatc ccagggatgc ccggcctgcc cggggcacca gggaaggatg   240
ggtacgacgg actgccgggg cccaaggggg agccaggaat cccagccatt cccgggatcc   300
gaggacccaa agggcagaag ggagaacccg gcttacccgg ccatcctggg aaaaatggcc   360
ccatgggacc ccctgggatg ccaggggtgc ccggccccat gggcatccct ggagagccag   420
gtgaggaggg cagatacaag cagaaattcc agtcagtgtt cacggtcact cggcagaccc   480
accagccccc tgcacccaac agcctgatca gattcaacgc ggtcctcacc aacccgcagg   540
gagattatga cacgagcact ggcaagttca cctgcaaagt ccccggcctc tactactttg   600
tctaccacgc gtcgcataca gccaacctgt gcgtgctgct gtaccgcagc ggcgtcaaag   660
tggtcacctt ctgtgggcac acgtccaaaa ccaatcaggt caactcgggc ggtgtgctgc   720
tgaggttgca ggtgggcgag gaggtgtggc tggctgtcaa tgactactac gacatggtgg   780
gcatccaggg ctctgacagc gtcttctccg gcttcctgct cttccccgac tagggcgggc   840
agatgcgctc gagccccacg ggccttccac ctccctcagc ttcctgcatg gacccacctt   900
actggccagt ctgcatcctt gcctagacca ttctccccac cagatggact tctcctccag   960
ggagcccacc ctgaccccacc cccactgcac ccccctccca tgggttctct ccttcctctg  1020
aacttcttta ggagtcactg cttgtgtggt tcctgggaca cttaaccaat gccttctggt  1080
actgccattc ttttttttt tttttttcaag tattggaagg ggtggggaga tatataaata  1140
aatcatgaaa tcaataca                                                 1158
```

<210> SEQ ID NO 8
<211> LENGTH: 5604
<212> TYPE: DNA
<213> ORGANISM: Homo sapiens

<400> SEQUENCE: 8

```
gcgcagccgg gagagcggag tctcctgcct cccgccccccc acccctccag ctcctgctcc    60
tcctccgctc cccatacaca gacgcgctca caccgctcc ctcactcgca cacacagaca   120
caagcgcgca cacaggctcc gcacacacac ttcgctctcc cgcgcgctca cacccctctt   180
gccctgagcc cttgccggtg cagcgcggcg ccgcagctgg acgcccctcc cgggctcact   240
ttgcaacgct gacggtgccg gcagtggccg tggaggtggg aacagcggcg gcatcctccc   300
ccctggtcac agcccaagcc aggacgcccg cggaacctct cggctgtgct ctcccatgag   360
tcgggatcgc agcatccccc accagccgct caccgcctcc gggagccgct gggcttgtac   420
accgcagccc ttccgggaca gcagctgtga ctcccccca gtgcagattt cgggacagct   480
ctctagaaac tcgctctaaa gacggaaccg ccacagcact caaagcccac tgcggaagag   540
ggcagcccgg caagcccggg ccctgagcct ggacccttag cggtgccggg cagcactgcc   600
ggcgcttcgc ctcgccggac gtccgctcct cctacactct cagcctccgc tggagagacc   660
cccagcccca ccattcagcg cgcaagatac cctccagata tgccctgcgt ccaagcccaa   720
tatagccctt cccctccagg ttccagttat gcggcgcaga catacagctc ggaatacacc   780
acggagatca tgaaccccga ctacaccaag ctgaccatgg accttggcag cactgagatc   840
acggctacag ccaccacgtc cctgcccagc atcagtacct tcgtggaggg ctactcgagc   900
aactacgaac tcaagccttc ctgcgtgtac caaatgcagc ggcccttgat caaagtggag   960
```

```
gaggggcggg cgcccagcta ccatcaccat caccaccacc accaccacca ccaccaccat    1020
caccagcagc agcatcagca gccatccatt cctccagcct ccagcccgga ggacgaggtg    1080
ctgcccagca cctccatgta cttcaagcag tccccaccgt ccaccccac cacgccggcc     1140 ttccccccgc aggcggggc gttatgggac gaggcactgc cctcggcgcc cggctgcatc     1200
gcacccggcc cgctgctgga cccgccgatg aaggcggtcc ccacggtggc cggcgcgcgc    1260
ttcccgctct tccacttcaa gccctcgccg ccgcatcccc ccgcgccag cccggccggc     1320 ggccaccacc tcggctacga cccgacggcc gctgccgcgc tcagcctgcc gctgggagcc    1380
gcagccgccg cgggcagcca ggccgccgcg cttgagagcc acccgtacgg gctgccgctg    1440
gccaagaggg cggccccgct ggccttcccg cctctcggcc tcacgccctc ccctaccgcg    1500
tccagcctgc tgggcgagag tcccagcctg ccgtcgccgc ccagcaggag ctcgtcgtct    1560
ggcgagggca cgtgtgccgt gtgcggggac aacgccgcct gccagcacta cggcgtgcga    1620
acctgcgagg gctgcaaggg cttttttcaag agaacagtgc agaaaaatgc aaaatatgtt   1680
tgcctggcaa ataaaaactg cccagtagac aagagacgtc gaaaccgatg tcagtactgt    1740
cgatttcaga agtgtctcag tgttggaatg gtaaaagaag ttgtccgtac agatagtctg    1800
aaagggagga gaggtcgtct gccttccaaa ccaaagagcc cattacaaca ggaaccttct    1860
cagccctctc caccttctcc tccaatctgc atgatgaatg cccttgtccg agctttaaca    1920
gactcaacac ccagagatct tgattattcc agatactgtc ccactgacca ggctgctgca    1980
ggcacagatg ctgagcatgt gcaacaattc tacaacctcc tgacagcctc cattgatgta    2040
tccagaagct gggcagaaaa gattccggga tttactgatc tccccaaaga agatcagaca    2100
ttacttattg aatcagcctt tttggagctg tttgtcctca gactttccat caggtcaaac    2160
actgctgaag ataagtttgt gttctgcaat ggacttgtcc tgcatcgact tcagtgcctt    2220
cgtggatttg gggagtggct cgactctatt aaagactttt ccttaaattt gcagagcctg    2280
aaccttgata tccaagcctt agcctgcctg tcagcactga gcatgatcac agaaagacat    2340
gggttaaaag aaccaaagag agtcgaagag ctatgcaaca agatcacaag cagtttaaaa    2400
gaccaccaga gtaagggaca ggctctggag cccaccgagt ccaaggtcct gggtgccctg    2460
gtagaactga ggaagatctg caccctgggc ctccagcgca tcttctacct gaagctggaa    2520
gacttggtgt ctccaccttc catcattgac aagctcttcc tggacaccct accttctaa    2580 tcaggagcag tggagcagtg agctgcctcc tctcctagca cctgcttgct acgcagcaaa    2640
gggataggtt tggaaaccta tcatttcctg tccttcctta agaggaaaag cagctcctgt    2700
agaaagcaaa gactttcttt tttttctggc tcttttcctt acaacctaaa gccagaaaac    2760
ttgcagagta ttgtgttggg gttgtgtttt atatttaggc attggggat ggggtgggag     2820 ggggttatag ttcatgaggg ttttctaaga aattgctaac aaagcacttt tggacaatgc    2880
tatcccagca ggaaaaaaaa ggataatata actgttttaa aactctttct ggggaatcca    2940
attatagttg ctttgtattt aaaaacaaga acagccaagg gttgttcgcc agggtaggat    3000
gtgtcttaaa gattggtccc ttgaaaatat gcttcctgta tcaaaggtac gtatgtggtg    3060
caaacaaggc agaaacttcc tttttaatttc cttcttcctt tatttaaaca aatggtgaaa    3120
gatggaggat tacctacaaa tcagacatgg caaaacaata tggctgtttt gcttccataa    3180
acaagtgcaa tttttttaaag tgctgtctta ctaagtcttg tttattaact ctcctttatt    3240
ctatatggaa ataaaaagga ggcagtcatg ttagcaaatg acacgttaat atccctagca    3300
```

```
gaggctgtgt tcaccttccc tgtcgatccc ttctgaggta tggcccatcc aagactttta    3360
ggccattctt gatggaacca gatccctgcc ctgactgtcc agctatcctg aaagtggatc    3420
agattataaa ctggattaca tgtaactgtt ttggttgtgt tctatcaacc ccaccagagt    3480
tccctaaact tgcttcagtt atagtaactg actggtatat tcattcagaa gcgccataag    3540
tcagttgagt atttgatccc tagataagaa catgcaaatc agcaggaact ggtcatacag    3600
ggtaagcacc agggacaata aggatttttta tagatataat ttaattttg ttattggtta    3660 aggagacaat tttggagagc aagcaaatct ttttaaaaaa tagtatgaat gtgaatacta    3720
gaaaagattt aaaaaatagt atgagtgtga gtactaggaa ggattagtgg gctgcgtttc    3780
aacattccgt gttcgtactc cctttttgtat gtttctactg ttaatgccat attactatga    3840
gataatttgt tgcatagtgt ccttatttgt ataaacattt gtatgcacgt tatattgtaa    3900
tagctttgcc tgtatttatt gcaagaccac cagctcctgg aagctgagtt acagagtaat    3960
taaatggggt gttcacagtg acttggatac accaattaga aattaaataa gcaaatatat    4020
atatatatat aaatatagca ggttacatat atatatttat aatgtgtctt tttattaacc    4080
atttgtacaa taaatgtcac ttcccatgcc gttatttat ggttcatttg cagtgacttt    4140
taaggcagta ctgtttagca cttgatatt aaaattttgc ttatgttttg ctaaattcga    4200
ataatgtttg aagatttta ggtctaaaag tctttatatt atatactctg tatcaagtca    4260
aaatatcttt ggccatttttg ctaagaaaca aactttgaat gtcaaactga tgtcacagta    4320 gttttttgtta gctttaaatc attttttgctt tagtctttt aaaggaaaat aacaaaacta    4380
tgctgtttat attgtcatta aattatacaa tcaaacaaat gccaaatgaa ttgcctaatt    4440
gctgcaaagt ataccccaga taggaaatca tatgtttttt tccaagagtc attctaatat    4500
ttgattatgt tatgtgtgct tttatgaaag attgttattt ttatatatca agatgataga    4560
acctggaatg ttaggatttt gaaatgttag acttggaagg ggcctggtct gtcaactagt    4620 ccaaccccctt aaaattcata gaggagcaaa ctggggccca ttgaagggtg aagagttact    4680
caaggtcaaa cagctggtaa cagaatcaag actaagacct aatttacctt tccatactct    4740
ttttttttct caacttcatc tatataaaat caggcttttta aacataacca ctaatattta    4800
cctgaagata accatgagta aagtatactt ttgcattaat ttttttgagct tatatgcaaa    4860 cataataaat attattaaat atcaggaaag ctaacatttc atacaagata gcttcagacc    4920
aaattcaaat tgaatttgaa taaattagaa atactgtgca tacataacct tcttgtgcac    4980
catgagtatt tggaaagtta atccttgttt ttgtcgtgtc tataaaggaa gaacaaaaca    5040
aaataaaaac agagccctag agaaatgctg ttacttttta ttttttacacc catcagattt    5100 aaggaaaaga cttttttagcc attataatct agtggttgga aggaatgaag aagctttttt    5160
agtaataggt ccagatatga gtgctaaaaa taaagatgat agcatgttct tctgtcttcc    5220
atagttatta caactatgag agcctcccaa gtcatcttat caactcaact cccttttttt    5280
tgtcttaatg ttgcacataa gtttatacag agtggatgac cacactagca cagaagagaa    5340
caacatgtat taaagcaggt gattcctccc cttggcggga gagctctctc agtgtgaaca    5400
tgccttctgt gggcggaaat caggaagcca ccagctgtta atggagagtg ccttgctttt    5460
atttcagaca gcagagtttt ccaaagtttc tctgctcctc taacagcatt gctctttagt    5520
gtgtgttaac ctgtggtttg aaagaaatgc tcttgtacat taacaatgta aatttaaatg    5580
attaaattac attttatcaa tggc                                            5604
```

REGULATORY MACROPHAGES AND USES THEREOF

RELATED APPLICATIONS

This application is the U.S. National Stage of International Patent Application No. PCT/EP2020/078660, filed Oct. 12, 2020, which is hereby incorporated by reference in its entirety, and which claims priority to U.S. Provisional Patent Application No. 62/913,766, filed Oct. 11, 2019.

SEQUENCE LISTING

The following application contains a sequence listing submitted as an ASCII text file via EFS-Web in computer readable format (CRF) to serve as both the paper copy and CRF in compli-ance with 37 CFR 1.821. The ASCII text file is entitled "Sequence_Listing," created on Mar. 29, 2022, as 25,193 bytes, and the content of the ASCII text file is incorporated by reference herein.

FIELD OF THE INVENTION

The present invention relates to novel immunoregulatory macrophage cells which are useful in the treatment of different immunological and non-immunological diseases and conditions. The cells are characterized by a specific marker and activity pattern which distinguishes them from other cells. The novel immunoregulatory macrophage cells have a high phagocytosing capacity and are capable to suppress the proliferation of T cells. The invention also provides a novel process for preparing immunoregulatory macrophage cells in suspension culture from blood monocytes. The process is amenable to a high degree of automation. In a still further aspect, the invention relates to a pharmaceutical composition comprising the immunoregulatory macrophage cells of the invention.

TECHNICAL BACKGROUND

Regulatory macrophages (referred to herein and in the literature as "Mregs") reflect a unique state of macrophage differentiation, which is distinguished from macrophages in other activation states by their robust phenotype as well as their immunosuppressive, anti-inflammatory, and angiogenic properties.

Human Mregs have been found to be particularly effective as an immune-conditioning therapy in solid organ transplantations. Most significantly, the cells suppress mitogen-stimulated T-cell proliferation in vitro, which can be attributed to interferon (IFN) γ-induced indoleamine 2,3-dioxygenase activity, as well as contact-dependent deletion of activated T cells. In addition, Mregs drive the development of activated induced regulatory T cells that, in turn, suppress the proliferation of effector T cells and inhibit the maturation of dendritic cells. Therefore, when Mregs are administered to a recipient, it is hypothesized that a feed-forward loop of immunologic regulation is initiated leading to the long-term immunologic acceptance of a foreign transplant or prevention of immunopathology. Mreg-containing cell preparations have been administered to kidney transplant recipients as a form of adjunct immunosuppressive treatment in a series of case studies and two early-phase clinical trials [1]-[5]. These studies have demonstrated the feasibility of Mregs in suppressing immunologic reactions resulting in organ rejection. Transplantation studies with Mregs manufactured ex vivo have shown that the cells are safe and well-tolerated [6].

Mregs have also been used for the treatment of other clinical conditions, such as non-healing diabetic foot ulcers which are associated with defects in peripheral arterial function. In this respect, WO 2019/053091 A1 describes the use of Mregs for treating macroangiopathies or microangiopa-thies of the lower limbs. Further, Mregs were suggested for ischemia or reperfusion associated diseases [7].

Several protocols are known in the art which use blood monocytes as a starting material for preparing Mreg cells. Mononuclear leucocytes are isolated from peripheral blood samples by a commonly known method, such as leukapheresis. After isolation of the monocytes, the cells are incubated in a culture medium containing macrophage colony-stimulating factor (M-CSF) or granulo-cyte macrophage colony-stimulating factor (GM-CSF) and human serum, such as human AB serum (HABS). After 3-6 days the cells are stimulated with interferon gamma (IFN-γ) for additional 18-24 hours before harvesting the Mreg cells.

Mregs had typically been manufactured in tissue culture flasks [2]-[4]. However, monocytes and their derivatives adhere tightly to hard plastic or glass surfaces, such that harvesting requires scraping the Mregs from the surfaces which results in a significant loss of viable cells that can be used for therapy. Accordingly this approach is not feasible for preparing high amounts of Mregs for clinical use. WO 2017/153607 A1 describes an improved method for manufacturing Mregs which uses gas-permeable differentiation bags. When differentiating monocytes in these bags, a homogenous population of Mregs is obtained which differ in terms of their phenotype and func-tionality from their flask-cultured counterparts. Nevertheless, the cells grow semi-adherently in the bags, so that it is still somewhat cumbersome to harvest the cells from the bags without an undesirable viability loss.

As a consequence, there is a need in the art for improved methods that can be used for the preparation of Mreg cells from blood monocytes. The methods should be GMP-compliant and include a minimum number of interventions which could affect sterility of the resulting therapeutic cell product. In addition, to allow for the economic manufacturing of high amounts of the therapeutic cell product, the methods should be amenable to up-scaling and automation.

SUMMARY OF THE INVENTION

The present invention provides a novel process for producing Mreg that is highly effective for producing Mregs and minimizes sterility and harvesting problems. The process allows sub-jecting the whole batch of cells obtained from monocytes enrichment to differentiation in suspension in a single bioreactor bag. Therefore, the process can be readily up-scaled to an industrial-scale and avoids additional enzymes or harsh harvesting methods, thereby guaranteeing high quality of the product. Further, the process can also be applied to all different types of regulatory macrophages, including those described in the art, e.g. in WO 2017/153607 A1. Regulatory macrophages had not been differentiated earlier in suspension, as it was assumed that for gaining the regulatory phenotype, monocytes need at least a transient adherence to the surface of the culture system [6].

Surprisingly, as described hereinbelow, the process gives rise to a novel type of Mreg cell. Specifically, the inventors found that when the monocytes used for preparing the Mreg cells were cultured in suspension, i.e. without any significant adherence of the cells to the surface of the cell container, Mreg cells of a unique phenotype were obtained that exert immunoregulatory properties that render them highly suitable for cell-based therapeutic approaches. These cells are designated "Mregs-sc" herein to distinguish them over known Mregs. Notably, the cells obtained by the method of the invention are not occurring naturally in the human body. Instead they are a unique cell type that develops in response to the culturing of monocytes in the presence of the growth factors and cytokines as described hereinbelow.

Accordingly, in a first aspect the invention relates to a method for producing Mreg cells which includes the culturing of monocytes from a blood sample of a subject in suspension culture without letting a significant portion of the cells adhere to the inner surface of the culturing container in the presence of M-CSF/GM-CSF, a CD16 ligand (such as an immunoglobulin), and IFN-γ.

In a second aspect, the invention refers to a novel type of Mreg cell, i.e. the Mreg-sc cell, which is obtainable by a method referred to in the first aspect of the invention. The Mreg-sc cell has a unique phenotype which has not been observed in the prior art. The Mreg-sc cell mediates biological activities that confer useful therapeutic properties which are unique to this cell type and have not been described in the prior art. In particular, the Mreg-sc cell exerts immunosuppressive, anti-inflammatory and tissue-reparative properties which distinguish them from naturally occurring macrophages and render them highly attractive for therapeutic purposes.

In a third aspect, the invention refers to a pharmaceutical composition comprising the Mreg-sc cell according to the second aspect of the invention or a sub-cellular fraction of said cell. The pharmaceutical composition containing the new cell type of the invention may also contain further active ingredients or excipients as needed.

In a fourth aspect, the invention refers to the use of Mreg-sc cells according to the second aspect of the invention or a sub-cellular fraction thereof or a pharmaceutical composition according to the third aspect of the invention for therapeutic purposes, in particular for the suppression of adverse immunological reactions.

In a fifth aspect, the invention refers to a process for preparing a sub-cellular fraction of an Mreg-sc cell according to the second aspect of the invention by decomposing the Mreg-sc cell under suitable conditions.

Finally, in a sixth aspect, the invention refers to a process for preparing an immunoregulatory T cell by co-culturing T cells from a blood sample of a subject with an Mreg-sc cell according to the second aspect of the invention or a sub-cellular fraction thereof.

DETAILED DESCRIPTION OF THE INVENTION

According to the invention Mreg cells are derived from human CD14+ blood monocytes. In order to induce the characterizing biological properties of Mreg-sc cells, the monocytes are grown in suspension culture and treated with a specific combination of growth factors, cytokines and receptor ligands. The cells obtained from the process of the invention are characterized by a unique phenotype that distinguishes them from blood monocytes, other types of monocyte-derived macrophages, monocyte-derived dendritic cells and other suppressive myelomonocytic cell products described in the prior art.

Accordingly, in a first aspect, the present invention relates to a process for preparing an immunoregulatory macrophage cell, said process comprising:
 (a) isolating CD14 positive monocytes from a blood sample of a subject;
 (b) culturing the monocytes in a culture medium containing (i) M-CSF and/or GM-CSF, and (ii) a CD16 ligand;
 (c) contacting the monocytes or monocytes-derived cells with IFN-γ; and
 (d) obtaining the immunoregulatory macrophage cell from the culture medium,
wherein steps (b) and (c) are performed in a container that is agitated to minimize or essentially avoid adherence of the cells to the surface of the container. The agitation of the container that minimizes or essentially avoids adherence of the cells to the surface of the container is maintained at least for 4 days, at least for 5 days, at least for 6 days, or at least for 7 days of cell culturing. More preferably, the agitation of the container is maintained for the complete culturing period, i.e. for the whole of the time period between introducing the monocytes into the culturing containers to harvesting of the Mregs-sc.

The process of the invention uses blood monocytes as starting material. While it will be preferred that the process of the invention is used for generating Mreg cells from human blood monocytes, the invention is not limited to the differentiation of cells of human origin. In fact, the invention is applicable also to other types of non-human cells, in particular vertebrate cells, e.g. non-human primate or pig cells. In this way, the invention provides an important contribution in the field of xenogenic transplantation medicine.

According to a preferred embodiment, the method of the invention is used to differentiate CD14 positive monocytes of a human donor into Mregs. The monocytes which serve as a starting material for the method of the invention are obtained from the peripheral blood of a human donor. The donor may be a healthy subject or a patient suffering from one or more diseases. In one preferred embodiment, the monocyte donor also is the recipient of the Mreg cells (autologous approach). In another preferred embodiment, the monocyte donor is a person that differs from the recipient of the Mreg cells (allogeneic approach). In the latter case, the donor and recipient may be genetically related or unrelated. In another embodiment, the monocyte donor at the same time donates an organ to the recipient of the Mreg cells. The preferred relationship between donor and recipient depends upon the clinical application. The use of autologous Mreg cells may be preferred to avoid certain adverse reactions. Therefore the use of autologous Mreg cells is preferred in the case of regenerative or anti-inflammatory therapies. In the transplant setting, the use of donor-derived Mreg cells as immunosuppressive therapy is preferred because donor antigen-expressing cells are more effective than recipient-derived cells.

Different methods are known in the art for the enrichment of mononuclear cells from peripheral blood, and each of these methods can be used in the context with the present invention. For example, blood obtained by venepuncture can be treated with an anticoagulant and subsequently separated by use of a separation medium, such as Ficoll-Paque Plus. For this, the anticoagulant-treated blood sample is layered on the Ficoll-Paque Plus solution and centrifuged, which will result in the formation of layers containing the different cell types. The bottom layer contains erythrocytes which have been aggregated and sedimented by the Ficoll-Paque Plus reagent. The layer immed-iately above the erythrocyte layer contains mostly granulocytes which have migrated through the Ficoll-Paque Plus layer. Owing to their lower density, monocytes and lymphocytes are found at the interface between the plasma and the Ficoll-Paque Plus. Enrichment of the mononuclear cell fraction can be achieved by isolation of the layer and subsequent washing and centrifugation.

Another routinely used method for separating mononuclear leucocytes from blood samples includes leukapheresis. Leukapheresis is a specific type of apheresis in which white blood cells are obtained from peripheral blood according to their relative densities in a continuous process. In this procedure, the blood of a subject is passed through a special centrifugation device which collects the pre-defined fraction of white blood cells and returns the remaining blood cells and plasma back to the donor. Today, leukapheresis is a routine clinical measure for obtaining leucocytes or stem cells from peripheral blood. Different devices are available from several manufactures that can be used for performing leukapheresis in the context with the present invention, e.g. the COBE® Spectra Apheresis System from Terumo BCT. Where the leukapheresis is carried out by use of the COBE® Spectra Apheresis System, it is preferred to use the manual protocol provided by the manufacturer, since this protocol was found to result in better quality monocytes compared to the AutoPBSC protocol.

The above methods and devices for leucocyte enrichment will provide a cell fraction that contains, apart from the monocytes, also lymphocytes. According to the invention, monocytes may be further enriched and separated from lymphocytes by known methods, e.g. by magnetic bead separation, sorting by flow cytometry, elutriation, filtration or plastic adherence, before the cells are introduced into the preparation method of the present invention. However, it is not mandatory to use a homogeneous monocyte fraction in the method of the invention. In fact, the presence of an amount of 0.1-20%, and more preferably 0.1-1%, lymphocytes in the monocyte fraction may posi-tively influence the differentiation of monocytes to regulatory macrophages.

In one preferred embodiment of the invention, the monocyte fraction used in the method of the invention is essentially pure and contains less than 15%, less than 10%, less than 5%, less than 4%, less than 3%, less than 2%, or less than 1% percent of non-monocytic nucleated blood cells, such as lymphocytes or granulocytes. For obtaining a mononuclear cell preparation that is enriched for monocytes, peripheral blood mononuclear cells may be contacted, e.g., with CD14 mi-crobeads to which CD14-positive monocytes bind. In one embodiment, the monocytes in step (a) are isolated by leukapheresis and subsequent subjected to a separation step using CD14 affinity molecules, preferably CD14 antibodies. Such a purification step massively reduces contamination of the starting material with non-monocytes. Reduction of T cell contamination is very valuable from a patient safety perspective because it minimizes the potential risk of donor-versus-recipient reactions.

In a preferred embodiment of the invention, the CD14-positive monocytes which are used in the method of the invention have been isolated with a cell manufacturing device, such as the CliniMACS® Technology (Miltenyi Biotec GmbH, Bergisch Gladbach, Germany). For example, the GMP-compliant, fully-closed LP14 process can be used according to manufacturer's instructions (LP-14 System User Manual) for CD14 monocyte enrichment. This method is based on the labeling of monocytes with iron-dextran particles conjugated with an anti-CD14 antibody, and further selection via a magnetic separation column. In a particularly preferred embodiment of the present invention, the CD14 monocytes from peripheral blood samples are separated or enriched by using the CliniMACS Prodigy® device.

The CD14-positive monocyte fraction, which has been isolated as described above, can directly be used for differentiation by incubation with M-CSF and/or GM-CSF and the CD16 ligand, or it can be stored in autologous plasma supplemented with Anticoagulant Citrate Dextrose Solution (ACD-A) or any other suitable buffer until further use. If the monocyte fraction has to be trans-ported to a different site where the differentiation process is carried out, care should be taken that differentiation of the cells by incubation with M-CSF/GM-CSF is started within 24 hours after isolation of the cells, preferably within 18 hours, within 12 hours, within 6 hours, within 4 hours, or within 2 hours after isolation of the monocytes. For long term storage, the monocyte fraction may be resuspended in a suitable cryopreservation solution and stored at temperatures below 20° C., preferably below 80° C. for extended periods of time.

To initiate the conversion of the enriched monocytes to Mregs, the cells are incubated in the presence of M-CSF/GM-CSF and a CD16 ligand. Preferably, the cells may be introduced in a medium that contains M-CSF and/or GM-CSF and a CD16 ligand. Alternatively, it is also possible to add M-CSF/GM-CSF and the CD16 ligand some time after start of cell culturing. The culture medium used in step (b) of the above method can be any medium that has been described in the literature as suitable for use in the culturing of monocytes and/or macrophages. Suitable culturing media include, for example, the PromoCell Macrophage Generation Medium (PromoCell GmbH, Hei-delberg, Germany), Dulbecco's modified Eagle's medium (DMEM), DMEM: F12 blend, Medium 199, or RPMI-1640 medium. The culture medium preferably is a chemically defined medium. Apart from M-CSF/GM-CSF, the culture medium can contain other factors to promote the survival and differentiation of Mregs, including: growth factors and cytokines, such as epidermal growth factor (EGF), or IL-4; fatty acids, cholesterol and other lipids; vitamins, transferrin and trace elements; insulin, glucocorticoids, cholecalciferol or ergocalciferol, and other hormones; non-specific immunoglobulin and other plasma proteins. In a preferred embodiment of the invention, the culture medium is RPMI-1640 or a medium derived therefrom.

The culture medium used for incubating the isolated CD14 positive monocytes contains M-CSF (also known as CSF1), GM-CSF (also known as CSF2) or both. M-CSF is known in the art as a hematopoietic growth factor that influences the proliferation, differentiation, and survival of monocytes, macrophages, and bone marrow progenitor cells. GM-CSF is a monomeric glycoprotein that functions as a cytokine and is secreted by macrophages, T cells, mast cells, NK cells, endothelial cells and fibroblasts. M-CSF and GM-CSF proteins from different species have been described and can be purchased from different manufacturers. The choice of the M-CSF and/or GM-CSF used in the method of the invention will depend on the origin of the monocytes which are to be differentiated into Mreg cells. For example, if human monocytes are differentiated to Mregs using the process described herein, the medium used will contain human M-CSF and/or human GM-CSF, preferably recombinant human M-CSF and/or recombinant human GM-CSF. Similarly, if porcine monocytes are used in the differentiation method, the M-CSF and/or GM-CSF added to the medium will be of porcine origin. In a particularly preferred embodiment of the invention, the M-CSF and/or GM-CSF is of human origin, such as recombinant human M-CSF and/or GM-CSF, and the monocytes are human monocytes.

The skilled person will be able to find an amount of M-CSF and/or GM-CSF which is suitable for differentiating a high proportion of the monocytes into Mregs-sc by routine methods. Usually, the concentration of M-CSF in the culture medium in step (b) of the above method is in the range of 1-100 ng protein per ml medium. As taught, for example, in WO 2017/153607 A1, time-course experiments to measure the amount of M-CSF in the culture medium revealed that M-CSF was consumed or degraded over time, such that cultures with an initial dose of 5 ng/ml M-CSF contained sub-physiological concentrations by day 2 of culturing; in contrast, cultures with an initial dose of 25 ng/ml M-CSF maintained concentrations of >10 ng/ml throughout a 7-day culturing period. Thus, in a preferred embodiment of the invention, the concentration of M-CSF in the culture medium is in the range of 20-75 ng/ml, 20-50 ng/ml or 20-25 ng/ml. A concentration of at least 25 ng M-CSF per ml culture medium is particularly preferred. Preferably, the above concentrations refer to recombinant human M-CSF.

Where GM-CSF is used instead of M-CSF, the same concentrations can be used in the medium as outlined above in the context with M-CSF. Since GM-CSF appears to be more potent compared to M-CSF, a concentration of GM-CSF of 0.1-100 ng protein per ml medium is suggested herein. In cases where both M-CSF and GM-CSF are used in the medium, the overall concentrations of these two growth factors will be in the above-mentioned range, i.e. in the range of 20-75 ng/ml, 20-50 ng/ml or 20-25 ng/ml. An overall concentration of M-CSF and GM-CSF of 25 ng per ml culture medium is particularly preferred.

Apart from the M-CSF and/or GM-CSF, the culture medium used in step (b) of the above method also comprises a CD16 ligand. It has been found that stimulation of the CD16 cell surface receptor on the monocytes is required to induce their differentiation into Mreg-sc cells. More specifically, experiments revealed that monocytes grown in medium supplemented with human AB serum (HABS) develop into Mregs, whereas monocytes grown in medium supplemented with fetal calf serum (FCS) do not develop into Mregs. Monocytes grown in an equal mixture of both sera develop the Mreg-phenotype. Therefore, HABS contains a positive Mreg-inducing activity. Re-moval of the chloroform-extractable fraction of HABS demonstrated that the Mreg-inducing activity of HABS principally resided within the chloroform-resistant fraction, so was likely to be a protein. By size-fractionation, the principal protein component of HABS responsible for Mreg development was found to be >100 kDa leading to the hypothesis that the unknown factor was immunoglobulin (Ig). HABS depleted of Ig using protein A/G sepharose was unable to support the development of Mreg morphology and DHRS9 mRNA expression. Re-addition of elutriated Ig back into the Ig-depleted serum (or addition of IVIg) restored its ability of to induce DHRS9 expression. Similarly, when monocytes were cultured in FCS supplemented with human Ig, an increase in the DHRS9 mRNA expression was observed compared to FCS-alone controls and normal Mreg morphology was obtained. Monocytes treated with anti-FcγRIII antibody expressed significantly lower levels of DHRS9 mRNA than monocytes treated with anti-FcγRI (CD64), anti-FcγRIIa/b (CD32a/b) or control antibody and did not develop Mreg morphology. Blockade of either FcγRIIb or DC-SIGN alone, or both receptors together, had no effect on the generation of DHRS9+ Mregs. To reinforce the observation that FcγRIII is necessary for Mreg generation, FcγRIII expression was silenced using siRNA. A transient suppression of FCGR3A and FCGR3B transcript expression was achieved in freshly isolated monocytes cultured in 10% HABS; importantly, FCGR2B expression was not decreased by this manipulation. Knockdown of FcγRIII at the protein level was demonstrated by flow cytometry (35.2%±4.4 CD16+ cells using negative control siRNA, versus 15.3%±3.7 with FCGR3 siRNA; n=4, p=0.002). Silencing FcγRIII expression (but not suppression of MAPK1 expression or treatment with a negative-control siRNA) re-sulted in a significant down-regulation of DHRS9 mRNA expression.

It was concluded that serum Ig acts through FcγRIII (CD16) to induce the Mreg phenotype. The dependence of Mreg differentiation on FcγRIII distinguishes the Mreg from other Ig complex-induced macrophage types described in the prior art. In particular, the mode of derivation distinguishes the FcγRIII-induced Mreg from the FcγRIIb-induced macrophage, FcγRI-induced macrophage and macrophages generated in the absence of immunoglobulin which were described in the prior art.

As stimulation of the CD16 cell surface receptor is crucial for the differentiation into the desired Mreg phenotype, the method of the invention includes the incubation of the monocytes with a CD16 ligand in step (b). The ligand which binds to the receptor will preferably be a human or non-human immunoglobulin, and more preferably a human immunoglobulin, or a fragment thereof. The immunoglobulin fragment can be, for example, an Fc fragment of an immunoglobulin. The immunoglobulin or immunoglobulin fragment is preferably added to a serum-free culture medium. Alternatively, recombinant proteins may be used which comprise a sequence of an immunoglobulin or immunoglobulin fragment, such as a sequence of a human immunoglobulin. In another embodiment, a non-human or human antibody or a fragment thereof which specifically binds to CD16 through its antigen recognition domain is used to promote Mreg-sc differentiation. In still another embodiment, small molecules are used to stimulate the CD16 signaling pathway to promote Mreg-sc differentiation.

In a preferred embodiment, the medium used for generating the Mreg cells contains 1-20% human serum or equivalent amounts of certain serum components, such as immunoglobulin. More preferably, the medium is supplemented with 10% serum. If serum-containing media are used for carrying out the method of the invention, the media comprise between 5-15%, preferably 10%, human serum. A medium containing 10% human AB serum is particularly preferred. Stated differently, it is preferred that the serum is added in a concentration of about 0.01 to 10%, preferably about 0.1 to 1%, and more preferably about 1%. Slightly lower concentrations can be used when using immunoglobulin or immunoglobulin fragments as CD16 ligands. Substantially lower concentrations may be used if immunoglobulin or other CD16 ligands are immobilized on tissue culture surfaces, beads or other physical matrices. It is preferred that the human serum, such as AB serum, is derived from male donors. Where serum is used from female donors, preferably the donors do not use progesterone or progesterone-oestrogen contraceptives. It is further preferred that said medium should not contain antibodies against monocytes or Mreg cells or any intermediate form, including antibodies against major histocompatibility molecules.

It was found that antibiotics in the culture medium had no measurable effect on the viability, yield, phenotype or suppressive function of the Mregs-sc produced by the method of the invention. Nevertheless, it is preferred that the medium used in step (b) of the method of the invention does not contain any antibiotic.

Where the Mregs-sc cells are intended for use in therapeutic applications in which the induction of angiogenesis is desired (see below), the medium used for culturing the monocytes in step (b) of the method of the invention may comprise, apart from M-CSF/GM-CSF and the CD16 ligand, a toll-like receptor (TLR) ligand, such as lipolysaccharide (LPS), monophosphoryl lipid A (MPLA) or High Mobility Group Box protein 1 (HMGB1) to enhance the production of angiogenic factors like VEGF-A. The TLR ligand can be added to the culture medium in a concentration range of 10 ng/ml to 1 µg/ml, preferably between 50-500 ng/ml, such as 100 ng/ml, 200 ng/ml, 300 ng/ml, or 400 ng/ml. In cases where more than one TLR ligand is added, the overall, combined concentrations of these ligands should be in the above-recited range. The TLR ligand can be added at any stage of the production method. It can be present in the initial medium which is used for culturing the monocytes, i.e. at day 0 of the culture, or it can be added at a later stage, e.g. at day 5, 6 or 7 of the culture. Preferably, the TLR ligand is added simultaneously with the addition of the IFN-γ.

According to the invention, the step of culturing the cells in the presence of M-CSF/GM-CSF and the CD16 ligand as well as the step culturing the cells in the presence of IFN-γ are performed in a container that is agitated to avoid adherence of the cells to the surface of the container. Therefore, the cells are cultured non-adherently in a suspension culture. This is achieved by performing steps (b) and (c) of the method of the invention in a bioreactor which constantly agitates the container that comprises the cells, e.g. a bag, gently so that the cells cannot adhere to the inner surface of the container. It has been found that a wave-type bioreactor is particularly useful for this purpose. As used herein, a wave-type bioreactor is preferably used for suspension culturing. A wave-type bioreactor provides for mixing of cells and culturing medium by a wave-type motion of the culturing medium. One example for a wave-type bioreactor for use in the method of the invention is the Xuri™ Cell Expansion System (GE Healthcare). This wave-type of bioreactor was originally developed and validated for expansion of T cells, and its mechanistic principle is that the cell culture is always in motion.

Once the monocytes have been suspended in a suitable medium, the suspension can be transferred into a suitable container which is adapted to receive a cell culture and can be used for culturing the cells under defined conditions. The container can be of a material that is compatible with cell culturing, e.g. glass or plastic. In a preferred embodiment, the container is made of plastic, e.g. ethylene vinyl alcohol (EVOH), ethylene vinyl acetate copolymer (EVA), polyolefine or the like. In another preferred embodiment, the container is made of a polyethylene, such as low-density polyethylene (LDPE) or linear low-density polyethylene (LLDPE). In yet another embodiment, the container is a plastic bag made of any of the above materials.

The volume of the container which is used for differentiating the monocytes into Mreg-sc cells, e.g. a bag, is at least 0.5 L, and preferably at least 1.0 L, at least 1.5 L, at least 2.0 L, at least 2.5 L, at least 3.0 L, at least 3.5 L, at least 4.0 L, at least 4.5 L, or at least at least 5.0 L or more. The ratio of cell suspension volume to the volume of the container, e.g. the bag, is at least about 1:6, at least 1:5, at least 1:4, at least 1:3, or at least 1:2. A ratio of 1:2 means that 1 L cell suspension is used in a 2 L container. For example, if a 2 L bag is used, the volume of the cell suspension will be between 0.3 L and 1 L, with 0.5 to 0.6 L being particularly preferred. If a 10 L bag is used, the volume of the cell suspension will be between 1.5 L and 5 L, with 2.5 to 3.0 L being particularly preferred. If a 20 L bag is used, the volume of the cell suspension will be between 3.0 L and 10 L, with 5.0 to 6.0 L being particularly preferred. In a particularly preferred embodiment, the Xuri™ Cell Expansion System is used with a bag having a volume of 2 L, 10 L or 20 L.

After the monocytes have been transferred to the containers, e.g. the culturing bags, the cells are incubated in the containers in the presence of M-CSF/GM-CSF and the CD16 ligand, e.g. human serum or human immunoglobulins, for at least 3 days prior to IFN-γ stimulation. As used herein, a culturing period of "1 day" refers to 24 hours of culturing. Accordingly, a culturing period of "at least 3 days" refers to 72 hours of culturing or more. The optimal period of IFN-γ stimulation is at least 12 hours, preferably 18 hours, and more preferably 24 hours. According to the invention, the total culturing period, i.e. the time period from introducing the monocytes into the culturing containers to harvesting of the Mregs-sc is at least 4 days, but preferably at least 5 days, at least 6 days, at least 7 days or at least 8 days. Preferably, the time period from introducing the monocytes into the culturing containers to harvesting of the Mregs-sc is not longer than 9 days. Stated differently, the total culturing period is between 4 and 8 days, preferably between 6 and 8 days, more preferably 7 days. The monocytes in the containers are incubated under conditions that allow for their growth and differentiation into Mreg-sc cells. The general conditions for culturing monocytes or macrophages are known to a person working in the field of cell culturing.

For example, the bags containing the suspensions can be transferred to an incubation chamber which allows the selection of defined conditions of temperature, humidity and $CO_2$. Suitable conditions a temperature in the range of 30-40° C., preferably between 32°–38° C., and more preferably between 37-38° C., e.g. 37° C. The humidity used for culturing is normally in the range of 30-70%, preferably 40-60%, and more preferably 50-60%, e.g. 60% humidity. The incubation chamber may include up to 10% $CO_2$. A content of up to 5% $CO_2$, up to 4% $CO_2$, up to 3% $CO_2$, up to 2% $CO_2$, or up to 1% $CO_2$ is particularly preferred.

All culturing steps of the method of the invention are performed such that majority of the cells in the containers remain in suspension and do not adhere to a surface of the container, e.g. the bottom of the container. Preferably, the culturing is performed such that not more than 10% of the cells in the container, and more preferably not more than 5% or not more than 1% of the cells in the container adhere to an inner surface of the container, e.g. the bottom of the container. This is achieved by constantly agitating the container at a degree so as to minimize adhesion of the cells. The required agitation speed will depend on the size of the cell container and the bioreactor device that is used for culturing and differentiation. A skilled person will readily be able to determine the minimum agitation speed that prevents adhesion and retains the cells in suspension based on routine experimentation. For example, if the Xuri™ Cell Expansion System is used for culturing and differentiation, an agitation speed of between 2-10 rpm, and more preferably 2-6 rpm, and even more preferably 2-4 rpm, can be used. The angle of the tray preferably is adjusted to 2-12°, more preferably 2-8°, and even more preferably 2-4°.

In step (c) of the method of the invention, the cells are contacted with the cytokine interferon gamma (IFN-γ). The cytokine is known in the art to alter the transcription of more than 30 genes, thereby producing a variety of physiological and cellular responses. IFN-γ proteins have been isolated from different species and can be purchased from different manufacturers. The choice of the IFN-γ used in the method of the invention will depend on the origin of the monocytes which are subjected to the method of the invention. For example, if human monocytes are differentiated to Mregs-sc using the process described herein, the IFN-γ added will be human IFN-γ, preferably recombinant human IFN-γ. Similarly, if porcine monocytes are used in the differentiation method, the IFN-γ added to the medium will be of porcine origin. In a particularly preferred embodiment of the invention, the IFN-γ is human IFN-γ, more preferably recombinant human IFN-γ.

Any amount of IFN-γ may be added that is effective to induce the expression of indoleamine 2,3-dioxygenase (IDO1) by the monocytes in the culture. Preferably, the amount of IFN-γ to be added to the monocyte culture will be in the range of 5-100 ng/ml, more preferably between 10-80 ng/ml, still more preferably between 20-50 ng/ml. An amount of 25 ng IFN-γ per ml culture medium is particularly preferred herein.

The IFN-γ can be added to the medium simultaneously with the M-CSF/GM-CSF and the CD16 ligand which means that the cytokine may be added, e.g., at the time when the monocytes are introduced into the container in which differentiation is performed. In such an embodiment, the monocytes to be differentiated by the method of the invention will be cultured in the presence of M-CSF/GM-CSF, the CD16 ligand and IFN-γ for the entire culturing period. It is however preferred that the culturing period in the presence of IFN-γ is considerably shorter than the culturing period in the presence of M-CSF/GM-CSF, which means that the IFN-γ is added only after the cells have been cultured for at least 3 days in the presence of M-CSF/GM-CSF. In a preferred embodiment, the IFN-γ is added after having cultured the cells for 3-6 days in the presence of M-CSF/GM-CSF. Preferably, the cells have been cultured for at least 3 days, at least 4 days, at least 5 days, or at least 6 days in the presence of M-CSF/GM-CSF before the addition of IFN-γ. In a particularly preferred embodiment, the IFN-γ is added after having cultured the cells for 3-6 days in the presence of M-CSF/GM-CSF, and culturing is then continued for another 18-72 hours.

In a particularly preferred embodiment of the invention, the differentiated cells are harvested at day 7, e.g. after 6 days of culturing the monocytes in the medium containing M-CSF/GM-CSF and the CD16 ligand followed by 18-24 hours IFN-γ stimulation. Where several containers have been cultured in parallel, the content of the containers may be pooled at the end of the culturing process. The differentiated macrophages may be washed by a buffer which is compatible for use with macrophages. For example, Ringer solution or Phosphate Buffered Saline (PBS), preferably supplemented with 5% human serum albumin, can be used for washing the cells by serial exchange of the buffer by centrifugation and decanting the supernatant. As the cells do not adhere to the surface of the container, the harvesting step of the method of the invention does not include the addition of trypsin.

Preferably, the harvesting step (d) of the method of the invention does not include the mechanical detachment of cells from the surface of the container, e.g. the scraping of the cells from the inner surface of the container. In a preferred embodiment, harvesting of the cell is performed by use of a counter flow centrifugation device, such as the Gibco CTS Rotea Counterflow Centrifugation system. Such a device uses a counter flow technique for separating cells from the culture medium and forming a compact pellet (see, e.g. U.S. Pat. No. 1,009,922 8B2). The cells are floating inside the liquid bed and are thus more protected from the shear stress than during conventional centrifugation. By adjusting both centrifugation force and the speed of counter flow it is possible to separate debris and dead cells from the living Mreg-sc cells, thereby purifying the final product.

In a particular preferred embodiment, the counter flow centrifugation device may also used for transfer of the monocytes from the enrichment device into the bioreactor. For example, if a CliniMACS Prodigy® device is used for monocyte enrichment, the monocytes can be transferred into the wave-type reactor, e.g. to the Xuri™ Cell Expansion System. For this purpose, the bag for culturing the monocytes of the Xuri™ Cell Expansion System is sterilely welded to the tubing system of counter flow centrifugation device. In this way, Mreg differentiation can be performed as a fully-closed process.

After harvesting the cells, the quality of the differentiation process can be determined by measuring IP-10 (interferon-gamma induced protein 10). The IP-10 protein is produced and secreted in the surrounding medium by the Mreg cells in response to IFN-γ stimulation. Accordingly, the concentration of IP-10 in the medium is associated with the number of differentiated Mreg-sc cells. For this reason, the concentration of IP-10 in the culture medium can be used as a quality control marker for the preparation process. In this way, it is not required to use the cells resulting from the process for quality control purposes. In a preferred embodiment, a concentration of greater than 5,000 pg IP-10 per ml culture medium indicates a sufficient differentiation of the monocytes into Mreg-sc cells. Preferably, a concentration of greater than 10,000 pg, greater than 15,000 pg, greater than 20,000 pg, greater than 25,000 pg, or greater than 30,000 pg per ml culture medium indicates sufficient differentiation.

These Mreg-sc cells can be transferred and stored in a transfusion bag, a glass infusion device or in another closed-system container which allow for the transportation of the cells to the treatment centre or to the patient's bedside. For this purpose, the differentiated cells will be suspended in a suitable preservation medium. The preservation medium can be, for example, Ringer solution, which is preferably supplemented with 5% human serum albumin. In a particularly preferred embodiment, the preservation medium is a ready-to-use medium which is serum-free and/or protein-free. A suitable ready-to-use medium which is commercially available is HypoThermosol® FRS (Stemcell Technologies SARL, Köln, Germany). Preferably, the medium has a pH of between 6.5 and 8.0, more preferably between 7.0 and 7.5, such as 7.4. The cell solution should be stored at 4° C. to minimize energy consumption and cell adhesion. Alternatively, Mreg-sc cells may be re-suspended in cryopreservation solution, such as 10% Dimethylsulfoxid plus human AB serum (DMSO-HABS). and stored in a frozen form until final use.

The phenotypic and functional stability of the differentiated macrophage cells of the invention depends upon the choice of excipient and storage temperature. When resuspended in Ringer solution supplemented with human serum albumin, the macrophages of the invention are stable at 20° C. to 25° C. for up to 24 hours after cell harvest. When resuspended in Plasmalyte/PBS supplemented with 5% human serum albumin, the macrophages can be stored at 2-8° C., preferably 4° C., for at least 48 hours after cell harvest. When longer storage periods are required, the cells may be subjected to freezing or cryopreservation. Generally, it was found that the cells of the invention are stable in their immunosuppressive phenotype.

The method for preparing Mreg-sc cells of the invention can be automated according to common methods, e.g. by using a GMP-compliant platform which offers integrated solutions that streamline cell-processing workflows. The process preferably occurs in a "closed system" which takes advantage of closed disposables, optional customization of tubing sets, buffers and reagents, multiple input lines with sterile filters, output line for optional in-process controls and substantially reduced clean room requirements. For example, the platform may comprise a cell separation system enabling the separation of monocytes from the white blood cell fraction. The cell separation system should be able to separate monocytes from a starting volume of 100-1000 ml apheresate or whole peripheral blood. The monocytes contained in the isolated mononuclear white blood cell fractions may then be isolated, e.g. via magnetic beads, that bind to CD14+ cells. These cells are then cultured in an appropriate culture medium. The platform allows providing media, growth factors and/or cytokines to the cell culture via multiple input ports. At the end of the culturing process, the cells are automatically washed, harvested and transferred into appropriate sterile de-livery bags. A customized tube sealer may be used that permits sterile sealing of PVC and EVA tubes. The cellular product may be bar-coded, and the whole manufacturing process may be moni-tored online for quality control purposes.

In a second aspect, the invention refers to a novel type of Mreg cell, referred to as Mreg-sc cell (abbreviation for "Mreg derived from suspension culture"), which is obtainable by the method of the first aspect of the invention. As used herein, a regulatory macrophage or "Mreg" is a macrophage cell capable of preventing mitogen-stimulated allogeneic or autologous T cell proliferation. The cells provided by the invention are monocyte-derived human macrophages and, as such, express common leukocyte markers and macrophage lineage markers, in particular CD45 and CD33. Mreg-sc cells also express the markers CD85h, CD258, and CD206.

It was found that Mregs-sc cells consistently express the characteristic markers CD16, CD163, and Syndecan-3. This is to surprising it has been reported that all other Mregs lack expression of CD16, and CD163 expression. Accordingly, these markers are highly suitable for distinguishing Mregs-sc cells over previously known Mregs. In addition, Mreg-sc cells also express the markers CD51, CD72 and CD11c. All human Mregs, either cultured in bags, in flasks or in suspension, express relatively high levels of DHRS9, a retinol dehydrogenase of the SDR family of retinol dehydrogenases.

Similarly, all human Mreg cells express indoleamine 2,3-dioxygenase (IDO1) which is normally not observed in other monocyte-derived macrophage types described in the prior art. In previous studies, IDO1 has been identified as one of the key molecules in immune regulation, and in particular, in dampening the effector T cell-mediated adverse inflammatory responses [8]-[10]. The proposed mechanisms include direct elimination of effector T cells by tryptophan deprivation [11]-[12] and indirect immunoregulation via Stat3-mediated induction of regulatory T cells. As such, it has been identified as one of the main candidates to measure the potency and therapeutic potential of monocyte-derived cell therapy products. IFN-γ is a potent inducer of transcription of the IDO1 gene. IFN-γ is added during manufacturing of both Mreg-bc and Mreg-sc, as well as during generation of pro-inflammatory M1 macrophages, but not to anti-inflammatory M2a. As a consequence IDO1 expression is not detected in M2a on protein level and appears to be downregulated on the level of transcribed mRNA when compared to the CD14+ monocytes.

Accordingly, in one embodiment the invention provides a novel type of immunoregulatory macrophage which is characterized by the expression of the markers CD16, CD163, and Syndecan-3. In one embodiment, a macrophage is provided that expresses the markers CD16, CD51, CD163 and Syndecan-3. In another embodiment, a macrophage is provided that expresses the markers CD16, CD11c, CD163 and Syndecan-3. In yet another embodiment, a macrophage is provided that expresses the markers CD16, CD11c, CD51, CD163 and Syndecan-3. In yet another embodiment, a macrophage is provided that expresses the markers CD16, CD11c, CD51, CD72, CD163 and Syndecan-3. Preferably, the macrophage also expresses the marker IDO1.

Herein, a cell is negative for a particular surface marker if its fluorescence intensity as measured by flow cytometry is less than the fluorescence intensity of the 99th percentile of a corresponding isotype control-stained sample.

The Mreg-sc cells are furthermore either negative for CD38, or they express low levels of CD38. During the generation of Mreg-sc cells, the initial population of monocytes downregulates CD38 expression at the cell surface. Down-regulation of CD38 during Mreg-bc development can be expressed as the percentage of CD38 expression on Mregs-sc at day 7 compared to monocytes on day 0 (d0) of culture. The expression of CD38 is proportional to the difference in mean fluorescence intensity between an isotype control-stained cell and the specific CD38 signal. Hence, % down-regulation=$100-100\times(CD38d7-Isod7)/(CD38d0-Isod0)$, wherein CD38d7 is the specific signal on day 7; Isod7 is the isotype control signal on day 7; CD38d0 is the specific signal on day 0; Isod0 is the isotype control signal on day 0. The down-regulation of CD38 by Mregs-sc cells can be conveniently determined by using standard flow cytometry methods. According to a preferred embodiment, the expression of CD38 by the Mreg-sc cell is downregulated by more than 50% relative to the initial expression of CD38 by monocytes on day 0 of culture, more preferably by more than 60%, by more than 70%, by more than 80%, by more than 90%, by more than 95% or by more than 99%.

Hence, the Mreg-sc cells provided by the method of the invention are macrophages which can be described by one of the following marker patterns:

(1). $CD16^+$, $CD163^+$, Syndecan-$3^+$,
(2). $CD16^+$, $CD51^+$, $CD163^+$, Syndecan-$3^+$,
(3). $CD16^+$, $CD11c^+$, $CD163^+$, Syndecan-$3^+$,
(4). $CD16^+$, $CD51^+$, $CD11c^+$, $CD163^+$, Syndecan-$3^+$,
(5). $CD16^+$, $CD163^+$, Syndecan-$3^+$, $CD72^+$,
(6). $CD16^+$, $CD51^+$, $CD163^+$, Syndecan-$3^+$, $CD72^+$,
(7). $CD16^+$, $CD11c^+$, $CD163^+$, Syndecan-$3^+$, $CD72^+$,
(8). $CD16^+$, $CD51^+$, $CD11c^+$, $CD163^+$, Syndecan-$3^+$, $CD72^+$,
(9). $CD16^+$, $CD163^+$, Syndecan-$3^+$, $IDO1^+$,
(10). $CD16^+$, $CD51^+$, $CD163^+$, Syndecan-$3^+$, $IDO1^+$,
(11). $CD16^+$, $CD11c^+$, $CD163^+$, Syndecan-$3^+$, $IDO1^+$,
(12). $CD16^+$, $CD51^+$, $CD11c^+$, $CD163^+$, Syndecan-$3^+$, $IDO1^+$,
(13). $CD16^+$, $CD163^+$, Syndecan-$3^+$, $CD72^+$, $IDO1^+$,
(14). $CD16^+$, $CD51^+$, $CD163^+$, Syndecan-$3^+$, CD72, $IDO1^+$,
(15). $CD16^+$, $CD11c^+$, $CD163^+$, Syndecan-$3^+$, $CD72^+$, $IDO1^+$, (16). CD16$^+$, CD51$^+$, CD11c$^+$, CD163$^+$, Syndecan-3$^+$, CD72$^+$, IDO1$^+$,
(17). CD16$^+$, CD163$^+$, Syndecan-3$^+$, CD86$^{low}$,
(18). CD16$^+$, CD51$^+$, CD163$^+$, Syndecan-3$^+$, CD86$^{low}$,
(19). CD16$^+$, CD11c$^+$, CD163$^+$, Syndecan-3$^+$, CD86$^{low}$,
(20). CD16$^+$, CD51$^+$, CD11c$^+$, CD163$^+$, Syndecan-3$^+$, CD86$^{low}$,
(21). CD16$^+$, CD163$^+$, Syndecan-3$^+$, CD72$^+$, CD86$^{low}$,
(22). CD16$^+$, CD51$^+$, CD163$^+$, Syndecan-3$^+$, CD72$^+$, CD86$^{low}$,
(23). CD16$^+$, CD11c$^+$, CD163$^+$, Syndecan-3$^+$, CD72$^+$, CD86$^{low}$,
(24). CD16$^+$, CD51$^+$, CD11c$^+$, CD163$^+$, Syndecan-3$^+$, CD72$^+$, CD86$^{low}$,
(25). CD16$^+$, CD163$^+$, Syndecan-3$^+$, IDO1$^+$, CD86$^{low}$,
(26). CD16$^+$, CD51$^+$, CD163$^+$, Syndecan-3$^+$, IDO1$^+$, CD86$^{low}$,
(27). CD16$^+$, CD11c$^+$, CD163$^+$, Syndecan-3$^+$, IDO1$^+$, CD86$^{low}$,
(28). CD16$^+$, CD51$^+$, CD11c$^+$, CD163$^+$, Syndecan-3$^+$, IDO1$^+$, CD86$^{low}$,
(29). CD16$^+$, CD163$^+$, Syndecan-3$^+$, CD72$^+$, IDO1$^+$, CD86$^{low}$,
(30). CD16$^+$, CD51$^+$, CD163$^+$, Syndecan-3$^+$, CD72, IDO1$^+$, CD86$^{low}$,
(31). CD16$^+$, CD11c$^+$, CD163$^+$, Syndecan-3$^+$, CD72$^+$, IDO1$^+$, CD86$^{low}$,
(32). CD16$^+$, CD51$^+$, CD11c$^+$, CD163$^+$, Syndecan-3$^+$, CD72$^+$, IDO1$^+$, CD86$^{low}$,
(33). CD16$^+$, CD163$^+$, Syndecan-3$^+$, CD83$^{low}$,
(34). CD16$^+$, CD51$^+$, CD163$^+$, Syndecan-3$^+$, CD83$^{low}$,
(35). CD16$^+$, CD11c$^+$, CD163$^+$, Syndecan-3$^+$, CD83$^{low}$,
(36). CD16$^+$, CD51$^+$, CD11c$^+$, CD163$^+$, Syndecan-3$^+$, CD83$^{low}$,
(37). CD16$^+$, CD163$^+$, Syndecan-3$^+$, CD72$^+$, CD83$^{low}$,
(38). CD16$^+$, CD51$^+$, CD163$^+$, Syndecan-3$^+$, CD72$^+$, CD83$^{low}$,
(39). CD16$^+$, CD11c$^+$, CD163$^+$, Syndecan-3$^+$, CD72$^+$, CD83$^{low}$,
(40). CD16$^+$, CD51$^+$, CD11c$^+$, CD163$^+$, Syndecan-3$^+$, CD72$^+$, CD83$^{low}$,
(41). CD16$^+$, CD163$^+$, Syndecan-3$^+$, IDO1$^+$, CD83$^{low}$,
(42). CD16$^+$, CD51$^+$, CD163$^+$, Syndecan-3$^+$, IDO1$^+$, CD83$^{low}$,
(43). CD16$^+$, CD11c$^+$, CD163$^+$, Syndecan-3$^+$, IDO1$^+$, CD83$^{low}$,
(44). CD16$^+$, CD51$^+$, CD11c$^+$, CD163$^+$, Syndecan-3$^+$, IDO1$^+$, CD83$^{low}$,
(45). CD16$^+$, CD163$^+$, Syndecan-3$^+$, CD72$^+$, IDO1$^+$, CD83$^{low}$,
(46). CD16$^+$, CD51$^+$, CD163$^+$, Syndecan-3$^+$, CD72, IDO1$^+$, CD83$^{low}$,
(47). CD16$^+$, CD11c$^+$, CD163$^+$, Syndecan-3$^+$, CD72$^+$, IDO1$^+$, CD83$^{low}$,
(48). CD16$^+$, CD51$^+$, CD11c$^+$, CD163$^+$, Syndecan-3$^+$, CD72$^+$, IDO1$^+$, CD83$^{low}$,
(49). CD16$^+$, CD163$^+$, Syndecan-3$^+$, CD370$^{low}$,
(50). CD16$^+$, CD51$^+$, CD163$^+$, Syndecan-3$^+$, CD370$^{low}$,
(51). CD16$^+$, CD11c$^+$, CD163$^+$, Syndecan-3$^+$, CD370$^{low}$,
(52). CD16$^+$, CD51$^+$, CD11c$^+$, CD163$^+$, Syndecan-3$^+$, CD370$^{low}$,
(53). CD16$^+$, CD163$^+$, Syndecan-3$^+$, CD72$^+$, CD370$^{low}$,
(54). CD16$^+$, CD51$^+$, CD163$^+$, Syndecan-3$^+$, CD72$^+$, CD370$^{low}$,
(55). CD16$^+$, CD11c$^+$, CD163$^+$, Syndecan-3$^+$, CD370$^{low}$,
(56). CD16$^+$, CD51$^+$, CD11c$^+$, CD163$^+$, Syndecan-3$^+$, CD72$^+$, CD370$^{low}$,
(57). CD16$^+$, CD163$^+$, Syndecan-3$^+$, IDO1$^+$, CD370$^{low}$,
(58). CD16$^+$, CD51$^+$, CD163$^+$, Syndecan-3$^+$, IDO1$^+$, CD370$^{low}$,
(59). CD16$^+$, CD11c$^+$, CD163$^+$, Syndecan-3$^+$, IDO1$^+$, CD370$^{low}$,
(60). CD16$^+$, CD51$^+$, CD11c$^+$, CD163$^+$, Syndecan-3$^+$, IDO1$^+$, CD370$^{low}$,
(61). CD16$^+$, CD163$^+$, Syndecan-3$^+$, CD72$^+$, IDO1$^+$, CD370$^{low}$,
(62). CD16$^+$, CD51$^+$, CD163$^+$, Syndecan-3$^+$, CD72, IDO1$^+$, CD370$^{low}$,
(63). CD16$^+$, CD11c$^+$, CD163$^+$, Syndecan-3$^+$, CD72$^+$, IDO1$^+$, CD370$^{low}$,
(64). CD16$^+$, CD51$^+$, CD11c$^+$, CD163$^+$, Syndecan-3$^+$, CD72$^+$, IDO1$^+$, CD370$^{low}$, The expression of the markers can be determined on the mRNA or protein level. For marker determination on the protein level, the marker profile of the Mreg-sc cell can conveniently be determined by using standard flow cytometry methods. Flow cytometry is a widely used method for analyzing the expression of cell surface markers and intracellular molecules. It is routinely used for applications like cell counting, cell sorting, and biomarker profiling. In particular it can be used for defining different cell types in a heterogeneous cell population. Flow cytometry normally comprises measuring fluorescence intensity produced by fluorescent-labeled antibodies that detect markers on the cell surface. Although it can also be used for the detection of intracellular markers, such detection is less desirable, since the antibody must permeate the cell which normally kills the cell. This prevents the detection of intracellular markers for cell sorting applications which aims at the provision of viable homogeneous cell populations. Thus, intracellular markers like IDO1 are determined on the mRNA level, e.g. by commonly known methods which allow for the quantitative or semi-quantitative detection of mRNA levels, for example, quantitative RT-PCR (e.g., TaqMan™ RT-PCR), real-time RT-PCR, Northern-Blot analysis or the like.

According to the invention, several genes have been identified in a transcriptomic analysis which can be used for distinguishing Mregs from other macrophages, such as M0, M1 or M2a macrophages. These gens include the ARMH1 gene (armadillo like helical domain containing 1-NCBI Reference Sequence: NM_001145636.2—SEQ ID NO:1), the CA11 (carbonic anhydrase 11-NCBI Reference Sequence: NM_001217.5—SEQ ID NO:2), the SMARCD3 gene (SWI/SNF related, matrix associated, actin dependent regulator of chromatin, subfamily d, member 3-NCBI Reference Sequence: NM_001003801.2—SEQ ID NO:3), and the HLA-DOA gene (major histocompatibility complex, class II, DO alpha-NCBI Reference Sequence: NM_002119.4—SEQ ID NO:4). While the genes ARMH1, CA11, and SMARCD3 are expressed at the same level in M0, M1 and M2a cells, they are more than 4-fold stronger expressed in Mregs. HLA-DOA has more than 8-fold higher expression Mregs compared to other macrophages. Accordingly, in another preferred embodiment an Mreg cell is provided that expresses any of the surface marker patterns (1)-(64), more preferably CD16$^+$, CD163$^+$, Syndecan-3$^+$, and in addition expresses at least one of the genes set forth in SEQ ID NOs:1-4 significantly stronger, preferably 2-fold or 3-fold stronger, compared to a resting macrophage (M0) as measured by quantitative RT-PCR. Stated differently, an Mreg cell is provided that expresses any of the surface marker patterns (1)-(64), more preferably CD16$^+$, CD163$^+$, Syndecan-3+, and in addition expresses at least one of the genes set forth in SEQ ID NOs:1-4 at least by 50%, at least by 100%, at least by 200%, at least by 300%, at least by 400%, at least by 500%, at least by 600%, at least by 700%, or at least by 800% stronger compared to a resting macrophage (M0) as measured by quantitative RT-PCR.

Transcriptomic analysis moreover revealed several genes which can be used for distinguishing Mreg-sc cells from other Mreg cells, such as Mreg-bc cells. These genes include the SELENOP gene (selenoprotein P-NCBI Reference Sequence: NM_005410.4—SEQ ID NO:5), the RNASE1 (ribonuclease A family member 1-NCBI Reference Sequence: NM_002933.5—SEQ ID NO:6), the C1QC gene (complement C1q C chain-NCBI Reference Sequence: NM_172369.5—SEQ ID NO:7), and the NRA4A3 (nuclear receptor subfamily 4 group A member 3-NCBI Reference Sequence: NM_006981.4—SEQ ID NO:8). While the genes SELENOP, RNASE1 and C1QC gene are expressed stronger expressed in Mreg-sc cells compared to Mreg-bc cells, the gene NRA4A3 is downregulated in Mreg-sc. Accordingly, in another preferred embodiment a Mreg cell is provided that expresses at least one of the genes set forth in SEQ ID NOs:5-7 significantly stronger, preferably 2-fold or 3-fold stronger, compared to other types of Mreg cells, such as Mreg-bc cells, as measured by quantitative RT-PCR. Stated differently, an Mreg cell is provided that expresses at least one of the genes set forth in SEQ ID NOs:5-7 at least by 50%, at least by 100%, at least by 200%, at least by 300%, at least by 400%, at least by 500%, at least by 600%, at least by 700%, or at least by 800% stronger compared to other types of Mreg cells, such as Mreg-bc cells, as measured by quantitative RT-PCR.

In yet another preferred embodiment a Mreg cell is provided that expresses the gene set forth in SEQ ID NO:8 to a significantly lower level, preferably 2-fold or 3-fold lower, compared to other types of Mreg cells, such as Mreg-bc cells, as measured by quantitative RT-PCR. Stated differently, an Mreg cell is provided that expresses the gene set forth in SEQ ID NO:8 at least by 50%, at least by 100%, at least by 200%, or at least by 300%, at least by 400%, at least by 500%, at least by 600%, at least by 700%, or at least by 800% lower compared to other types of Mreg cells, such as Mreg-bc cells, as measured by quantitative RT-PCR.

The Mreg-sc cells are particularly suitable for being used for therapeutic purposes, as explained in more detail below. In concept, Mreg-sc therapy is a gain-of-function therapy meaning that administration of Mreg-sc cells with immunosuppressive, anti-inflammatory or tissue-reparative functions will complement a deficiency of those cellular functions in the recipient. By applying suitably large doses, it will be possible to restore or exceed said activities in the recipient. In transplant and autoimmune models, Mreg-sc treatment has a therapeutic effect that persists beyond their own lifespan in the recipient. This enduring effect can be explained by the impact of Mreg-sc treatment upon the recipient T cells. Administration of Mreg-sc cells may influence recipient T cell responses in three complementary ways.
- (a) Mreg-sc cells directly interact with recipient T cells which results in specific T cell deletion or conversion into activated induced regulatory T cells (iTregs).
- (b) Mreg-sc cells alter the behaviour of recipient dendritic cells through direct interaction or release of anti-inflammatory mediators. One important function of Mreg-sc cells may be to die in a suitably self-conditioned environment and give-up antigens to recipient dendritic cells which in turn specifically suppress recipient T cells.
- (c) Mreg-sc cells or sub-cellular fractions thereof exert active or passive non-specific suppressive through the release of soluble mediators that may act directly or exert effects through recipient myelomonocytic cells.

In a third aspect, the invention refers to a pharmaceutical composition comprising the Mreg-sc cell of the second aspect of the invention or a sub-cellular fraction thereof. The pharmaceutical composition will comprise, as a first component, an effective amount of the Mreg-sc cells of the invention or a sub-cellular fraction thereof. As used herein, an effective amount of the Mreg-sc cells to be administered intravenously to the patient will be in the range of about $1\times10^4$ to about $1\times10^8$/kg body weight, preferably between about $1\times10^5$ and about $1\times10^7$/kg body weight, and more preferably between about $1\times10^6$ and about $9\times10^6$/kg body weight, such as about $1\times10^6$/kg, about $2\times10^6$/kg, about $3\times10^6$/kg, about $4\times10^6$/kg, about $5\times10^6$/kg, about $6\times10^6$/kg, about $7\times10^6$/kg, or about $8\times10^6$/kg body weight of the patient to be treated. Similarly, where the invention comprises the administration of sub-cellular fractions of the Mreg-sc cells of the invention, these fractions will be prepared based on an amount of cells that corresponds to one of the ranges mentioned above in connection with the administration of cells. As used herein, a sub-cellular fraction of the Mreg-sc cell may include necrotic cell particles, apoptotic cell particles, or exo-somes that include the cell's major histocompatibility (MHC) molecules. Cell lysates prepared by treating cells with hypoosmotic solutions, dissolution using detergents or acids, freeze-thawing or heating, sonication, irradiation, mechanical disruption or prolonged storage may also be used. Sub-cellular fractions may also include cell extracts containing total cellular protein, membrane proteins, cytoplasmic proteins or purified MHC molecules. Where the pharmaceutical composition is formulated for local administration, e.g. intradermal application, the amount of cells will be different.

Apart from the cells or sub-cellular fractions of the cells, the pharmaceutical composition can comprise further excipients, such as buffers, pH regulating agents, preservatives, and the like. The nature and amounts of the excipients included in the pharmaceutical composition of the invention will depend on the intended route of administration. Generally, different routes of administration are feasible for providing the Mreg-sc cells of the invention or sub-cellular fractions thereof to a patient in need of treatment. Preferably, the pharmaceutical composition of the invention will be formulated for parenteral administration, such as subcutaneous, intramuscular, intravenous or intradermal administration. It is particularly preferred that the Mreg-sc cells or sub-cellular fractions thereof or a composition comprising said cells or fractions are administered to the patient by intravenous administration.

The formulation of the Mreg-sc cells of the invention or their sub-cellular fractions into pharmaceutical compositions can be achieved by applying routine methods known in the field of drug formulation. Suitable methods are described, for example, in standard textbooks. Pharmaceutical compositions suitable for intravenous administration by injection or infusion normally include sterile aqueous solutions or suspensions and sterile powders for the extemporaneous preparation of sterile solutions or suspensions. The composition intended for injection must be sterile and should be fluid in order to allow a convenient handling in a syringe or infusion bag.

The composition should be stable under the conditions of administration and is preferably pre-served against the contaminating action of microorganisms such as bacteria and fungi, for example, by including parabens, chlorobutanol, phenol, ascorbic acid, thimerosal, and the like into the composition. For intravenous administration, suitable carriers may comprise physiological saline, bacteriostatic water, Cremophor EL™ (BASF) or phosphate buffered saline (PBS). The carrier may also be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Sterile injectable solutions can be prepared by incorporating the cells or sub-cellular fractions in the required amount in an appropriate solvent with one or more of the above mentioned ingredients followed by sterile filtration. Generally, suspensions are prepared by incorporating the active compound, i.e. the cells or sub-cellular fractions thereof, into a sterile vehicle that contains a basic dispersion medium and the required other ingredients from those mentioned above. In case of sterile powders for the preparation of sterile injectable solutions, methods of preparation are vacuum drying and freeze-drying that yields a powder of the cells or sub-cellular fractions thereof plus any additional desired ingredient from a previously sterile-filtered solution thereof.

The composition intended for infusion or injection will have a volume of between 50 and 500 ml, wherein a volume of between 90 ml and 250 ml is particularly preferred, and wherein a volume of between 90 ml and 150 ml is even more preferred. For local administration, e.g. intradermal administration, the volume per injection will be in the range of 0.1-1.0 ml.

The Mreg-sc cells can be administered to a patient in need of treatment by different administration regimens. For example, where the cells or cell fractions are administered to the patient by intravenous infusion, the total amount of Mreg-sc cells or Mreg-sc cell fractions to be administered can be supplied by one or more than one infusion. In a preferred embodiment, the Mreg-sc cells or cell fractions are supplied to the patient through an infusion set with a 200 m filter. The suspension comprising the Mreg-sc cells or Mreg-sc cell fractions may be primed with 0.9% NaCl. The suspension may be given in a single infusion, more preferably a short-term infusion within less than 60 min, e.g. within 60 min, 30 min, 20 min or 15 min. Preferably a central venous catheter is used for administering the Mreg-sc suspension.

The administration of the Mreg-sc cells or cell fractions can be accompanied by the preceding, simultaneous or subsequent administration of other active agents. For example, where the Mreg-sc cells or cell fractions of the invention are administered to prevent an immune response in a patient receiving an organ transplant, an immunosuppressive drug may be administered together with the cells or cell fractions of the invention. Immunosuppressive drugs that are routinely used in the field of transplantation medicine comprise, but are not limited to, cyclosporin A (CSA), tacroli-mus, azathioprine (AZA), mycophenolate mofetil, rapamycin, and steroids (STE). Generally, the presence of immunosuppressive drugs in the recipient blood does not affect the effectiveness of the cells or cell fractions of the invention.

Although the Mreg-sc cells obtained from the method described in the first aspect of the invention exhibit a stable phenotype, it is recommended for safety reasons that the Mreg-sc cells or sub-cellular fractions obtained there from are administered within 24 hours after harvesting them from the cell cultures. Preferably, the cells are administered within 20 hours, within 16 hours, within 12 hours, within 8 hours, or within 4 hours after harvesting the cells from the cultures.

In a fourth aspect, the invention refers to the therapeutic application of Mreg-sc cells according to the second aspect of the invention or sub-cellular fractions thereof or compositions according to the third aspect of the invention. As indicated elsewhere herein, the Mreg-sc cells provided by the present invention exhibit a number of pharmacological properties, such as immunosuppressive, immunoregulatory, angiogenic and anti-inflammatory properties, which make them highly suitable for being used in immunosuppressive, anti-inflammatory or tissue-reparative therapies. For example, the artificially induced Mreg-sc cells of the invention are T cell-suppressive and mediate an active deletion of activated T cells. As such, the cells are highly suitable for use as an adjunct immunosuppressive therapy in a variety of immunologically-mediated diseases, such as organ transplantation.

Accordingly, in one embodiment of the invention, an Mreg-sc cell according to the second aspect of the invention or a sub-cellular fraction thereof or a pharmaceutical composition according to the third aspect of the invention is used in a method of suppressing transplant rejection and/or prolonging transplant survival in a subject receiving a transplant. The invention thus refers to a method of suppressing transplant rejection and/or prolonging transplant survival in a subject receiving a transplant, comprising (i) the administration of an effective amount of an Mreg-sc cell according to the second aspect of the invention or a sub-cellular fraction thereof, or (ii) the administration of a pharmaceutical composition according to the third aspect of the invention. Preferably, the transplant is an organ, tissue or cell transplant. The type of organ to be transplanted is not limited according to the invention, but it will preferably be a kidney, liver, heart, lung, or pancreas. It is particularly preferred that the organ to be transplanted to the recipient is a human organ.

The Mreg-sc of the present invention can also be used for suppressing transplant rejection and/or prolonging transplant survival in cases where the transplant is a tissue transplant rather than an organ transplant. Again, the tissue to be transplanted into the recipient is not particularly limited. The rejection of any tissue that was derived from an allogeneic donor in the recipient can be prevented or ameliorated by the Mreg-sc of the present invention. The tissue to be transplanted will preferably be a human tissue, such as an intestinal, cornea, skin, composite tissue, bone marrow, or pancreatic islet tissue.

The Mreg-sc prepared according to the method of the invention can also support cell transplant into a recipient by suppression of the immune response in the recipient. Where the transplant is a cell transplant, the nature of the cell to be transplanted is generally not limited, but it is preferred that the cell to be transplanted is selected from the group consisting of an adult stem cell transplant, an isolated hepatocyte transplant or a leukocyte cell transplant. In a preferred embodiment of this invention, Mreg-sc cells are used to facilitate engraftment of haematopoietic stem cells (HSC) after bone marrow or HSC transplantation.

To suppress transplant rejection in the recipient and induce acceptance of an allogeneic organ, tissue or cell transplant, the Mreg-sc cells of the invention or a pharmaceutical composition comprising the Mreg-sc cells or a sub-cellular fraction thereof can be administered intravenously by injection or infusion, as described above. The injection or infusion can be given either pre-operatively or post-operatively. If the Mreg-sc cells are administered pre-operatively, they will be administered to the recipient at least one time, preferably two times, and more preferably three times before the operation. It is preferred that the Mreg-sc are administered to the recipient not earlier than one week before operation, e.g. 6 days, 5 days, 4 days, 3 days, 2 days, or 1 day before operation. If the Mreg-sc cells are administered post-operatively, a first administration will be given preferably within 24 hours after operation, more preferably within 36 hours, 48 hours, 60 hours, or 72 hours after operation. Alternatively, in stably immunosuppressed transplant recipients, Mreg-sc therapy may be administered at any time after transplantation. Alternatively, Mreg-sc may be administered to transplant recipients undergoing acute or chronic transplant rejection. The Mregs-sc are then capable of repelling the T-cell response of the recipient's immune system against the transplant and to persist in the recipient's body (especially spleen, liver, lungs and bone marrow) for a sufficiently long period of time to confer long-term transplant acceptance to the recipient.

When using the Mreg-sc of the invention for suppressing transplant rejection or prolonging transplant survival in a subject receiving a transplant, the transplant will normally be an allogeneic transplant, i.e. a transplant which originates from a donor that, although genetically different, belongs to the same species as the recipient. In this case, the Mreg-sc cells are generated based on blood monocytes that were obtained from said donor. The monocytes can be obtained from a living donor or a dead donor. In case of a dead donor, i.e. a body donation, the body of the donor is normally flushed with a perfusion medium by canalisation of the principal artery for the purpose of organ preservation. The venous blood is removed from the body and can be collected for preparing the Mreg-sc according to the method described herein. Alternatively, Mreg-sc can also be prepared from myelomononuclear cells that are isolated from the donor's spleen. In the case of post-operative application of the Mreg-sc cells that were prepared from a deceased donor, a rejection of the transplanted organ can be prevented by the administration of immunosuppressants which are routinely used for this purpose during organ transplantation.

In another embodiment, the Mreg-sc cells according to the second aspect of the invention or a sub-cellular fraction thereof or a pharmaceutical composition according to the third aspect of the invention is used in a method of promoting or sustaining the engraftment or effect of regulatory T cell cell-based medicinal products. The invention thus also refers to a method of promoting or sustaining the engraftment or effect of regulatory T cell cell-based medicinal products in a subject comprising (i) the administration of an effective amount of an Mreg-sc cell according to the second aspect of the invention or a sub-cellular fraction thereof, or (ii) the administration of a pharmaceutical composition according to the third aspect of the invention.

Apart from the immunoregulatory and immunosuppressive properties, the Mreg-sc cells of the invention have anti-inflammatory properties which allow for the abrogation of chronic inflammatory immune processes. Accordingly, the Mreg-sc cells provided herein are also useful for treating diseases or disorders that are characterized by a deregulated immune status or an excessive inflammatory reaction, in particular chronic inflammatory diseases. Such diseases or disorders include, for example, autoimmune diseases, inflammatory diseases and hypersensitivity reactions.

Thus, in yet another embodiment, the Mreg-sc cell according to the second aspect of the invention or a sub-cellular fraction thereof or pharmaceutical composition according to the third aspect of the invention is used in a method of treating or preventing an autoimmune disease, an inflammatory disease, or a hypersensitivity reaction.

Where the Mreg-sc cells are used for treating an autoimmune disease, said disease may be (a) principally T cell-mediated, (b) principally antibody-mediated or (c) principally mediated by other cellular components of the immune system. The disease may be a local or systemic autoimmune condition. The type of autoimmune conditions to be treated with the Mreg-sc therapy is not limited according to the invention, and includes systemic lupus erythematosus (SLE), scleroderma, Sjögren's syndrome, polymyositis, dermatomyositis, and other systemic autoimmune conditions; rheumatoid arthritis (RA), juvenile rheumatoid arthritis, and other inflammatory arthritides; ulcerative colitis, Crohn's disease, and other inflammatory bowel diseases; autoimmune hepatitis, primary biliary cirrhosis, and other autoimmune liver diseases; cutaneous small-vessel vasculitis, granulomatosis with polyangiitis, eosinophilic granulomatosis with polyangiitis, Behget's disease, thromboangiitis obliterans, Kawasaki disease, and other large-, medium- or small-vessel vasculitides of autoimmune aetiology; Multiple sclerosis (MS) and neuroimmunological disorders; Type I diabetes, autoimmune thyroid dysfunction, autoimmune pituitary dysfunction, and other autoimmune endocrinological disorders; haemolytic anaemia, thrombocytopaenic purpura and other autoimmune disorders of the blood and bone marrow; psoriasis, pemphigus vulgaris, pemphigoid and other autoimmune dermatological conditions.

The Mreg-sc cells are also effective for treating acute or chronic inflammatory diseases, and diseases with a pathophysiologically significant inflammatory component. The inflammatory disease to be treated may be local or systemic. The type of inflammatory diseases or condition that benefit from treatment with Mreg-sc is not limited and includes, but is not limited to arterial occlusive diseases, such as peripheral artery occlusive disease (pAOD), critical limb ischaemia, arteriosclerosis, cerebral infarction, myocardial infarction, renal infarction, intestinal infarction, angina pectoris, and other conditions caused by arterial occlusion or constriction; microvascular angina, also known as cardiac syndrome X; inflammation associated systemic with metabolic disorders, including Type II diabetes and obesity-related metabolic syndrome; dermatological diseases, including eczema. Preferably, the inflammatory disease to be treated is characterized by chronic inflammation of the intima of an arterial wall, e.g. myocardial infarction, stroke, critical limb ischemia vasculitis and pAOD.

Where the treatment of a hypersensitivity reaction is desired, the hypersensitivity reaction is preferably selected from the group of asthma, eczema, allergic rhinitis, angioedema, drug hypersensitivity, and mastocytosis.

The cells may also be useful for treating pAOD. It is known that pAOD in patients who are unfit for revascularisation procedures, owing either to the extent or location of their arterial occlusions, or to significant co-morbidities, is a severely debilitating and prevalent condition for which amputation is the only therapeutic option. Amputation remains a treatment of last resort and is associated with relatively high mortality, and only a minority of patients subsequently recover full mobility. The Mreg-sc cells obtained from the method described herein, as their counterparts described in the prior art, may actively promote neovascularisation, i.e. the formation of new blood vessels, through the basal and stimulated expression of pro-angiogenic growth factors, such as VEGF, FIGF (VEGF-D), PDGFB and MDK.

In one embodiment, Mreg-sc cells are injected intramuscularly or subcutaneously into an ischaemic limb. In the ischaemic tissue, Mreg-sc cells will inevitably be exposed to microbial components and necrotic tissue components (e.g. HMGB1) that act as TLR4 agonists. Hence, Mreg-sc can be used to promote tissue regeneration through local secretion of pro-angiogenic growth factors. In another embodiment, Mreg-sc cells may be stimulated ex vivo with TLR ligands during the manufacturing process to ensure their high-level production of pro-angiogenic growth factors.

Said TLR ligands may include, but are not limited to, lipopolysaccharide (LPS) or monophosphoryl lipid A (MPLA). The pAOD to be treated with the Mreg-sc of the invention may be a pAOD of any grade or category. For example, the pAOD may be a pAOD of grade I, categories 1-4, or grade II-IV pAOD.

The Mreg-sc cells prepared in accordance with the method of the invention can also be used for treating leg ulcers, in particular chronic leg ulcers. More specifically, the cells can be used for treating micro- and macroangiopathies of the lower limbs in a subject. As used herein, a microangiopathy is a blood vessel disease which affects small blood vessels and capillaries in the body, such as small cerebral vessels, small coronary vessels or small vessels in the legs. During microangiopathy, the capillary basement membrane becomes thick and hard which causes obstruction or rupture of capillaries or small arteries which in turn results in tissue necrosis and loss of function. In contrast, a macroangiopathy is a blood vessel disease that affects large blood vessels, such as the arteries. Obstruction of the larger arteries leads to high incidence of heart attacks, strokes and peripheral vascular disease in diabetics. Obstruction of the arteries in the leg often results in ulcers on the feet and legs that slowly heal. Peripheral vascular disease also causes intermittent claudication, i.e. pain during walking, which severely impairs mobility. In a lot of cases, macroangiopathies required amputation of one or both legs, in particular in diabetic patients.

One cause of micro- and macroangiopathies is long-term diabetes mellitus. In diabetic patients, high blood glucose levels cause the endothelial cells of the blood vessels to absorb more glucose than normal. These cells then form more glycoproteins on their surface than normal, and also cause the basement membrane in the vessel wall to grow abnormally thicker and weaker. As a result, the vessel walls become leaky and slow the flow of blood through the body such that some tissues do not receive sufficient oxygen an are damaged.

According to the invention, the microangiopathy to be treated is preferably selected from the group of diseases consisting of angiitis, arteritis, angiodysplasia, atrophy blanche, dermatosclero-sis, Determann syndrome, diabetic angiopathy, endangiitis obliterans, erythromelalgia, fibromus-cular dysplasia, malum perforans, Monckeberg Sclerosis, Osler's disease, compartment syndrome, Paget-von-Schroetter syndrome, Raynaud's syndrome, and leg ulcers. In a particularly preferred aspect, the micro- or macroangiopathies which are to be treated according to the invention are leg ulcers. As used herein, leg ulcers include diabetic leg ulcers and venous leg ulcers.

According to the invention, the macroangiopathy to be treated is preferably selected from the group of aneurysm, dissection, atherosclerosis, atherothrombosis, peripheral arterial occlusive disease (PAD), claudicatio intermittens, necrosis and gangrene, vascular malformation, Leriche syndrome, or compression syndrome.

The administration of the Mreg cells or cell fractions can be accompanied by the preceding, simultaneous or subsequent administration of other active agents. For example, where the Mreg cells or cell fractions are administered to patients suffering from micro- or macroangiopathies, compounds against blood hyperviscosity, such as calcium dobesilate, compounds which exert a capillary stabilizing effect, such as naftazone, or the like can be administered before, simultaneously with or after Mreg administration.

In another aspect, the Mreg-sc cells of the invention can be used for promoting surgical, traumatic or other wound healing in a subject. Mreg therapy may be used to promote healing of acute or chronic wounds, optionally in conjunction with conventional management (i.e. cleaning, closure and dressing). Wounds may be open or closed. Open wounds may include incisions, lacerations, abrasions, avulsions, penetrating injuries or punctures. Closed wounds may include crush injuries or haematomas. Incisions may be traumatic or iatrogenic (i.e. surgical incisions). Mregs may be used to promote engraftment of autologous or allogeneic skin grafts. Mregs may be used in conjunction with conventional management may accelerate healing of burns, which may be caused by exposure of skin to heat, extreme cold, chemicals, friction, radiation or electrical current. The statements made in connection with the treatment of ulcers likewise apply to the treatment of wounds or burns.

As indicated above, the Mreg-sc of the invention may have angiogenic properties, so that their use for treating diseases or conditions that require neovascularisation is contemplated herein. Hence, the invention also relates to the Mreg-sc cell according to the second aspect of the invention or a sub-cellular fraction thereof or pharmaceutical composition according to the third aspect of the invention which is used in a method of inducing angiogenesis or vasculogenesis in hypoxic tissues, promoting tissue-repair processes by participating in tissue remodelling, tissue regeneration, preventing or reducing fibrosis, reducing ischemic pain or avoiding major limb amputation. The invention thus refers to a method of inducing angiogenesis or vasculogenesis in hypoxic tissues, promoting tissue-repair processes by participating in tissue remodelling, tissue regeneration, preventing or reducing fibrosis, reducing ischemic pain or avoiding major limb amputation comprising (i) the administration of an effective amount of an Mreg-sc cell according to the second aspect of the invention or a sub-cellular fraction thereof, or (ii) the administration of a pharmaceutical composition according to the third aspect of the invention.

The treatment of autoimmune diseases, inflammatory diseases, or hypersensitivity reactions can be achieved either with Mreg-sc which are derived from monocytes which are allogeneic to the patient, as described above in the context with transplantation applications, or with monocytes which are autologous to the patient in need of treatment. Where possible, the treatment of autoimmune diseases, inflammatory diseases, or hypersensitivity reactions will be performed with autologous monocytes. For this purpose, the Mregs-sc can be administered intravenously with or without simultaneous local intramuscular injections.

In yet another embodiment, the Mreg-sc cell according to the second aspect of the invention or a sub-cellular fraction thereof or pharmaceutical composition according to the third aspect of the invention is used as a vehicle to deliver gene therapy. The invention thus refers to a method of delivering gene therapy comprising (i) the administration of an effective amount of an Mreg-sc according to the second aspect of the invention which comprises a transgene, or (ii) the administration of a pharmaceutical composition comprising an Mreg-sc cell according to the second aspect of the invention which comprises a transgene.

According to a fifth aspect, the invention refers to a process for preparing a sub-cellular fraction of an immunoregulatory macrophage cell, said process comprising:
(a) providing an immunoregulatory macrophage as described in the context of the first aspect of the invention,
(b) decomposing the immunoregulatory macrophage cell to provide a sub-cellular fraction,
(c) obtaining the sub-cellular fraction.

The Mreg-sc cells of the invention can be decomposed according to conventional methods. For example, the Mreg-sc cells can be lysed by treating the cells with hypoosmotic solutions, detergents or acids. Alternatively the cells can be decomposed by freeze-thawing or heating, sonication, irradiation, mechanical disruption or prolonged storage. In the last step of the method, the sub-cellular fraction of the cells is obtained, such as a whole protein fraction, a membrane protein fraction, a cytoplasmic protein fraction. These fractions can be used for the above described therapeutic purposes instead of viable Mreg-sc cells. Alternatively, the factions can be further purified to isolate certain proteins, such as MHC proteins.

According to a sixth aspect, the invention refers to a process for preparing an immunoregulatory T cell, said process comprising:
(a) obtaining T cells of a subject;
(b) co-culturing the T cells with Mreg-sc cells as defined above, i.e. Mreg cells derived from suspension culture, or a sub-cellular fraction thereof;
(c) obtaining the immunoregulatory T cells from the culture medium.

As described elsewhere herein, T cells that have been co-cultured with Mregs-sc inhibit T cell proliferation. Accordingly, the immunoregulatory T cells obtained from the above methods can be used, either alone or in combination with the Mreg-sc cells of the invention, for the treatment of any of the diseases or disorders discussed elsewhere herein. In a first step, T cells from a blood sample of a subject are obtained. The cells can be obtained, e.g. from a blood sample or apheresate, or from the subject's tissue, e.g. from bone marrow or the spleen. The cells can be obtained by conventional methods, e.g. in case of cells from the blood by venepuncture. The T cells used in the above method will be, for example, CD3+ T cells or subsets thereof. Before being co-cultured with the Mreg-sc cells, the CD3+ T cells can be purified or enriched by conventional methods, e.g. by magnetic microbead separation or flow cytometry sorting.

The T cells are then contacted with Mregs-sc of the present invention. The cells can be contacted in different Mreg:Treg ratios. For example, the cell fractions can be contacted in a Mreg:Treg ratio of between 1:5 to 5:1, preferably between 1:2 to 2:1. More preferably, Mreg:Treg ratio is about 1:1. Different media can be used for the co-culturing method. The media can be those described above in connection with the method for preparing Mreg-sc cells. In a preferred embodiment the medium is X-vivo 10 from Lonza. The medium may contain further additives such as M-CSF and/or GM-CSF, preferably human recombinant M-CSF and/or GM-CSF. The amount of M-CSF and/or GM-CSF will be in the range mentioned elsewhere herein, e.g. 5-100 ng/ml, preferably 20-25 ng/ml. The medium may also contain other additives, such as Glutamax in an amount of 1-5 mM, preferably 2 mM.

The cells will be co-cultured for 1-8 days, preferably for at least 3 days, at least 4 days, or at least 5 days. After the pre-determined culturing period, the T cells can be re-isolated by conventional methods, e.g. by enriching the cells for $CD4^+CD25^+$ $TIGIT^+$ $FoxP3^+$ Tregs. If necessary, the cells can be further formulated to pharmaceutical products.

EXAMPLES

Figure 1:
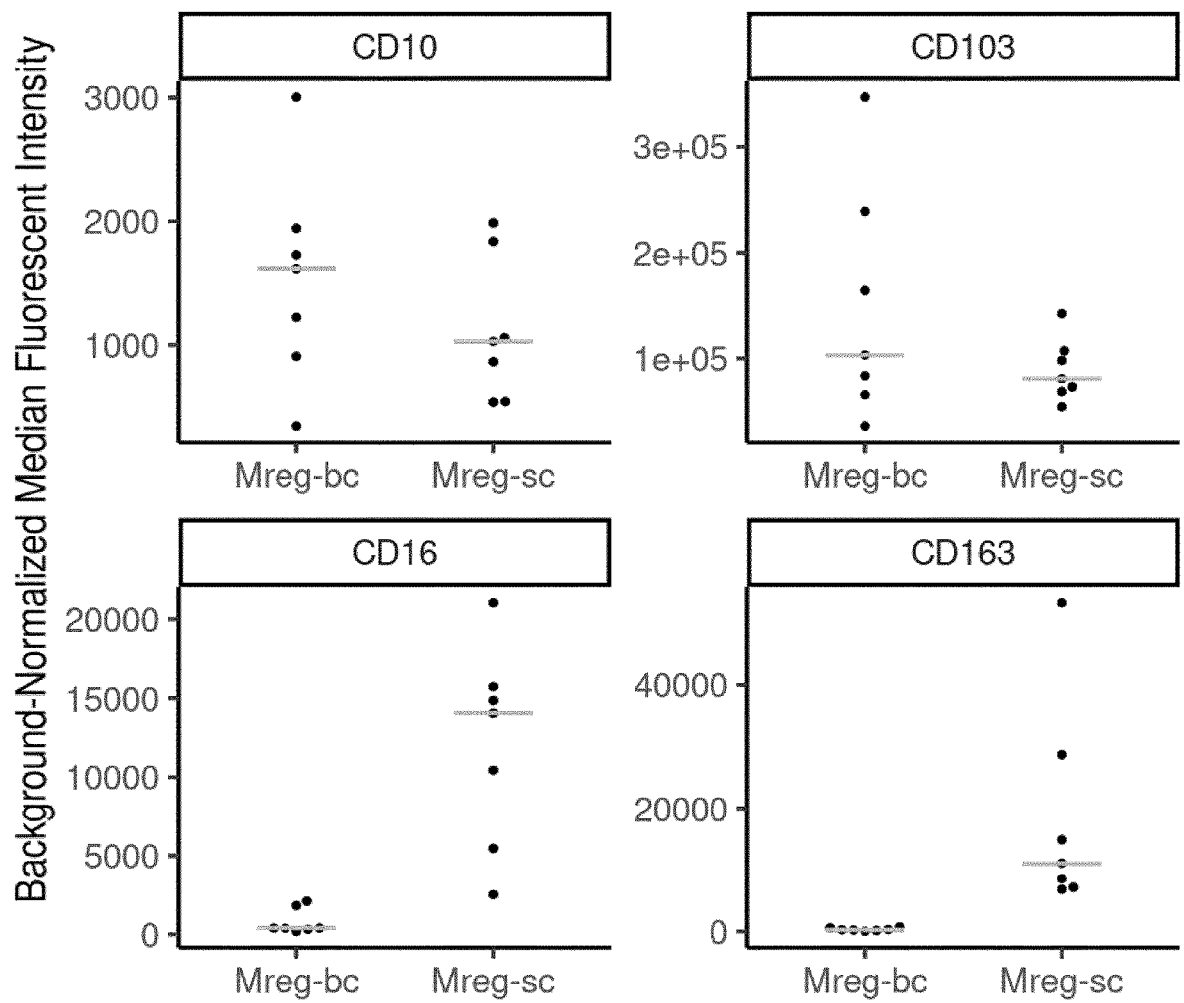
FIG. 1 shows a comparison of 23 extracellular marker expressions on Mreg-sc and Mreg-bc cells. (A) Background normalized median fluorescence intensities of each marker are shown in dot blots where each dot represents one batch, i.e. donor. (B) In waterfall plot, with bars repre-senting log-scale fold changes in the channel-normalized Median Fluorescent Intensity (nMFI). nMFI was calculated in R v3.5 by grouping assays and channels, then subtracting the FMO MFI measurement that occurred within that group. (C) 10 EC markers were differently expressed in the two different Mreg products to a statistically significant degree. (D) A representative figure of the gating strategy for macrophage phenotyping. For intracellular analyses, CD45 was replaced with CD33 and a fixable viability dye for the APC channel was used. Where 7-AAD was used, the gating logic was again similar. To assess the degree of non-target cell contamination, the gates were extended to cover small-sized cells, such as lymphocytes.
Figure 1:
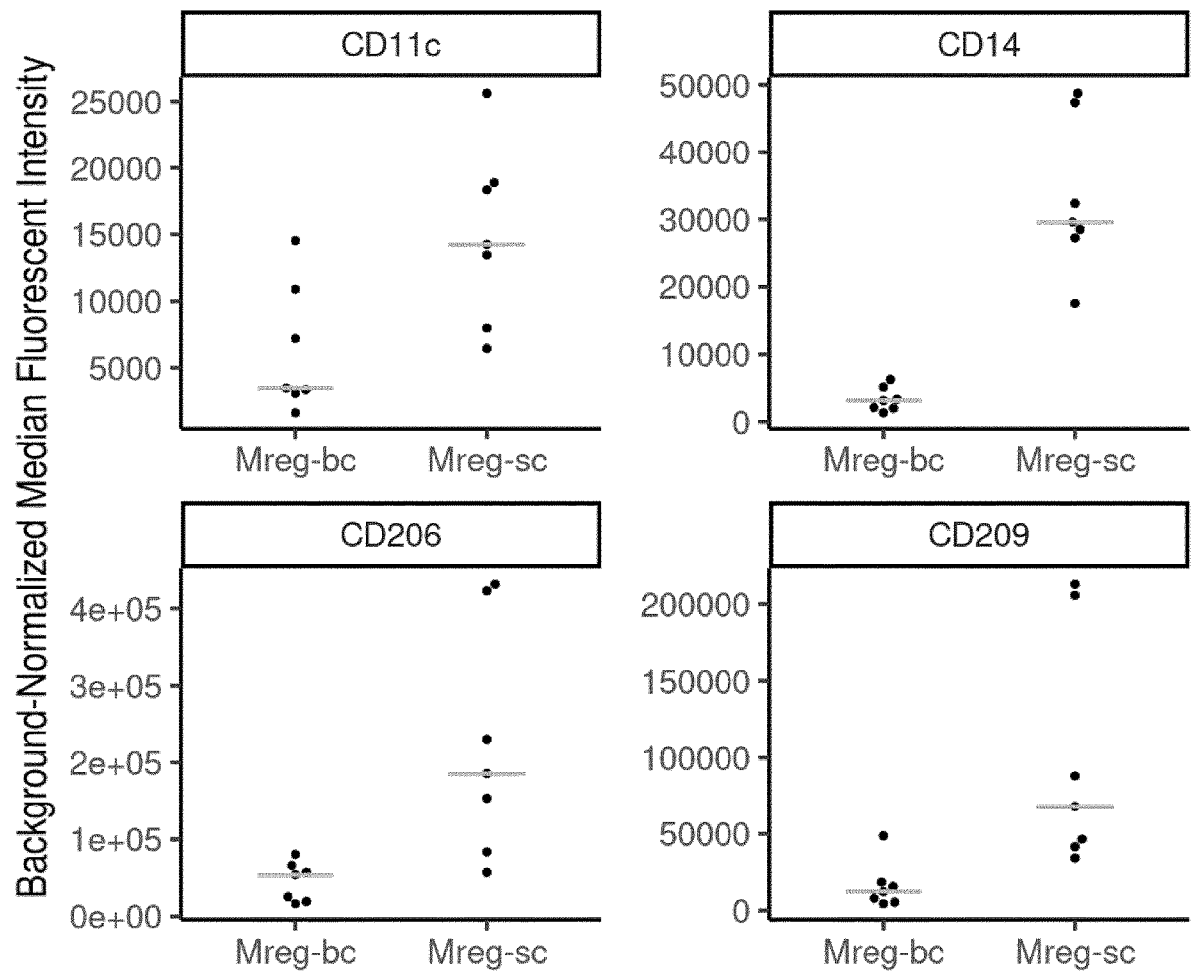
Figure 1:
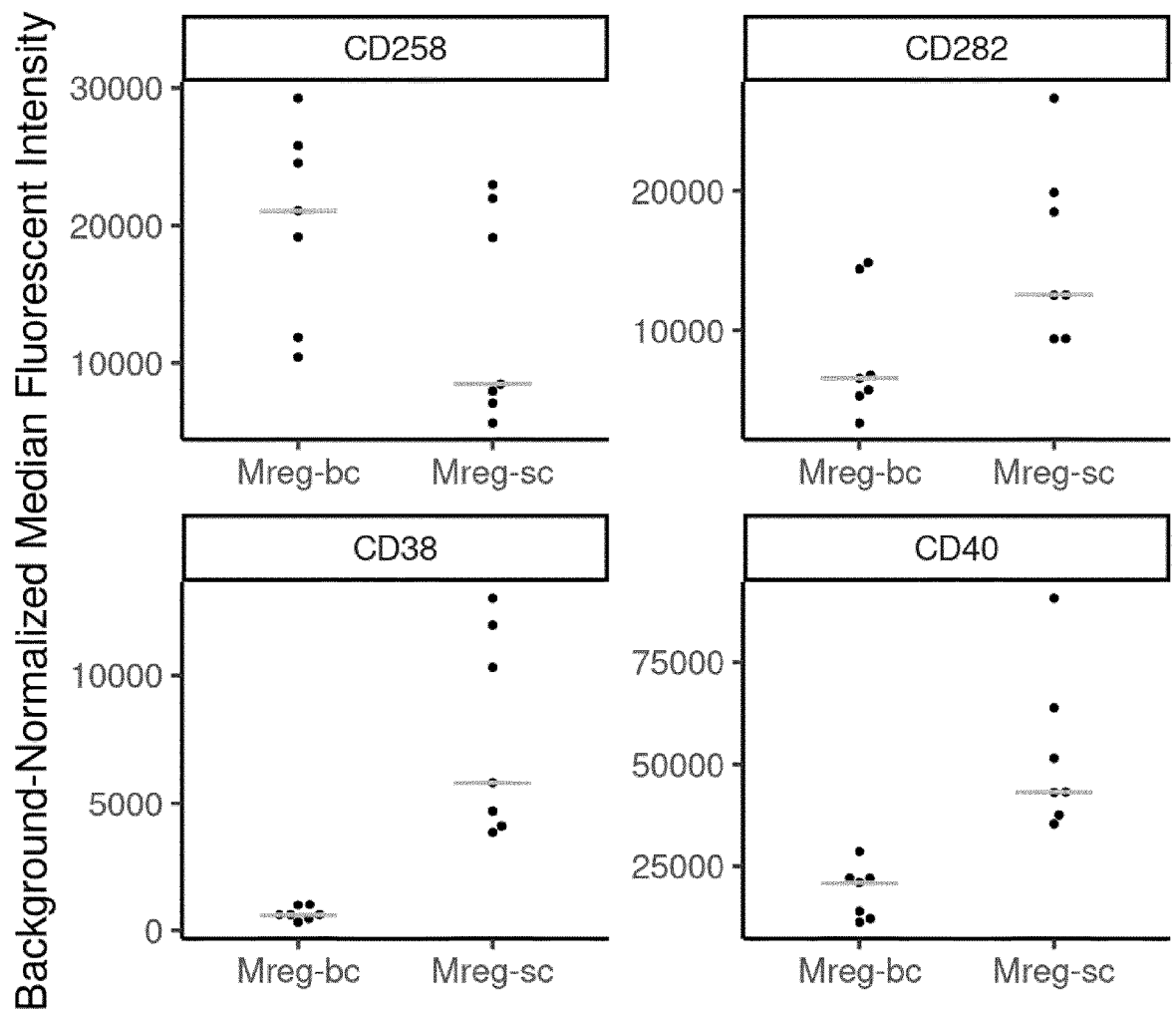
Figure 1:
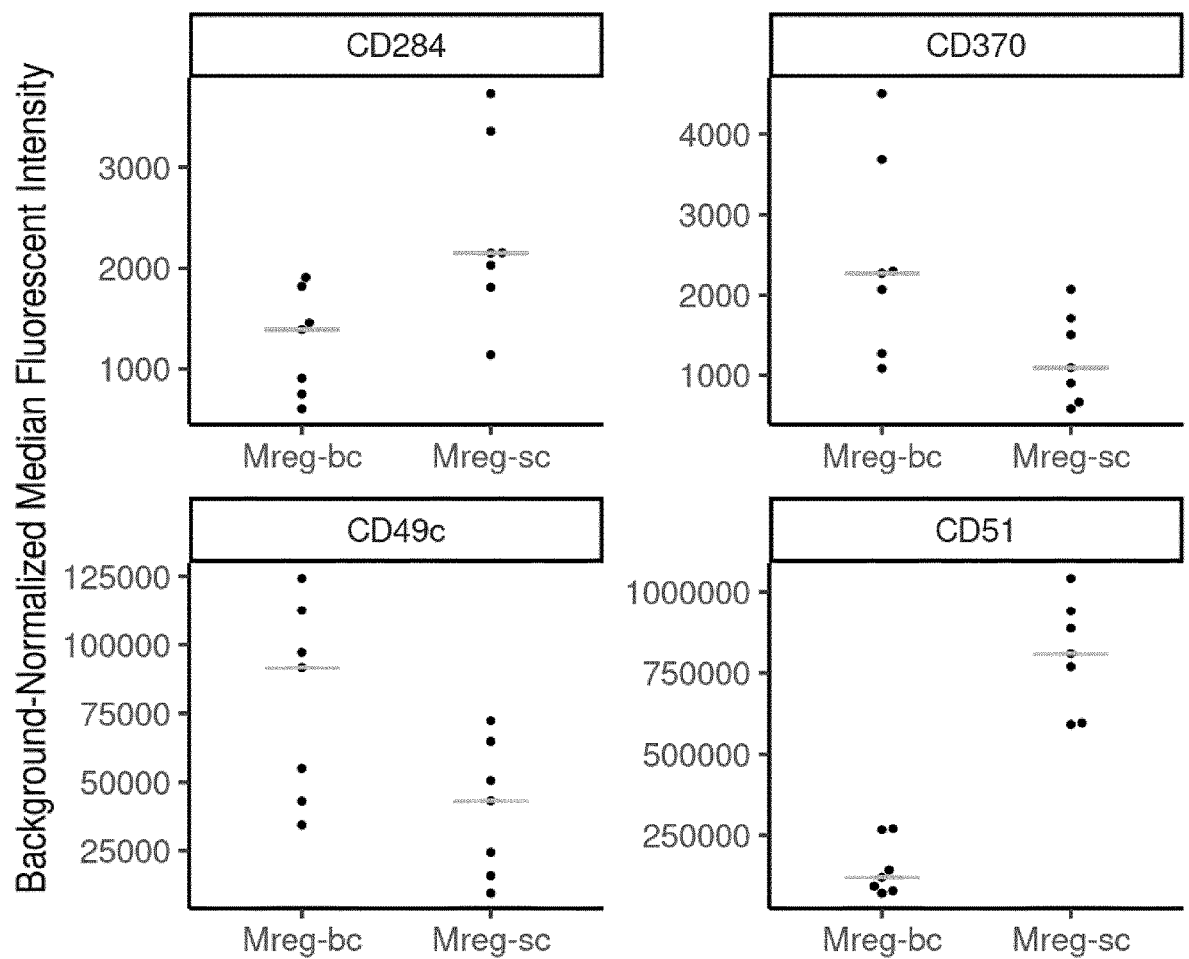
Figure 1:
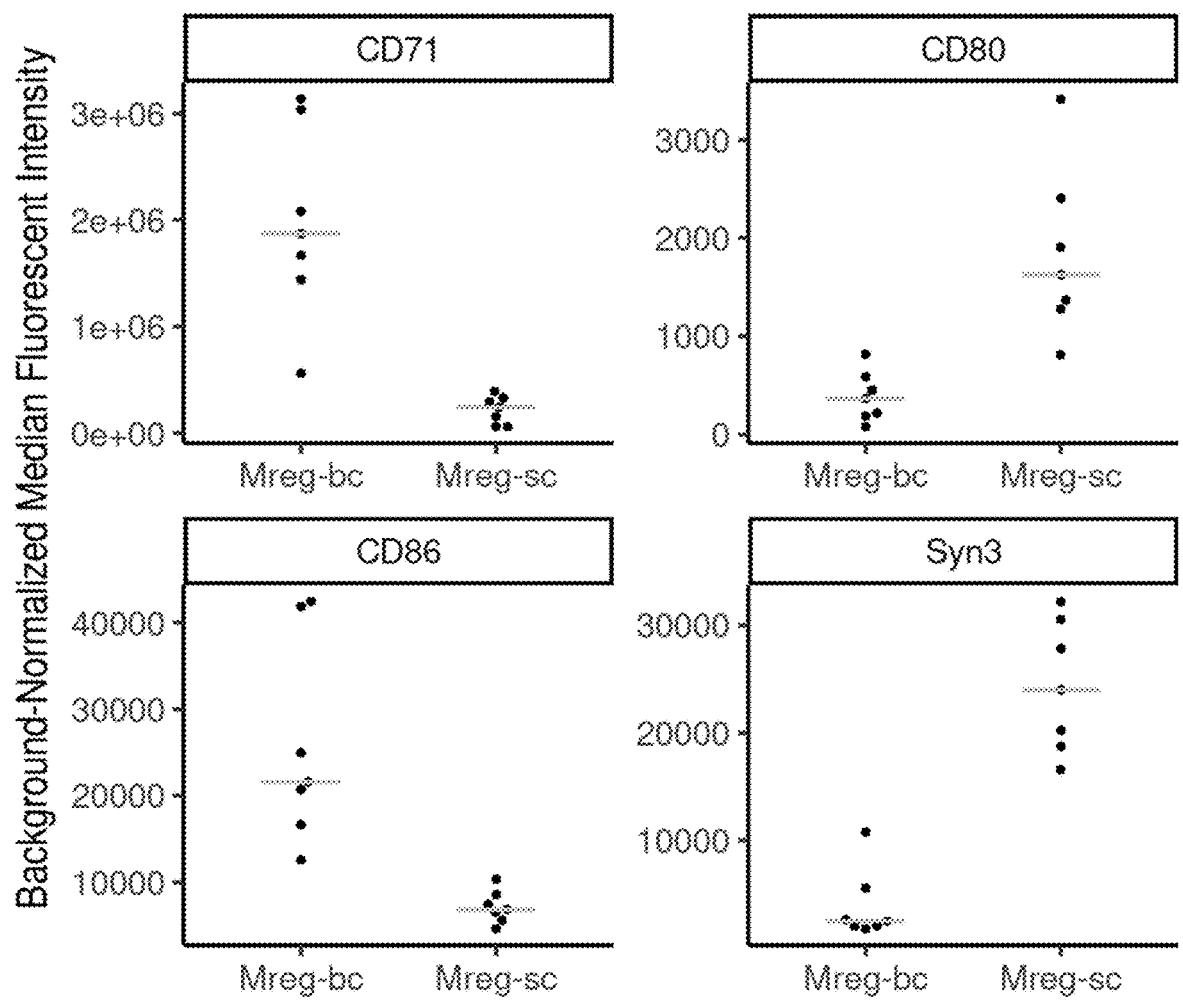
Figure 1:
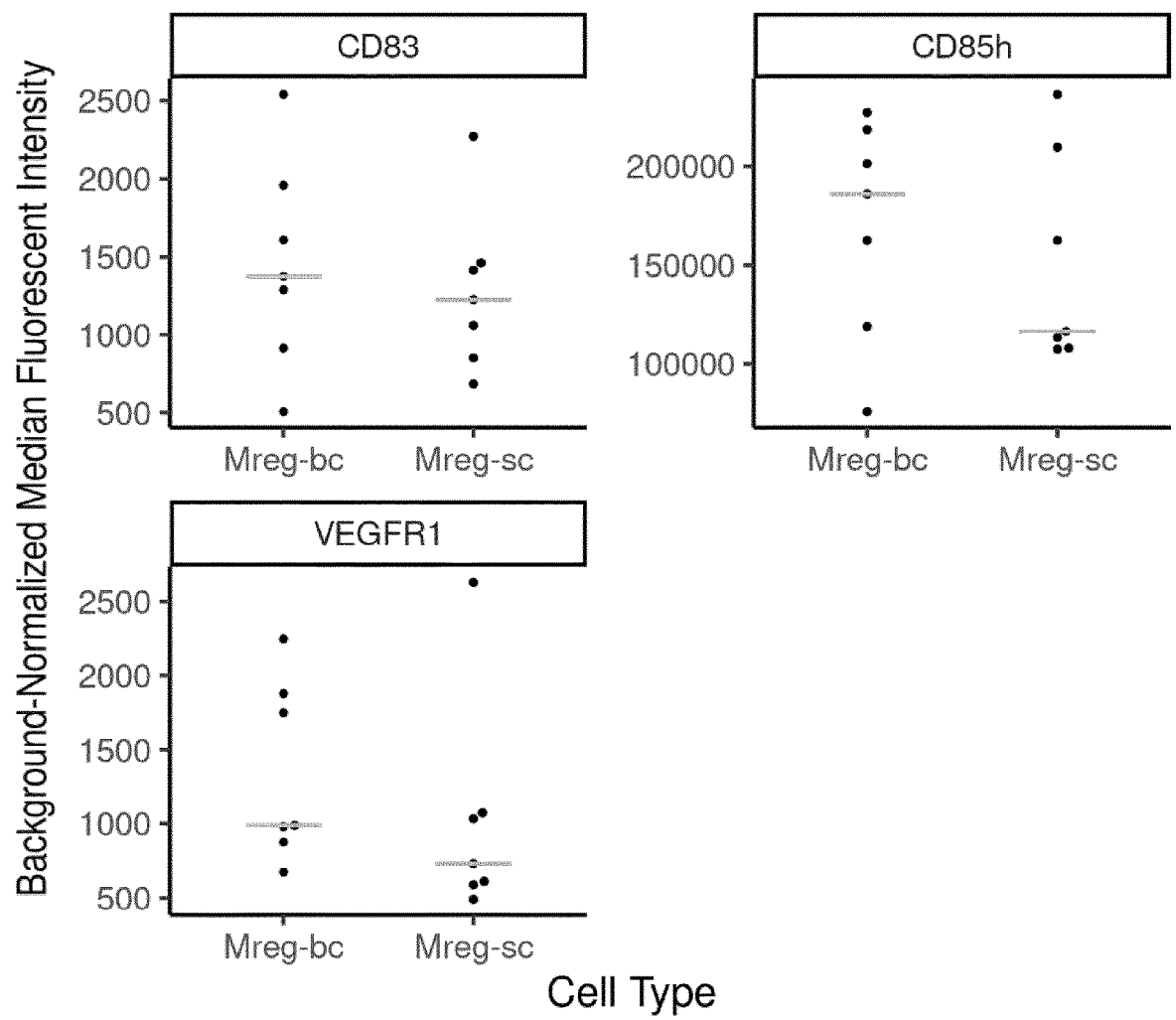
Figure 1B:
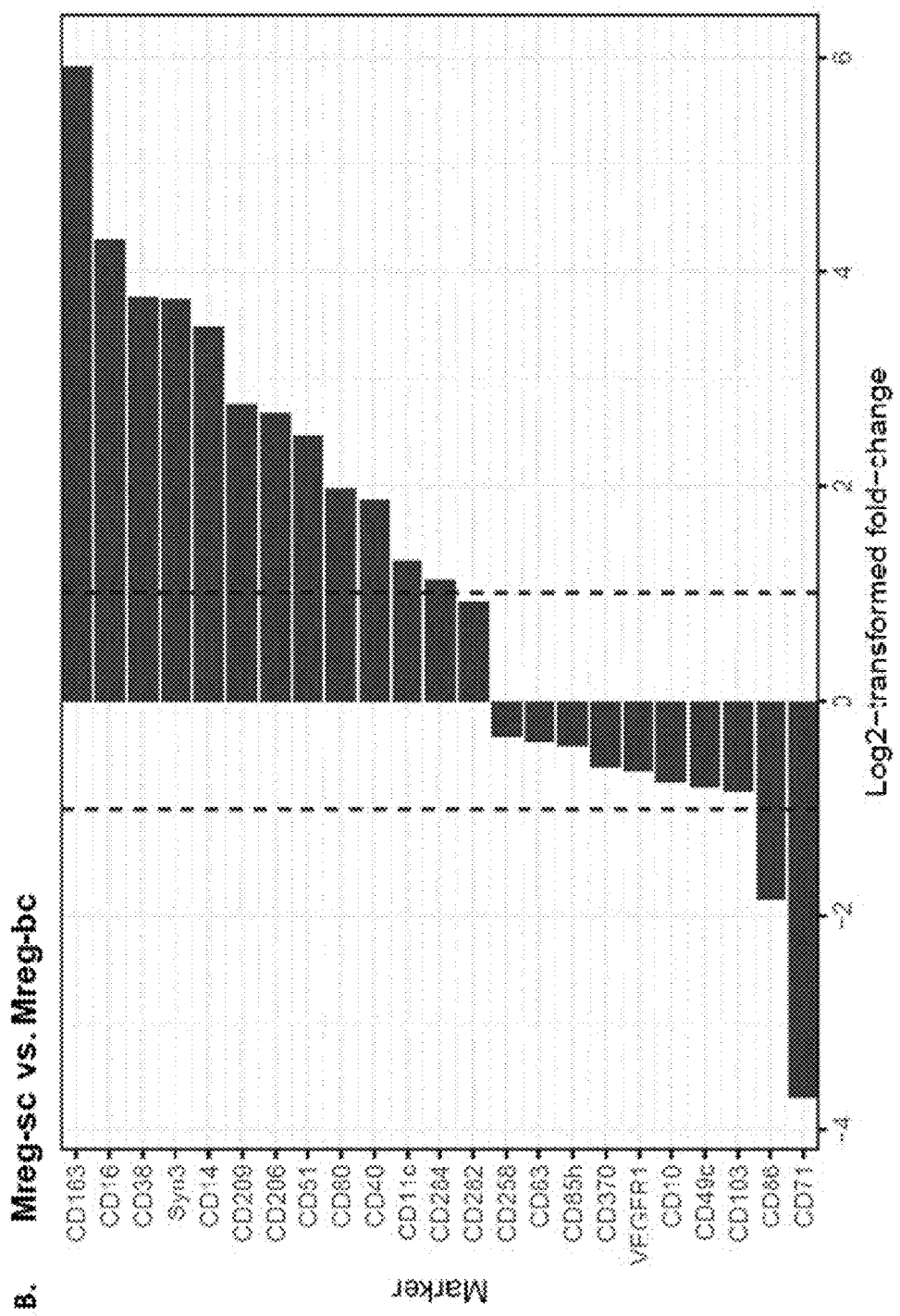

The Mregs were manufactured in accordance with current GMP principles for the production of sterile medicinal products. Attention is paid at every processing step that products, materials and equipment are protected against contamination and impurities.

Peripheral blood monocytes were isolated from leukapheresis products of healthy volunteers collected by accredited Blood collection. Informed consent for apheresis donation was obtained in accordance with the Declaration of Helsinki following to the legal regulations transposing the Directives 2002/98/EC and 2004/23/EC.

Example 1: Enrichment of Monocytes

For enrichment of monocytes, CD14+ monocytes were isolated with the GMP-compliant, fully-closed LP14 Process in CliniMACS Prodigy® (Miltenyi Biotec GmbH) according to manufacturer's instructions (LP-14 System User Manual, issued 2015-03). Prior to the process a small proportion of leukapheresis product was sampled and the total cell count and viability were determined by NucleoCounter® NC-200™ automated cell counter (ChemoMetec), and percentage of CD14+ cells and CD3+ lymphocytes from all CD45+ white blood cells were determined by flow cytometry. Similarly, after the separation process, the target cell population was checked for its purity, cell recovery and viability.

Example 2: Mreg Differentiation

For differentiation of the monocytes obtained in Example 1 into Mregs, the monocytes were divided into two different fractions. The first fraction was differentiated into Mregs in suspension culture in a Xuri™ Cell Expansion System according to the method of the invention, thereby providing Mreg-sc cells. The second fraction was differentiated into Mregs in gas-permeable bags to provide Mreg-bc cells. The key parameters of the two processes are depicted in Table 1 below.

TABLE 1

Key parameters of manufacturing processes of Mreg cells.

| Cell Type | Bioreactor | Culture vessel & cell contact material | Culture shaking property | Medium |
|---|---|---|---|---|
| Mreg-bc | N/A | bag, polyolefin | flipping of bag twice | RPMI 1640 2 mM GlutaMAX™ 1× PenStrep 10% Human AB serum 25 ng/ml M-CSF +bolus of 25 ng/ml IFN-γ on day 6 |
| Mreg-sc | Xuri™ | bag, polyethylene vinyl acetate/ low density polyethylene; or ethylene vinyl alcohol/linear low-density polyethylene | Continuous wave-type: D0-D1: 2°, 2 rpm D1-D7: 4°, 4 rpm | |

Differentiation into Mreg-Bc

Monocytes were differentiated in gas-permeable MACS GMP differentiation bags (Miltenyi Biotec) as described by [6]. When differentiating monocytes in these bags, Mregs become a semi-adherent and more homogenous cell population than their flask-cultured counterparts. Briefly, $1.8 \times 10^8$ monocytes were seeded in a 3 L differentiation bag in 180 ml (i.e. $1 \times 10^6$ cells/ml) of culture medium. The same medium was used for both processes (Table 1): RPMI 1640 supplemented with 10% Human AB serum (HABS), 2 mM GlutaMAX™ (Invitrogen, Germany), 100 U/ml Penicillin, 100 µg/ml Streptomycin (Invitrogen), and 25 ng/ml recombinant human M-CSF (R&D Systems, Germany). The bag was placed in an incubator with a humidified atmosphere at 37° C., with 5% $CO_2$. At the next day, the bag was flipped in order to provide more surface for monocytes to attach. The cell density on the bag surface was $0.27 \times 10^6$ cells/cm² (if only one surface, 672 cm 2, was counted) or $0.13 \times 10^6$ cells/cm² (if both surfaces, 1344 cm², were counted). On day 6 (18-24 h prior to harvest), human recombinant interferon-gamma (IFN-γ; Merck, Germany) was added and the bag was flipped once again. During the 7-day culture period, no medium changes were performed.

At the end of the 7-day culture period, the cells in the bag were vigorously shaken to detach them from the inner surface of the bag. The cells were then transferred by syringe to the centrifugation tubes (harvest 1) after which the bags were flushed with DPBS in order to collect the remaining cells from the bag (harvest 2). The two harvest fractions were kept separate, and the tubes were centrifuged at 300×g, at RT, for 10 min. Next, supernatants of the first harvest were collected and stored at −80° C. until Multiplex ELISA analysis. The cell pellets were resuspended to DPBS/medium/final formulation buffer (depending on the subsequent analysis). After determination of the total cell number and viability of both fractions by NC-200, they were pooled or only the harvest 1 fraction was used for further studies. These "conventionally formulated" Mreg-bc cells were allocated for phenotype characterization by flow cytometry, qPCR, and for further functional assays (see below). The harvested and "conventionally formulated" Mreg-bc were >85% viable, with recoveries of up to 70%.

Differentiation into Mreg-Sc

Monocytes were differentiated in a Xuri™ Cell Expansion System (GE Healthcare). This is a wave-type of bioreactor, originally developed and validated for expansion of T cell based cellular immunotherapy, and its mechanistic principle is that the cell culture is always in motion. Mreg-sc cells were differentiated in 2 L Xuri Cellbags™ (cat. no. 29-1054-92; GE Healthcare). For this size of the bag, the final volume range of the culture medium that can be used is 300-1000 mL. Seeding density was $1.0 \times 10^6$ cells/ml (one test run with double the amount of cells was performed) in the medium set out above in Table 1. The final process parameters that were finally established are shown in Table 2 below. More than 10 batches of Mreg-sc cells have been manufactured in accordance with these parameters.

TABLE 2

Parameters of the Xuri ™ differentiation process

| Process Step | Day | Process Parameter/Specification |
|---|---|---|
| Monocyte seeding density | 0 | $1 \times 10^6$ CD14+ cells/mL medium (see Table I) |
| Seeding volume | 0 | 300-1000 mL |
| General culture conditions | 0-7 | 5% $CO_2$, compressed air, +37° C., gas flow 0.1 L/min |
| Waving parameters | 0 | angle 2°, speed 2 rpm |
| | 1-7 | angle 4°, speed 4 rpm |
| Sampling and IFN-γ addition | 6 | sampling and IFN-γ addition (in medium, 5% volume of the batch volume) via sampling port |
| Mreg-sc harvest | 7 | cold block under the bag for 5-10 min (horizontal position, no rocking) via harvest line, pump speed 100 rpm until cell suspension reaches the harvest bag; then by gravity (harvest 1) via harvest line add cold 500 ml DPBS-2 % HSA to bag; shake with Xuri at 10 rpm, 6° for 10 min via harvest line, pump speed 100 rpm until suspension reaches the harvest bag; then by gravity (harvest 2) |

During the process development phase and after establishment of the final parameters, harvest 1 and harvest 2 were kept separately for determination of cell viability and recovery to better under-stand the process and to ensure that low quality cells are not taken to further analyses. Additionally, at the beginning, immune-phenotyping was performed separately for these two since it was not known whether Mregs readily in suspension (harvest 1) would exhibit differential pattern of extracellular marker expression from those adhering on bag surface and requiring incubation with cold buffer with increased rocking parameters (harvest 2). For secretome analysis, medium samples were collected from harvest 1. Final analyses (see Mreg-sc and below) were performed from centrifuged, resuspended and pooled harvests.

From a manufacturing point-of-view the Xuri bioreactor solved many bottlenecks that were associated to manufacturing in several, separate, cell differentiation bags. Table 3 shows the results from the bag-based and Xuri-based differentiation processes. The calculations are based on the assumption that in theory from one leukapheresis product of $0.541$-$3.55 \times 10^9$ monocytes can be obtained for further Mreg differentiation (data from >30 LPs processed by Prodigy in our lab); an average monocyte yield has been $0.850 \times 10^9$. Process recoveries and viabilities are calculated from batches (n=6; today in 2020, >10 batches) manufactured in 2019 after establishing the final process parameters for Xuri.

It is worth noticing that in this comparison, the numbers for Mreg-bc were obtained from only one 3 L differentiation bag harvested by an experienced operator. Thus, the data obtained from these "small-scale and sub-batch" derived Mregs do not fully represent a real "full-sized, clinical Mreg-bc batch". For both Mreg types, recovery and viability have been calculated from harvested, centrifuged, and buffer-formulated samples.

TABLE 3

Comparison between Mreg-sc and Mreg-bc processes

| Parameter | Bag based (Mreg-bc) | Xuri ™ bioreactor based (Mreg-sc) |
|---|---|---|
| Number of monocytes/bag[1] | $1.8 \times 10^8$ | $1 \times 10^9$ |
| Number of bags needed for x monocytes: | | |
| $5.4 \times 10^8$ monocytes | 3 | 1 |
| $9.0 \times 10^8$ monocytes | 5 | 1 |
| $3.4 \times 10^9$ monocytes | 19 | 4 (2 L); 1 (10 L)[1] |
| Recovery % (mean; ± SD) n = 6 | 77 ± 19 | 35 ± 8 |
| Viability % (mean; ± SD) n = 6 | 96 ± 3 | 97 ± 1 |
| Number of Mregs, calculated from $8.50 \times 10^8$ monocytes and recoveries | $6.55 \times 10^8$ | $2.98 \times 10^8$ |
| Estimated time (in minutes) taken for actions for a batch size of $8.50 \times 10^8$ monocytes | | |
| Day = 0 seeding | 25 | 10 |
| Day 1-bag flipping/reactor speed adjustment | 10 | 1 |
| Day 6 = Addition of interferon-γ | 25 | 5 |
| Day 7-Harvesting | 50 | 35 |

Notes:
[1] Bag size for Mreg-bc is 3L and for Mreg-sc (for Xuri, also bigger bags available);

It can be seen that the Xuri™ bioreactor-based method is associated with a lower recovery of Mreg cells compared to the bag-based approach. The main advantage of the bag-based approach is the recovery amount of the recovered Mregs. On the other hand, the Xuri™ bioreactor-based method results in a comparatively high quality of Mregs. Further, the process has a higher degree of automatization and does hence not dependent on an idiosyncratic individual operator's skills.

Being suspension-based, rather than adherent-based, it enables the production of the whole batch in one compartment, i.e., in one bag.

Example 3: Preparation of Comparator Macrophages

M1 and M2a macrophages were produced with slight modifications to the protocols described in [11] in the same gas-permeable MACS GMP differentiation bags as described above in the context with Mreg-bc. Cells were differentiated for 6 days in the same medium as Mreg-bc, but with 5 ng/ml M-CSF and 20% fetal bovine serum (FBS; Gibco) instead of HABS. On day 6, complete medium exchange was performed and serum concentration reduced to 5% FBS. At the same time, M1 cells were polarized with 100 ng/ml of lipopolysaccharides (LPS) from *Escherichia coli* (Sigma-Aldrich) and 25 ng/ml IFN-γ, while M2a cells were polarized with 20 ng/ml of recombinant human IL-4 (R&D Systems). Cells were harvested on day 7 similarly to Mreg-bc.

Example 4: Analysis of Extracellular and Intracellular Markers

The intracellular staining was performed for indoleamine 2,3-dioxygenase (IDO1). In brief, the cells were stained with Fixable Live-Dead dye and blocked with FcR Blocking Reagent. Then, the cells were stained with CD33-PE. After incubation, the cells were fixed and permeabilized and then blocked again with 10% of FcR Blocking Reagent. Finally, the cells were divided into three reaction mixes and intracellular antibodies were added as follows: Tube 1: IDO1-PerCP/eFluor710, Tube 2: IgG1-PerCP/eFluor710 isotype control or Tube 3: no antibody and analyzed after incubation and washing.

For extracellular markers, a minimum of $2 \times 10^4$ live cells (defined as CD45-positive, SYTOX Green-negative events) were analyzed with the CytoFLEX S. The initial SSC/FSC gate was set up to exclude most of the debris and dying cells. Live cells were then plotted on histograms each depicting one phenotypic marker. Background levels were set based on CD45+/SYTOX Green+ dual-stained cells in order to account for the background autofluorescence. Initially, the level of non-specific mAb binding was estimated using isotype and fluorochrome-matched, non-specific antibodies (isotype controls). A passed quality control (QC) run preceded each analysis run. Also, target MFI values were set up on an external analysis layout using identical assay parameters and Beckman-Coulter Daily QC Beads to verify the instrument performance.

Figure 1D:
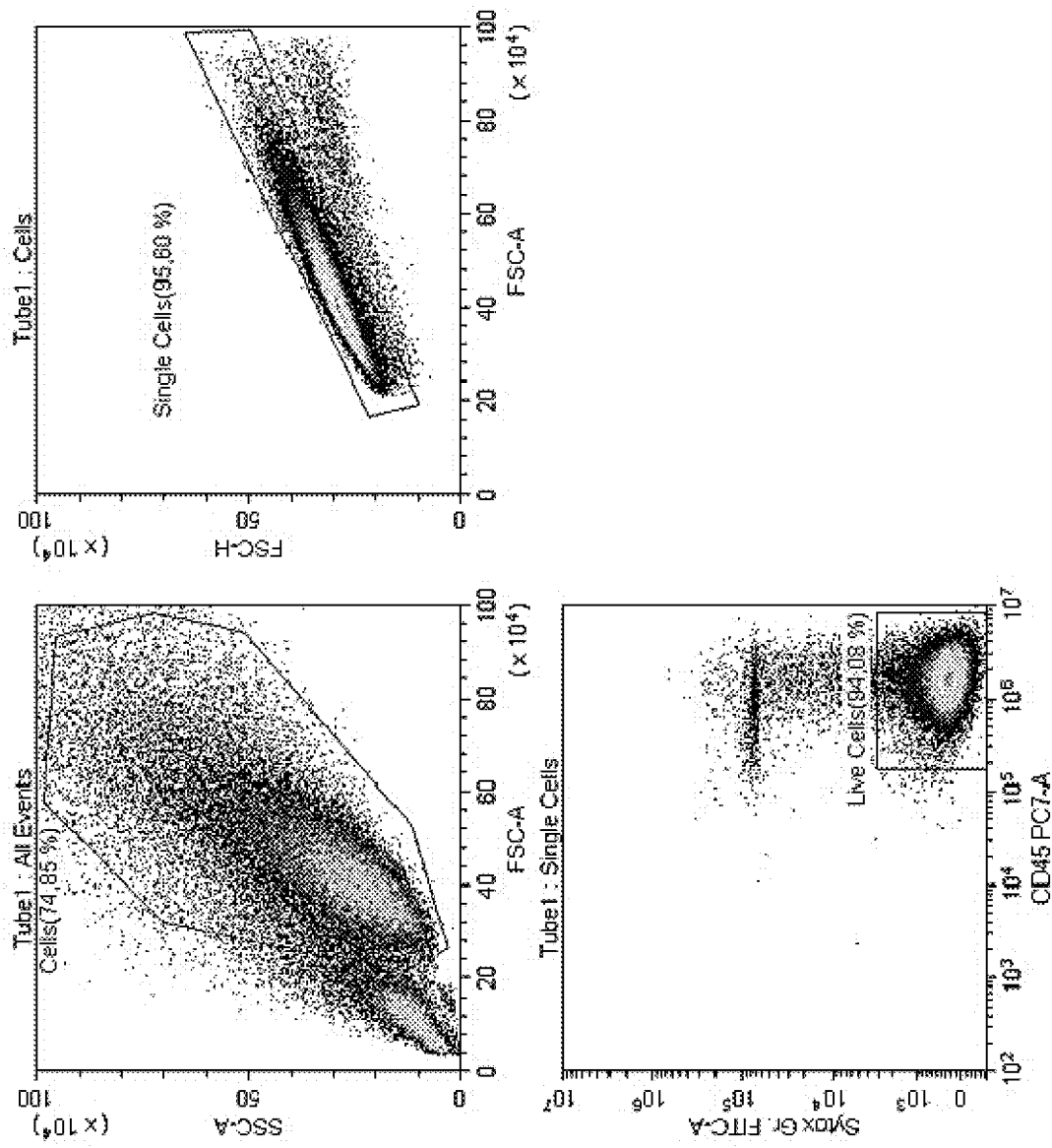

The IDO1 signal was then analyzed by flow cytometry from a minimum of $1 \times 10^4$ CD33-positive, Fixable Live-Dead stain-negative events after excluding debris, essentially by the same gating strategy as depicted in FIG. 1D. A CD33 and live/dead-stained isotype control was used to determine the level of background and non-specific fluorescence. A passed QC run on the CytoFLEX S flow cytometer preceded each analysis run.

Flow cytometric data were analyzed with FCS Express 6 Flow Research Edition (DeNovo Software, Glendale, CA, US). Median fluorescence intensity (MFI) was used as the main parameter to describe the intensity of the phenotypic marker expression. For the extracellular markers, the MFI of the control sample was subtracted from the stained sample in order to obtain a background-adjusted MFI values for each sample. For IDO1, an index of specific MFI/isotype MFI was used.

The percentage of CD14+ monocytes and CD3+ lymphocytes from all CD45+ white blood cells were determined by flow cytometry from the initial leukapheresis sample, and then again after monocyte enrichment in the Prodigy for purity check. For the phenotypic analysis the cells were stained with SYTOX Green dead cell dye as per manufacturer's instructions. The cells were then split into seven reaction mixes and stained with the markers described in Table 4 below. The cells were blocked with FcR Blocking Reagent (Miltenyi Biotec) in all flow cytometry experiments as per kit instructions.

TABLE 4

Staining scheme of extracellular phenotype markers of regulatory macrophages

| Reaction tube | BV421 | BV510 | FITC | PE | PE/Cy7 | APC |
|---|---|---|---|---|---|---|
| 1 | CD284 TLR4 | CD86 B7-2 | Sytox Gr. | CD209 DC-SIGN | CD45 PTPRC | CD370 Clec9a |
| 2 | CD83 HB15 | CD38 cADPrh | Sytox Gr. | CD85h ILT1, LILRA2 | CD45 PTPRC | CD71 TfR1, TFRC |
| 3 | CD80 B7-1 | CD10 CALLA MME | Sytox Gr. | CD103 ITGAE | CD45 PTPRC | Syndecan3 SDC3 |
| 4 | CD163 HbSR | CD14 | Sytox Gr. | CD282 TLR2 | CD45 PTPRC | CD206 MRC1 |
| 5 | CD40 | CD16 FCGR3A | Sytox Gr. | CD51 ITGAV | CD45 PTPRC | VEGFR1 FLT1 |
| 6 | (CD3)* CD3E | CD11c ITGAX | Sytox Gr. | CD258 LIGHT TNFSF14 | CD45 PTPRC | CD49c ITGA3 |
| 7 | N/A | N/A | Sytox Gr. | N/A | CD45 PTPRC | N/A |

BV421: Brilliant Violet 421,
BV510: Brilliant Violet 510,
FITC: fluorescein isothiocyanate,
PE: R-phycoerythrin,
APC: allophycocyanin,
Sytox Gr.: SYTOX Green dead cell dye (Thermo Fisher Scien-tific).
*used to assess T cell contamination in the product.
HGNC names are underlined.

The antibodies that were used for flow cytometry and intracellular staining are depicted in Table below. All antibodies depicted in the above Table were used for extracellular staining of CD14+ monocyte purity or phenotypic characterization of regulatory macrophages, except for the final three antibodies which were used for intracellular staining.

TABLE 5

Antibodies used for flow cytometry and intracellular staining

| Antibodies used | Clone | Cat.no. | S |
|---|---|---|---|
| APC anti-human CD14 | MφP-9 | 345787 | BD |
| PE anti-human CD45 | J33 | A07783 | BC |
| Brilliant Violet 421™ anti-human CD284 (TLR4) | HTA125 | 312811 | Bl |
| Brilliant Violet 421™ anti-human CD83 | HB15e | 305323 | Bl |
| Brilliant Violet 421™ anti-human CD80 | 2D10 | 305221 | Bl |
| Brilliant Violet 421™ anti-human CD163 | GHI/61 | 333611 | Bl |
| Brilliant Violet 421™ anti-human CD40 | 5C3 | 334331 | Bl |
| Brilliant Violet 421™ anti-human CD3 | OKT3 | 317343 | Bl |
| Brilliant Violet 510™ anti-human CD86 | IT2.2 | 305431 | Bl |
| Brilliant Violet 510™ anti-human CD38 | HB-7 | 356611 | Bl |
| Brilliant Violet 510™ anti-human CD10 | HI10a | 312219 | Bl |
| Brilliant Violet 510™ anti-human CD14 | M5E2 | 301841 | Bl |
| Brilliant Violet 510™ anti-human CD16 | 3G8 | 302047 | Bl |
| Brilliant Violet 510™ anti-human CD11c | 3.9 | 301633 | Bl |
| PE anti-human CD209 (DC-SIGN) | 9E9A8 | 330105 | Bl |
| PE anti-human CD85h (ILT1) | 24 | 337904 | Bl |
| PE anti-human CD103 (Integrin αE) | Ber_ACT8 | 350205 | Bl |
| PE anti-human CD282 (TLR2) | TL2.1 | 309707 | Bl |
| PE anti-human/rat CD51 (Integrin αvβ5) | P1F6 | 920007 | Bl |
| PE anti-human CD258 (LIGHT) | T5-39 | 318706 | Bl |
| PE/Cy7 anti-human CD45 | HI30 | 304016 | Bl |
| APC anti-human CD370 (CLEC9A/DNGR1) | 8F9 | 353805 | Bl |
| APC anti-human CD71 | CY1G4 | 334107 | Bl |
| APC anti-human CD206 (MMR) | 15-2 | 321109 | Bl |
| APC anti-human CD49c (integrin α3) | ASC-1 | 343808 | Bl |
| Anti-VEGFR-1 (Flt-1)-APC, human | REA569 | 130-108-930 | MB |
| Human Syndecan-3 APC-conjugated | polyclonal | FAB3539A | R&D |

TABLE 5-continued

Antibodies used for flow cytometry and intracellular staining

| Antibodies used | Clone | Cat.no. | S |
|---|---|---|---|
| PE anti-human CD33 | P67.6 | 345799 | BD |
| PerCP-eFluor 710 Mouse IgG1 K Isotype Control | P3.6.2.8.1 | 46-4714-82 | eB |
| PerCP-eFluor 710 IDO1 Monoclonal Antibody | eyedio | 46-9477-42 | eB |

Key:
S = Supplier.
BD = Becton Dickinson Biosciences.
BC = Beckman Coulter.
Bl = Biolegend.
eB = eBiosciences.
MB = Miltenyi Biotec.
R&D = R & D Systems.

Figure 2A:
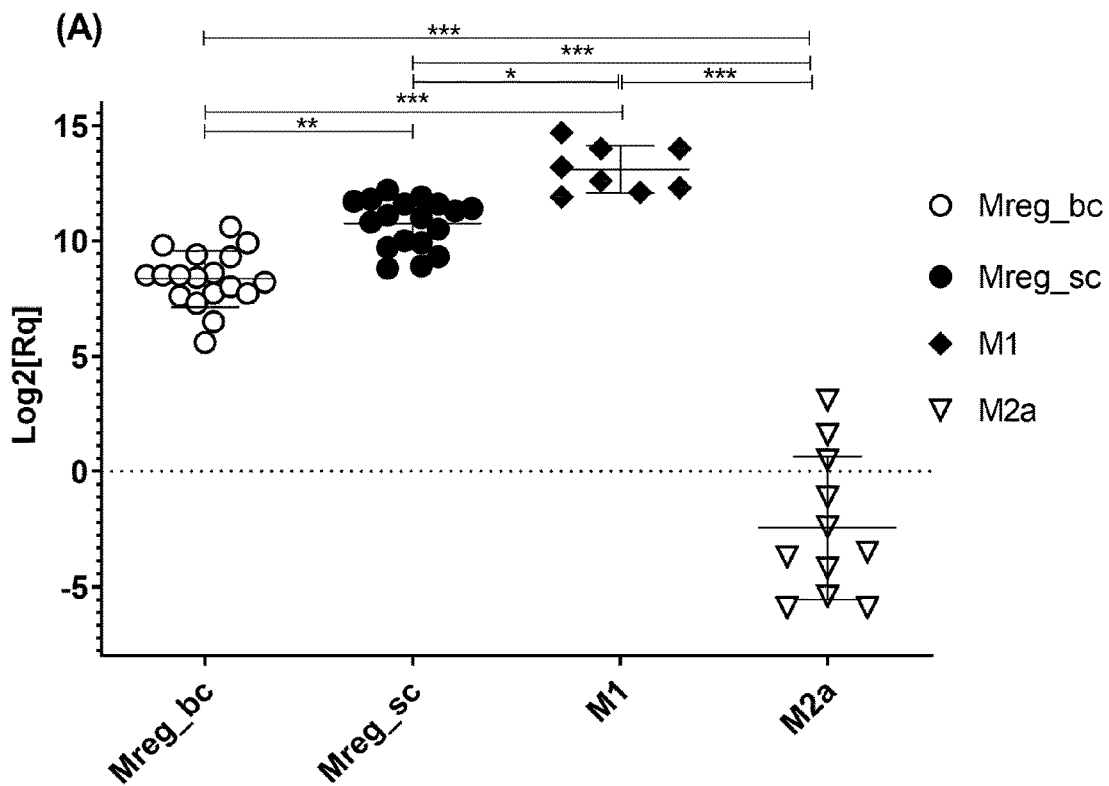
FIG. 2 shows the results of the gene expression analysis in different macrophages: (A) IDO1 mRNA expression by RT-qPCR; (B) IDO1 protein expression by flow cytometry; (C) Correlation of IDO1 protein expression with detected mRNA levels; (D) DHRS9 mRNA expression by RT-qPCR. Statistical significance of difference in expression between the two products with $p<0.0001$ is indicated by *; $p<0.001$  and $p<0.01$ *. In panels (A) and (D) the dashed line at Log2[Rq]=0 indicates no change in mRNA expression; values above the line indicate mRNA upregulation and values below the line indicate mRNA down-regulation. In panels (B) and (C) the dashed line at MFI=2 indicates a preliminary detection threshold where IDO1 protein is expressed by macrophages at least two-fold higher than the background fluorescence.
Figure 2B:
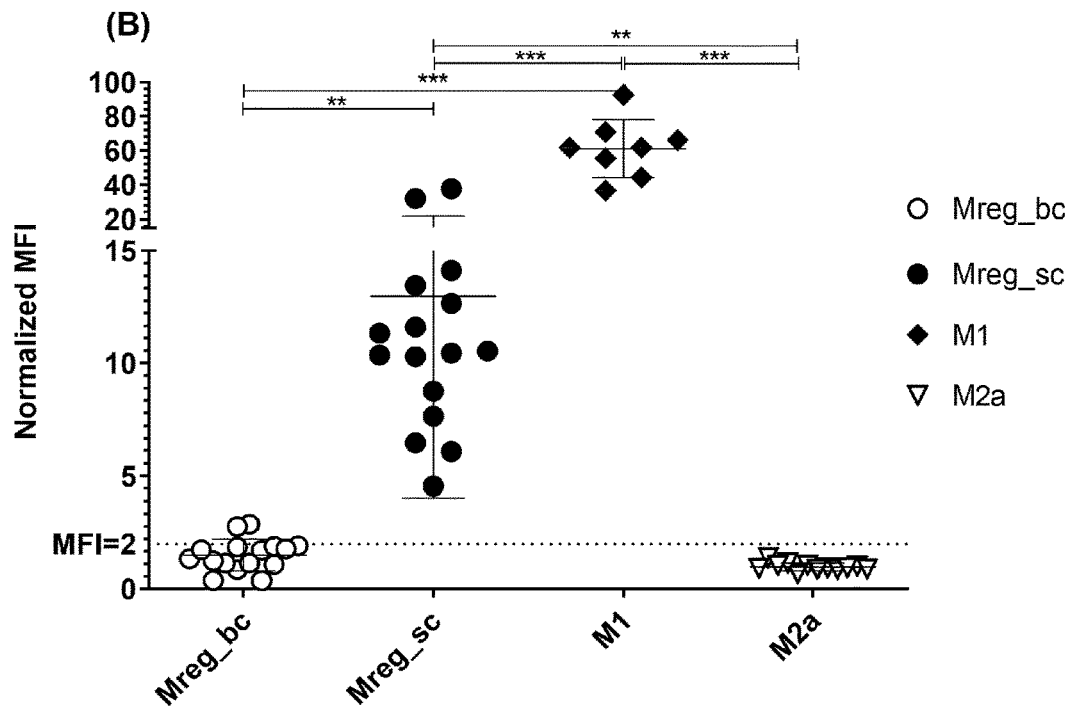
Figure 2C:
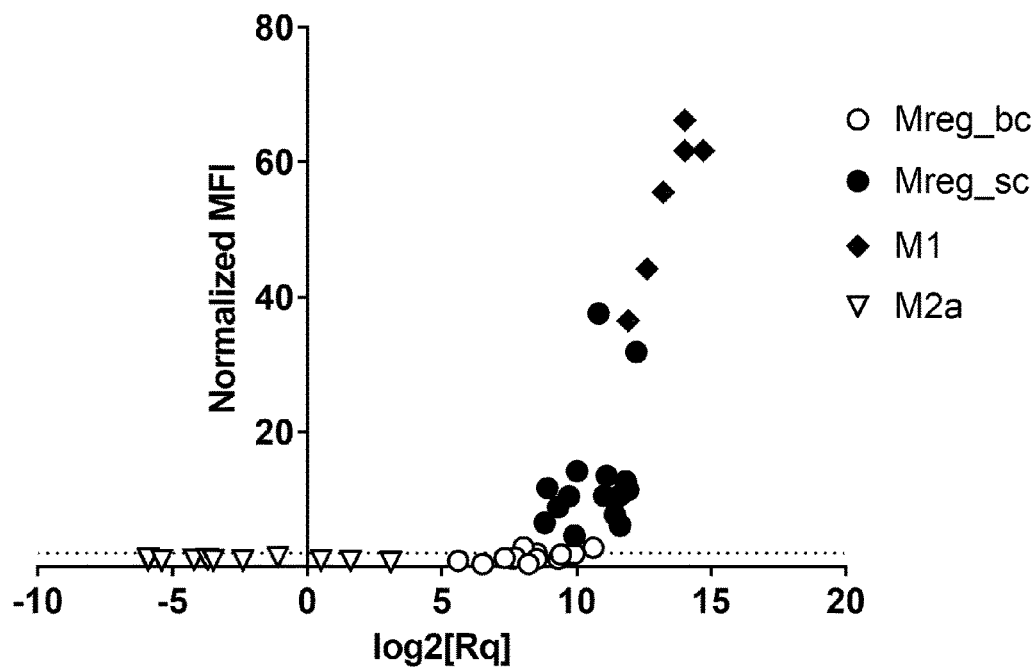

Results: The results obtained from the marker analysis are depicted in FIG. 1. It can be seen that both Mreg processes consistently yielded relatively homogenous populations of macrophages, with certain distinct differences between the two processes. The Mreg-bc cells displayed a prom-inent down-regulation of multiple activation-associated markers, such as CD38, CD40 and CD80, and elevated levels of markers CD86 and CD71 determined by flow cytometry. The notable factors for the Mreg-sc process were high levels of CD11c, CD14, CD16, CD51, CD163 and syndecan-3. Hence, multiple markers allow for a reliable differentiation between the two macrophage products. Furthermore, the two processes were set apart by the differential expression of IDO1, with markedly higher levels seen in Mreg-sc (FIG. 2B). A direct correlation between the degree of IDO1 mRNA upregulation and IDO1 protein expression was observed (FIG. 2C), although some level of mRNA accumulation is required before IDO1 is detected on protein level.

As a result, not all batches of Mreg-bc showed expression of IDO1 on protein level even though the mRNA was at least 50-fold upregulated compared to CD14+. Thus, IDO1 expression levels can potentially be used to differentiate between different types of macrophages, and even between Mreg-sc and Mreg-bc.

Example 5: Gene Expression Characterization by RT-qPCR

For RT-qPCR $5 \times 10^6$ cells were resuspended in 500 µl RNAprotect Cell reagent (Qiagen) and frozen at −20° C. Total RNA was extracted from cells using RNeasy Protect Cell Mini Kit (#74624, Qiagen) with QIAshredder disposable cell-lysate homogenizers (#79654, Qiagen). RNA amount was quantified by NanoDrop OD260 measurements. Four pg of RNA from each sample was treated with DNAse I (#DNASE-50 PrimerDesign or #18068015 Invitrogen) according to manufacturer's instruction. After the concentration of the samples was adjusted to 50 ng/µl and verified by Qubit™ Fluorometer (Invitrogen) measurements using Qubit™ RNA HS Assay Kit (#Q32855, Invitrogen). Relative expression of DHRS9 and IDO1 mRNA was measured by RT-qPCR using TaqPath 1-Step Multiplex Master Mix Kit (#A28526 Applied Biosystems) and QuantStudio 5 Real-time PCR system (Applied Biosystems) according to manufacturer's instruction. Taqman assays were purchased from Applied Biosystems: for Human IDO1 assay number Hs00984148_m1 (FAM-MGB), for Human DHRS9 Hs00608375 m1 (FAM-MGB) and for Human GAPDH Hs03929097_g1 (VIC-MGB). Expression of GAPDH mRNA was used as an en-dogenous control gene for data normalization. Each amplification reaction contained 50 ng of RNA and was performed in triplicates. Obtained amplification data was analyzed with QuantStudio Design and Analysis desktop Software (Applied Biosystems). Changes in expression were calculated relative to expression of corresponding mRNA in the starting material, i.e. CD14+ monocytes.

Figure 2D:
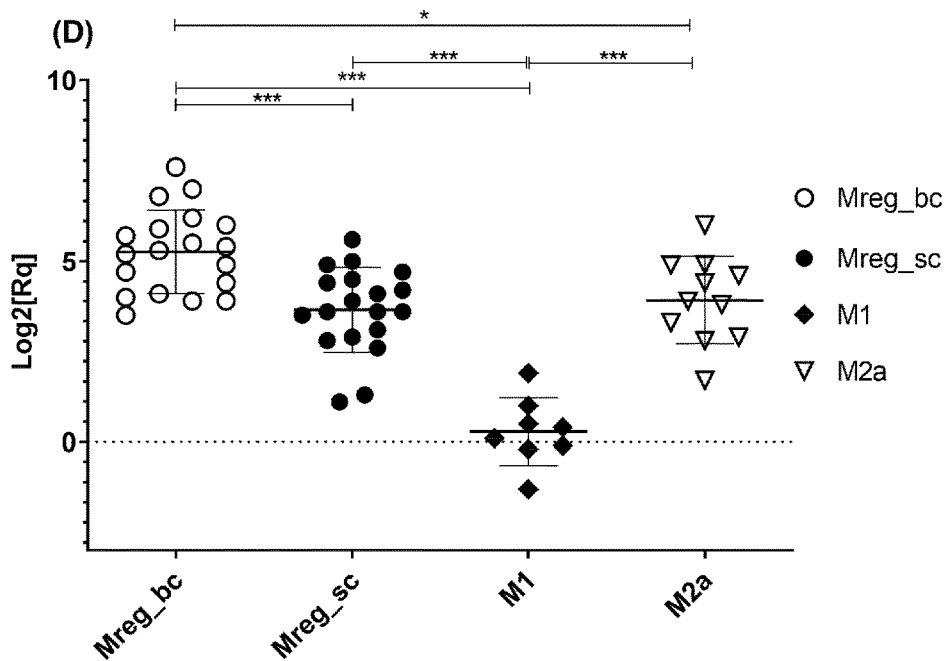
Figure 3:
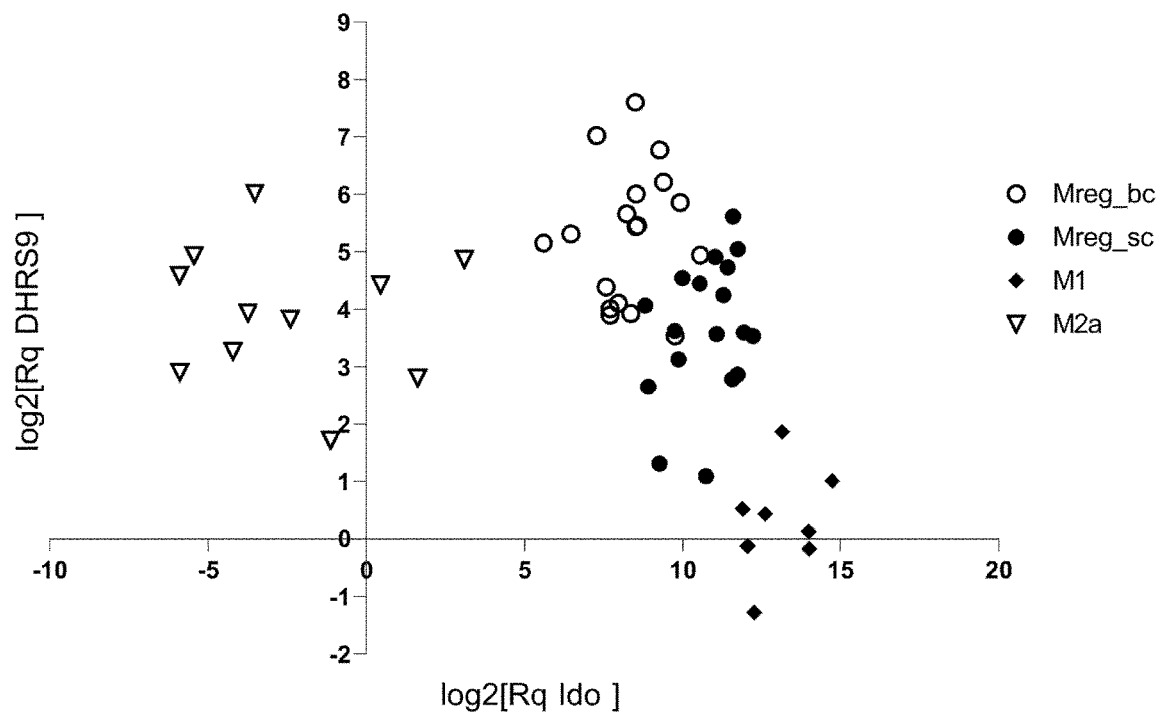
FIG. 3 shows the separation of regulatory macrophages from M1 and M2a macrophages based on expression of DHRS9 and IDO1 mRNA.

Results: DHRS9 expression was considerably increased in Mreg-bc, Mreg-sc and M2a cells (FIG. 2D). For M1 cells, expression of DHRS9 was significantly lower, with some M1 batches showing downregulation of DHRS9 mRNA when compared to the starting CD14+ monocyte population. Thus, the set of two genes, IDO1 and DHRS9, can assist in identification of regulatory macrophages from M1 and M2a phenotypes. Regulatory macrophages exhibit elevated expression of both IDO1 and DHRS9, while M1 pro-inflammatory macrophages have increased expression of IDO1 only and M2a anti-inflammatory macrophages express DHRS9 only (FIG. 3).

Example 6: Cytokine and Growth Factor Secretion Profiles

For secretome analysis, cell culture medium samples were collected during harvest. All the samples were stored at −80° C. until analysis with Bio-Plex Pro™ Human Cytokine 27-plex Assay kit (Bio-Rad Laboratories, Hercules, CA, USA; #M500KCAF0Y). The kit provides for the detection of the anti-inflammatory factors IL-1ra, IL-4, IL-10, IL-13, the pro-inflammatory factors TNF-α, IL-1B, IL-2, IL-5, IL-6, IL-7, IL-8, IL-9, IL-12, IL-15, IL-17, RANTES, Eotaxin, MIP-1α, MIP-1β, MCP-1 [MCAF], INF-γ, IP-10 and the growth factors PDGF bb, VEGF, G-CSF, GM-CSF, and bFGF. Despite of previous categorization, several of these factors are pleiotropic, and thus, their functions are depending on the affected cell types and the microenvironment where they are expressed.

The experimental procedure was performed according to the manufacturer's instructions. Briefly, magnetic beads coated with capture antibodies were incubated with pre-mixed standards or sample supernatants on a shaker for 30 min. Then, the detection antibodies were added and incubated as above. After washing, streptavidin-PE was added and incubated for 10 min. After washing, the beads were re-suspended in assay buffer, and results were read on the Bio-Plex® 200 system. Data were analyzed with Bio-Plex Manager™ software version 4.1.1. The secretion profiles, i.e. the secretomes, of non-stimulated (basal level) Mreg-sc and Mreg-bc cells from medium samples collected upon harvest were determined.

Figure 5:
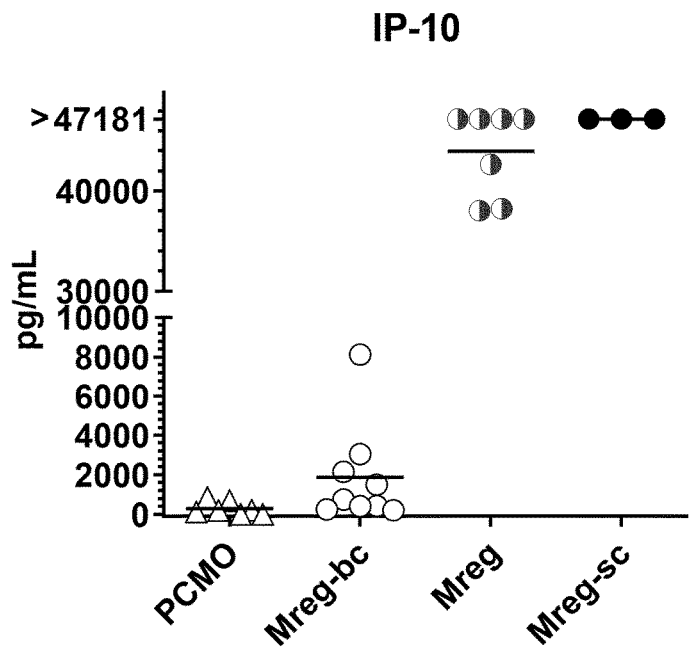
FIG. 5 shows that the basal secretome profiles of Mreg-bc and Mreg-sc are very similar. Only IP-10 from the 27 factors measured were differentially secreted to the medium. Estimated concentrations in pg/mL are shown in y-axis.
Figure 4:
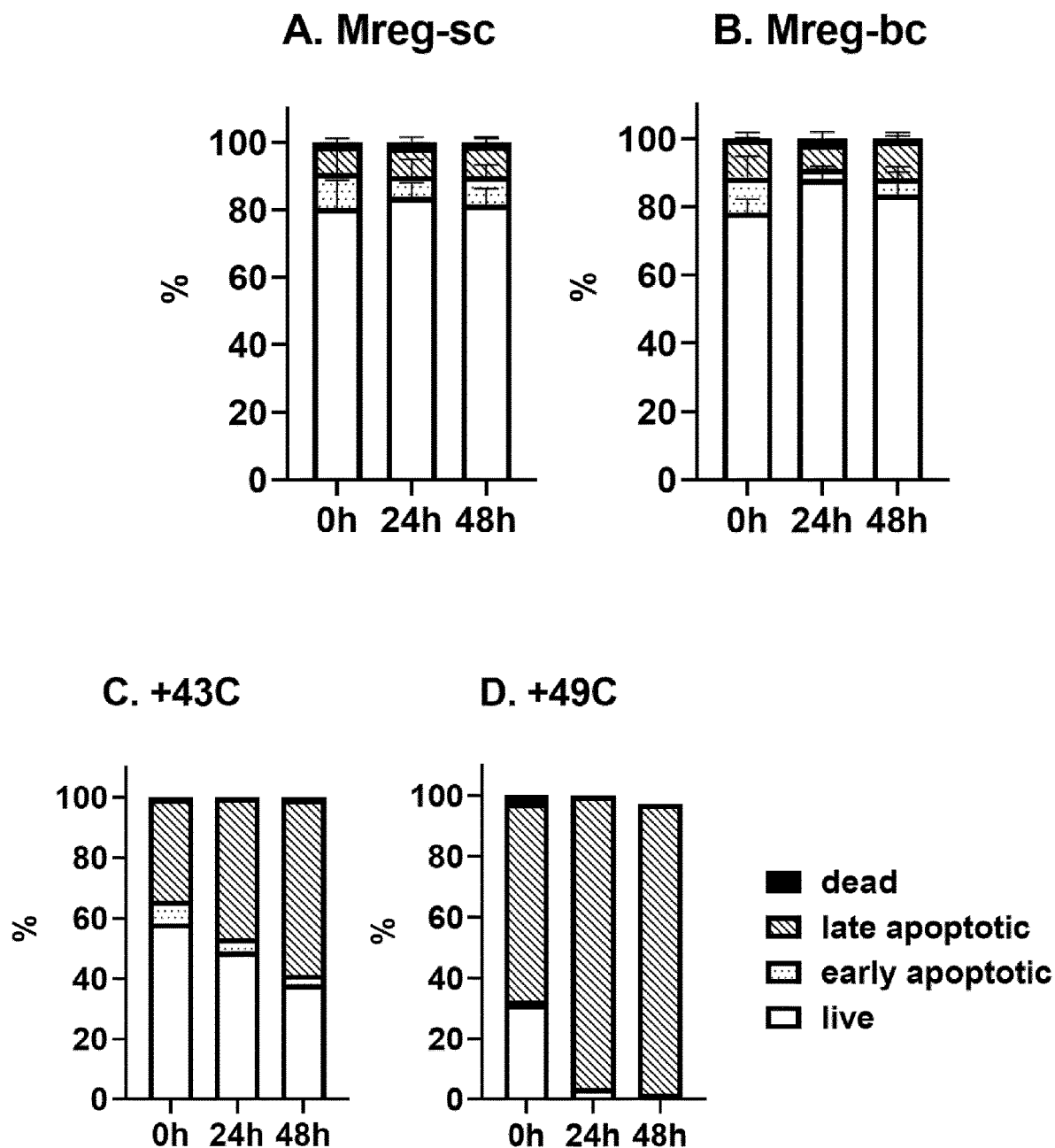
FIG. 4 is a depiction of the preliminary stability data (n=2) demonstrating that Rotea formulated Mreg cells retain high viability at least up to 48 h when stored at +4° C. (A) Mreg-sc (B) Mreg-bc and (C) heat-treated controls at 0 h, 24 h, and 48 h in 5% HSA plasmalyte. For determination of cell viability and quality, Annexin V Apoptosis kit was used and analyzed by MUSE® Cell Ana-lyser.

Results: Secretome profiles of Mreg-sc (n=3; produced in 2019 with final Xuri process parameters) and Mreg-bc (n=11, samples collected from batches 2018-2019) were analyzed by BioRad multiplex enzyme-linked immunoassay. From 27 factors that were analyzed, 8 were found differently released from Mreg-bc and Mreg-sc when using a Welch two sample method in R (data not shown). However, further checking, and parallel comparison to secretomes of M1 and M2a macrophages, only secretion of IP-10 (FIG. 5), an IFN-γ induced protein 10 [13], could be found to be significantly secreted from Mreg-sc but not from Mreg-bc. As a conclusion, the basal secretion profiles of these two Mreg products appear to be very similar to each other.

Example 7: Phagocytosis Assay

A flow cytometry-based phagocytosis assay was performed with Mreg-sc (cultured in suspension) and Mreg-bc (cultured in bags) to evaluate the functional ability of macrophages. The assay was performed with harvested macrophages and cryopreserved and thawed CD14+ monocytes and CD3+ T cells using the pHrodo Green *Escherichia coli* (*E. coli*) BioParticles Phagocytosis Kit for Flow Cytometry (Invitrogen by ThermoFisher Scientific, #P35381) according to the manufacturer's protocol with slight modifications. Briefly, one million macrophages/monocytes that were allowed to adhere for at least 1 hour post-harvest and 0.5 million T cells were incubated with pHrodo Green *E. coli* BioParticles Conjugate (1:20 dilution in culture medium) for 1 hour at +37° C. as well as on ice in order to inhibit particle uptake. After washing, cells were harvested and suspended in 100 µl of FACS buffer. Cells were stained with 5 µl of 7-AAD viability dye (BD Biosciences, #559925) and 1 µl of CD45-PE/Cy7 (Biolegend, #304015), and additionally, 1 µl of CD3-BV421 (Biolegend, #317344) for T-cell samples. After incubation for 15 min at RT in the dark, unbound antibodies were removed by a wash with 2.5 ml of FACS buffer prior to acquisi-tion on the CytoFLEX S flow cytometer (Beckman Coulter, US). A minimum of $4 \times 10^4$ live cells (doublet discriminated CD45-positive, 7-AAD-negative) were acquired. Flow cytometric data were analyzed in the FlowJo software (TreeStar, US). Phagocytosis was determined as an increase in pHrodo™ Green fluorescence relative to the one observed with control sample, incubated on ice, and calculated as the frequency of pHrodo™ Green-positive cells that had engulfed particles (percentage positive).

Figure 6:
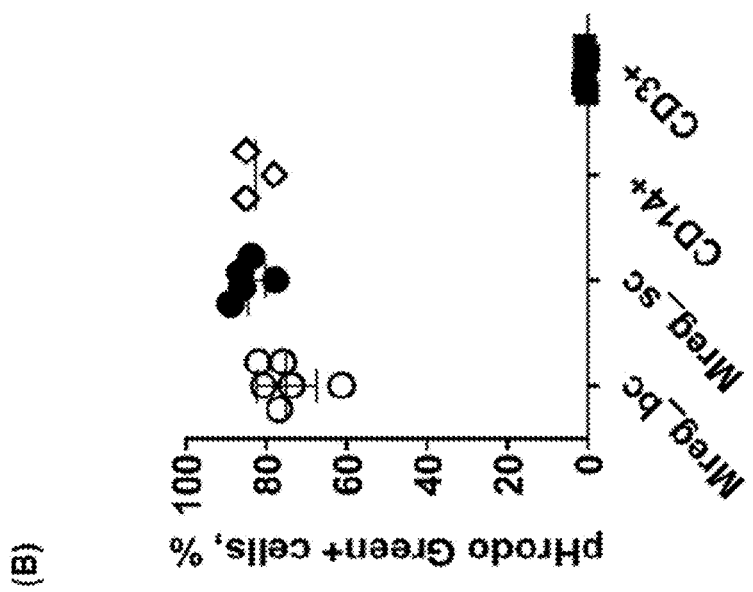
FIG. 6 shows the results from the phagocytosis assays using pHrodo Green *E. coli*. Mreg cells were incubated with *E. coli* particles for 1 hour and analyzed with flow cytometry. (A) Representative histograms of engulfed particles, measured as pHrodo Green fluorescence intensity, in Mreg-bc. Dashed light-gray plot indicates the control without particles incubated at +37° C., light-gray plot shows the control with particles incubated on ice, and dark-gray plot represents the sample with particles incubated at +37° C. (B) Dot plots of the percentages of the cells that had internalized labelled E. coli particles. Results are depicted as mean±SD percentages of pHrodo Green-positive cells within the live CD45-positive population (live CD45+CD3+ for T cells).
Figure 6:
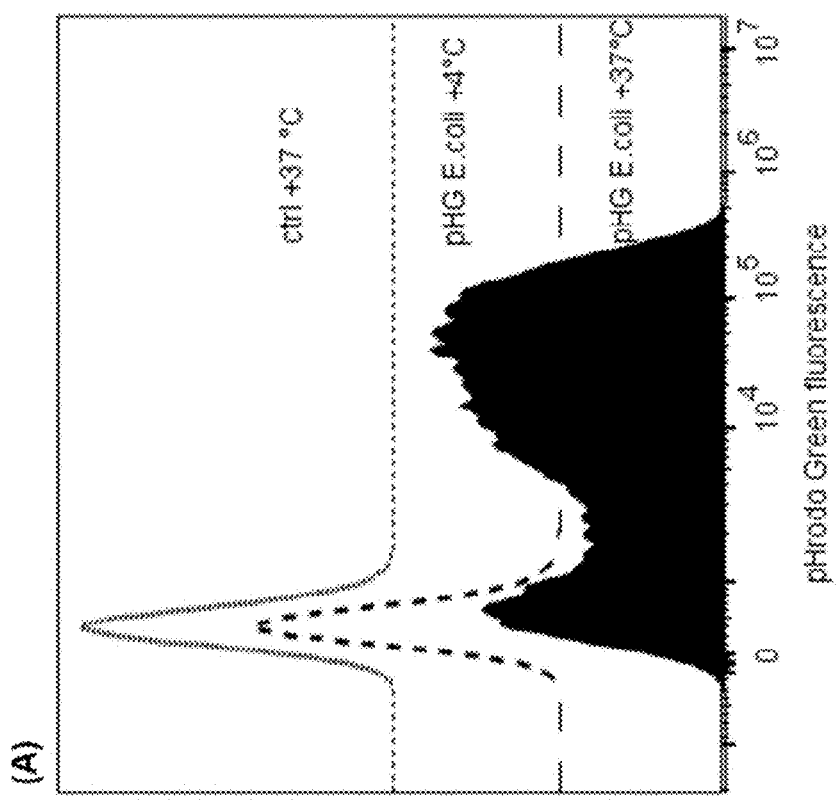

Results: The results are shown in FIG. 6. Flow cytometry analysis showed that both Mreg types (and monocytes) are actively phagocytosing *E. coli* (FIG. 6A). The detection of phagocytosis events was confirmed by a negative control that contained target particles and was incubated on ice, thus preventing phagocytosis (FIG. 6A). After 1 hour, 85+4% of Mreg-sc and 75+7% Mreg-bc macrophages (83±4% monocytes) had internalized particles (FIG. 6B).

Example 8: T Cell Suppression Assay

The expression of IDO1 was identified as the main culprit of the Mreg suppressive effect on T cell proliferation [6], [11], likely due to induced tryptophan deprivation. As shown above, Mreg-sc express higher levels of indoleamine IDO1 than Mreg-bc both on the mRNA and protein level. Therefore, it was investigated whether Mreg-sc exert a stronger Mreg-mediated suppression of T cell proliferation. Suppression tests were performed according to the protocol described in [11] with minor modifications. One day prior to Mreg harvest CD3+ T cells of allogenic donors were fluorescently labeled with CytoTell Green (22253, AAT Bioquest) according to manufacturer's protocol. CytoTell-labeled and unlabeled control T cells were activated using MACSbeads (in 1 bead per 2 cells; 130-091-441, Miltenyi Biotec). The cells were cultured in RPMI growth medium supplemented with 5% HABS, 1% Glutamax and 100 IU/ml Penicillin and 100 µg/ml Streptomycin overnight (+37° C., 5% $CO_2$) along with non-activated control CytoTell™-labeled T cells. Next day, freshly harvested macrophages and thawed cryopreserved monocytes were plated into wells of 48-well plate in the culture medium specified above. Cells were allowed to attach for 2 hours (+37° C., 5% $CO_2$) prior to addition of T cells. The total amount of seeded monocytes/macrophages varied from $6.25 \times 10^4$ to $3.75 \times 10^5$ cells per well, so that upon addition of $1.25 \times 10^5$ T cells to the wells resulting co-cultures were at 3:1, 2:1, 1:1 and 1:2 effector cells to T cell ratios. To investigate the role of IDO1 in Mreg-mediated suppression of T cell proliferation IDO1 inhibitor (1-methyl DL-tryptophan, 860646, Sigma Aldrich) was added to separately designated 3:1 co-cultures. After 72 h in co-culture (+37° C., 5% $CO_2$) non-adherent cells (mainly T cells) were harvested and labeled with anti-CD3-APC (300312, BioLegend) to identify T cells. For live/dead discrimination 7-AAD (559925, BD Biosciences) exclusion was used. Extent of T cell proliferation was assessed by flow cytometry on CytoFLEX S. Flow cytometric data were exported as FCS 3.0 files and proliferation analysis was carried out in FCS Express 6 Flow Research Edition to calculate proliferation index (PI) for the viable T cell population (CD3 positive cells, 7-AAD negative). Proliferation index in FCS express represents fold expansion during culture (ratio of final cell count to starting cell count) and is calculated according to formula:

$$PI = \frac{\sum_0^i Ni}{\sum_0^i \frac{Ni}{2^i}}$$

where i is the cell generation and N is the number of cells observed in that generation.

Figure 7:
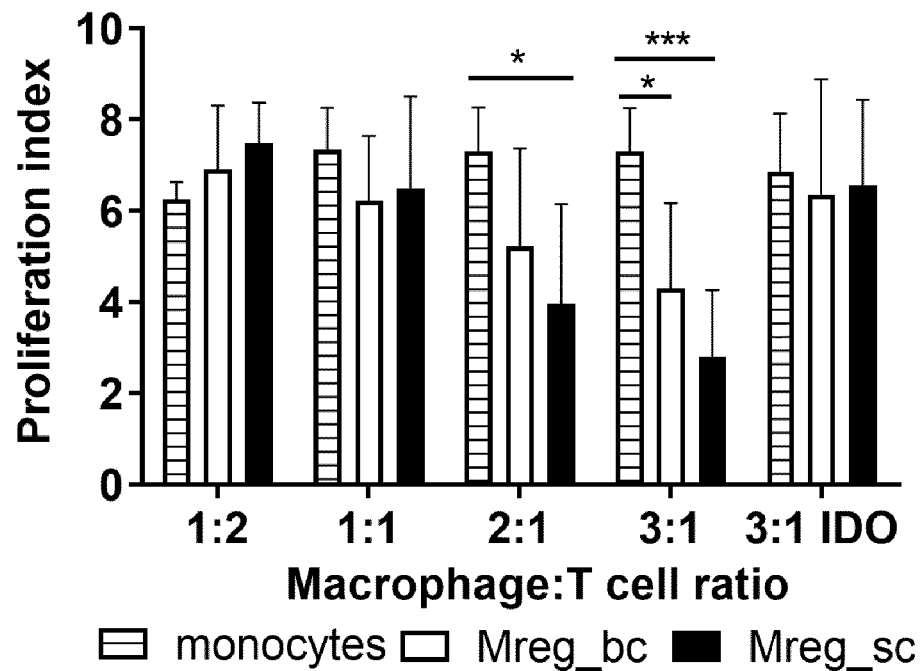
FIG. 7 demonstrates that Mreg-sc cells are able to inhibit T cell (CD3+) proliferation in co-cultures (72 h). Results are shown as mean±SD from 3-5 Mreg batches (i.e. 3-5 donors). Statistical significance is shown as * $p<0.05$, *** $p<0.001$. The addition of an IDO1 inhibitor (1 mM 1-methyl DL-tryptophan) to the co-culture restored proliferation of the T-cells to the level observed with non-suppressing monocytes. Key: first bar=monocytes; second bar=Mreg-bc; third bar=Mreg-sc.
Figure 8:
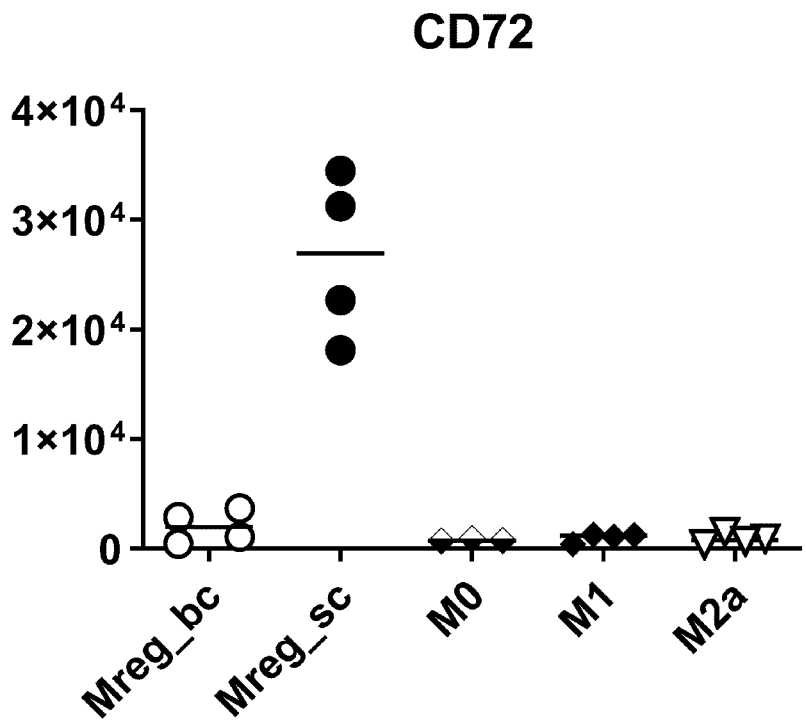
FIG. 8 shows the results of CD72 expression in Mreg-bc and Mreg-sc and M0, M1 and M2a macrophages.
Figure 9:
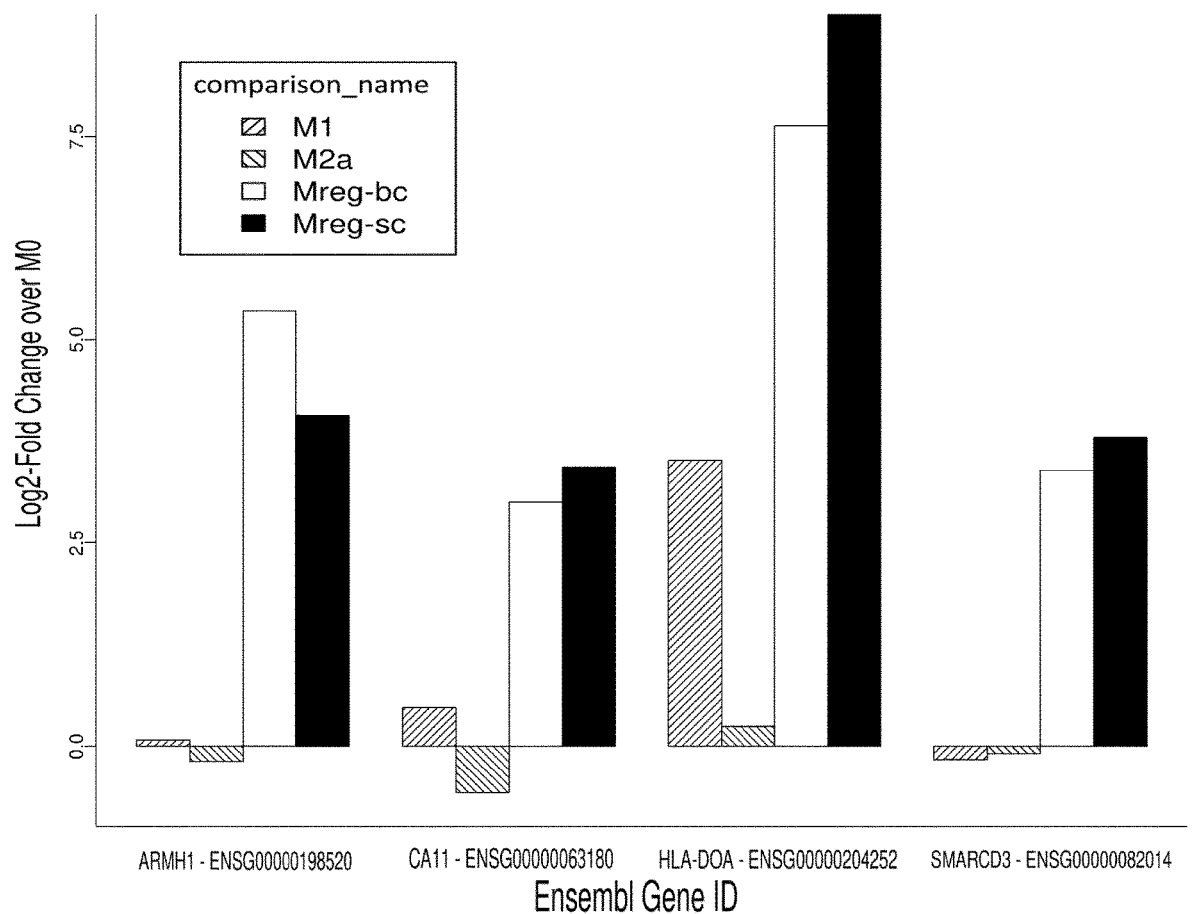
FIG. 9 shows the results from transcriptomic analysis. Mreg-sc, Mreg-bc, M1 and M2a were compared to M0 macrophages. The log 2-fold changes of gene transcripts are presented for the genes ARMH1, CA11, SMARCD3 and HLA-DOA. ARMH1, CA11, SMARCD3 are expressed at the same level in M0, M1 and M2a cells. These genes are >4 fold higher (about >log 2 fold change) expressed in Mregs compared to M0, M1 and M2a. HLA-DOA has a 3-fold higher expression Mregs compared to other macrophages.
Figure 10:
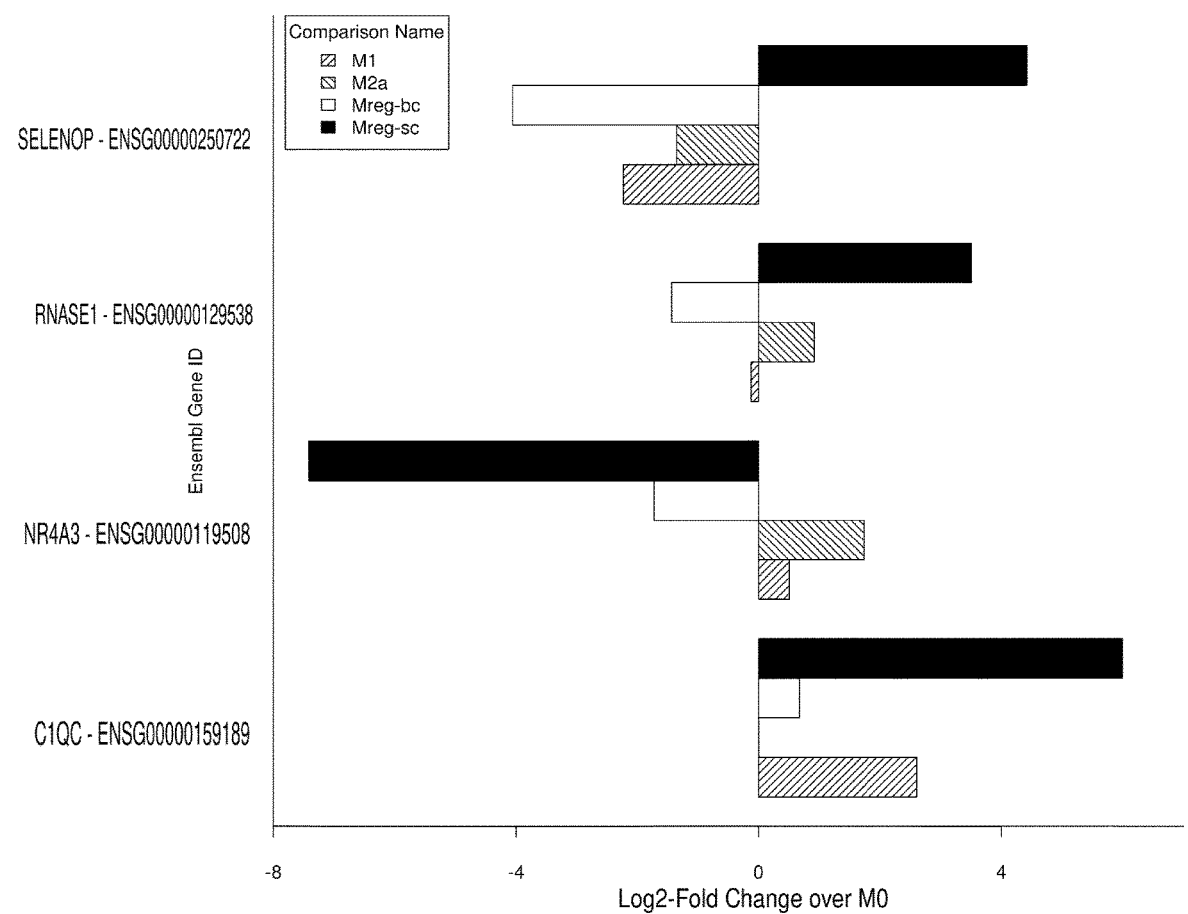
FIG. 10 shows that gene transcripts of SELENOP, RNASE1, C1QC and NRA4A3 can be used as specific markers for Mreg-sc. In Mreg-sc NRA4A3 is downregulated, while SELENOP, RNASE1 are C1QC are upregulated.

Results: No significant difference in T cell proliferation was observed in 1:2 and 1:1 co-cultures with Mreg-sc, Mreg-bc or monocytes. However, at higher cell ratios, 2:1 and 3:1, T cells co-cultured with both Mreg-sc and Mreg-bc proliferated at a lesser extent than T cells cultured alone (data not shown) or in co-cultures with monocytes (FIG. 7). The observed suppression of T cell proliferation was exacerbated with Mreg-sc. Addition of the IDO1 inhibitor (1 mM 1-methyl DL-tryptophan) to the 3:1 co-culture relieved inhibitory effect and restored proliferation of the T-cells to the level observed with non-suppressing monocytes. This confirmed that the inhibitory effect seen in T cell proliferation is linked to the IDO1 expression level by the regulatory macrophages and not to non-specific nutrient limitation in co-cultures.

LITERATURE

[1] Hutchinson J A, Riquelme P, Sawitzki B, et al. Cutting edge: immunological consequences and trafficking of human regulatory macrophages administered to renal transplant recipients. J Immunol 2011; 187:2072-8.
[2] Hutchinson J A, Riquelme P, Brem-Exner B G, et al. Tranplant acceptance-inducing cells as an immune-conditioning therapy in renal transplantation. Transpl Int 2008; 21:728-41.
[3] Hutchinson J A, Brem-Exner B G, Riquelme P, et al. A cell-based approach to the minimi-zation of immunosuppression in renal transplantation. Transpl Int 2008; 21: 742-54.
[4] Hutchinson J A, Roelen D, Riquelme P, et al. Preoperative treatment of a pre-sensitized kidney transplant recipient with donor-derived transplant acceptance-inducing cells. Transpl Int 2008; 21: 808-13.
[5] Hutchinson J A, Govert F, Riquelme P, et al. Administration of donor-derived transplant acceptance-inducing cells to the recipients of renal transplants from deceased donors is technically feasible. Clin Transplant 2009; 23: 140-5.
[6] Hutchinson J A, Ahrens N, Geissler E K. MITAP-compliant characterization of human regulatory macrophages. Transplant International 2017; 30(8), 765-775.

[7] Hummitzsch L, Zitta K, Rusch R, et al. Characterization of the Angiogenic Potential of Human Regulatory Macrophages (Mreg) after Ischemia/Reperfusion Injury In Vitro. Stem Cells International 2019; June 25.

[8] de Araújo EF, Medeiros D H, Galdino N A et al. Tolerogenic Plasmacytoid Dendritic Cells Control *Paracoccidioides brasiliensis* Infection by Inducting Regulatory T Cells in an IDO-Dependent Manner. PLoS Pathogens 2016; 12(12), 1-29.

[9] Yun T J, Lee, J S, Machmach K, et al. Indoleamine 2,3-Dioxygenase-Expressing Aortic Plasmacytoid Dendritic Cells Protect against Atherosclerosis by Induction of Regulatory T Cells. Cell Metabolism 2016; 23(5), 852-866.

[10] Zhao Y, Wu T, Shao S, et al. Phenotype, development, and biological function of mye-loid-derived suppressor cells. Oncoimmunology 2016; 5(2), e1004983

[11] Hutchinson J A, Riquelme P, Geissler, EK, Fändrich, F. Human regulatory macrophages. Methods Mol Biol 2011; 677, 181-192.

[12] Munn D H, Shafizadeh E, Attwood J T, et al. Inhibition of T Cell Proliferation by Macrophage Tryptophan Catabolism. The Journal of Experimental Medicine 1999; 189(9), 1363-1372.

[13] Shanmugam N, Reddy M A, Guha M, et al. High glucose-induced expression of prom-flammatory cytokine and chemokine genes in monocytic cells. Diabetes 2003; 52(5), 1256-1264

The invention claimed is:

1. A process for preparing an immunoregulatory macrophage cell, said process comprising:
   (a) isolating CD14 positive monocytes from a blood sample of a subject;
   (b) culturing the monocytes in a culture medium containing (i) M-CSF and/or GM-CSF, and (ii) a CD16 ligand;
   (c) contacting the monocytes or monocytes-derived cells with IFN-γ; and
   (d) obtaining the immunoregulatory macrophage cell from the culture medium, wherein steps (b) and (c) are performed in a container that is agitated to avoid adherence of the cells to the surface of the container.

2. Process of claim 1, wherein step (d) does not include the mechanical detachment of cells from the surface of the container.

3. Process of claim 1, wherein steps (b) and (c) are performed such that not more than 10% of the cells adhere to the surface of the container.

4. Process of claim 1, wherein the culture medium in step (b) comprises human blood serum.

5. Process of claim 1, wherein the concentration of M-CSF and/or GM-CSF in step (b) is in the range of 5-100 ng/ml.

6. Process of claim 1, wherein the monocytes in step (b) are cultured for at least 3 days, for at least 4 days, for at least 5 days, for at least 6, or for at least 7 days prior to contacting with IFN-γ.

7. Process of claim 1, wherein the container is made of plastic.

8. Process of claim 1, wherein the concentration of IFN-γ in step (c) is in the range of 5-100 ng/ml.

9. Immunoregulatory macrophage cell obtainable by a process according to claim 1.

10. Immunoregulatory macrophage cell, wherein said cell expresses the following markers: CD16, CD163, and Syndecan-3.

11. Immunoregulatory macrophage cell of claim 10, wherein said cell further expresses at least one of the following markers: CD51, CD11c, CD72, IDO1.

12. Pharmaceutical composition comprising the immunoregulatory macrophage cell of claim 10 or a sub-cellular fraction thereof.

13. Pharmaceutical composition of claim 12, wherein at least 70% of the cells in the composition are immunoregulatory macrophage cells of claim 10.

14. A method of suppressing transplant rejection and/or prolonging transplant survival in a subject receiving a transplant, the method comprising administering an immunoregulatory macrophage cell according to claim 10 or sub-cellular fraction thereof to the subject.

15. The method of claim 14, wherein said transplant is an allogeneic transplant.

16. A method of promoting or sustaining the engraftment or effect of regulatory T cell cell-based medicinal products, the method comprising administering an immunoregulatory macrophage cell according to claim 10 or sub-cellular fraction thereof to a subject in need thereof.

17. A method of treating or preventing an autoimmune disease, an inflammatory disease, or a hypersensitivity reaction, the method comprising administering an immunoregulatory macrophage cell according to claim 10 or sub-cellular fraction thereof to a subject in need thereof.

18. The method of claim 17, wherein said autoimmune disease is selected from the group consisting of systemic lupus erythematosus (SLE), scleroderma, Sjögren's syndrome, polymyositis, dermatomyositis, and other systemic autoimmune conditions; rheumatoid arthritis (RA), juvenile rheumatoid arthritis, and other inflammatory arthritides; ulcerative colitis, Crohn's disease, and other inflammatory bowel diseases; autoimmune hepatitis, primary biliary cirrhosis, and other autoimmune liver diseases; cutaneous small-vessel vasculitis, granulomatosis with polyangiitis, eosinophilic granulomatosis with polyangiitis, Behçet's disease, thromboangiitis obliterans, Kawasaki disease, and other large-, medium- or small-vessel vasculitides of autoimmune aetiology; Multiple sclerosis (MS) and neuroimmunological disorders; Type I diabetes, autoimmune thyroid dysfunction, autoimmune pituitary dysfunction, and other autoimmune endocrinological disorders; haemolytic anaemia, thrombocytopaenic purpura and other autoimmune disorders of the blood and bone marrow; psoriasis, pemphigus vulgaris, pemphigoid and other autoimmune dermatological conditions.

19. The method of claim 17, wherein said inflammatory disease is selected from the group consisting of arterial occlusive diseases, such as peripheral artery occlusive disease (pAOD), critical limb ischaemia, arteriosclerosis, cerebral infarction, myocardial infarction, renal infarction, intestinal infarction, angina pectoris, and other conditions caused by arterial occlusion or constriction; microvascular angina, also known as cardiac syndrome X; inflammation associated systemic with metabolic disorders, including Type II diabetes and obesity-related metabolic syndrome; dermatological diseases, including eczema.

20. The method of claim 17, wherein said hypersensitivity reaction is selected from the group of asthma, eczema, allergic rhinitis, angioedema, drug hypersensitivity and mastocytosis.

21. A method of promoting tissue-repair processes by participating in tissue remodelling, tissue regeneration, angiogenesis, vasculogenesis, or prevention/limitation of fibrosis, the method comprising administering an immunoregulatory macrophage cell according to claim 10 or sub-cellular fraction thereof to a subject in need thereof.

* * * * *